US008796441B2

(12) United States Patent
Drayna et al.

(10) Patent No.: US 8,796,441 B2
(45) Date of Patent: Aug. 5, 2014

(54) HUMAN SWEET AND UMAMI TASTE RECEPTOR VARIANTS

(75) Inventors: Dennis T. Drayna, Potomac, MD (US); Un-Kyung Kim, Daegu (KR)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 982 days.

(21) Appl. No.: 11/911,517

(22) PCT Filed: Apr. 13, 2006

(86) PCT No.: PCT/US2006/014045
§ 371 (c)(1),
(2), (4) Date: Oct. 12, 2007

(87) PCT Pub. No.: WO2006/113422
PCT Pub. Date: Oct. 26, 2006

(65) Prior Publication Data
US 2008/0287310 A1  Nov. 20, 2008

Related U.S. Application Data

(60) Provisional application No. 60/671,173, filed on Apr. 13, 2005.

(51) Int. Cl.
*C07H 21/04* (2006.01)
(52) U.S. Cl.
USPC ........................................ 536/24.3; 536/23.1
(58) Field of Classification Search
None
See application file for complete search history.

(56) References Cited

U.S. PATENT DOCUMENTS

| | | | |
|---|---|---|---|
| 5,688,662 A | 11/1997 | Margolskee et al. | |
| 6,383,778 B1 | 5/2002 | Zuker et al. | |
| 6,582,908 B2 * | 6/2003 | Fodor et al. | 506/9 |
| 6,955,887 B2 | 10/2005 | Adler et al. | |
| 7,504,493 B2 * | 3/2009 | Velculescu et al. | 536/24.32 |
| 2002/0160424 A1 | 10/2002 | Adler et al. | |
| 2002/0168635 A1 | 11/2002 | Zuker et al. | |
| 2003/0040045 A1 | 2/2003 | Zuker et al. | |
| 2003/0166137 A1 | 9/2003 | Zuker et al. | |
| 2003/0220479 A1 | 11/2003 | Li et al. | |
| 2003/0232407 A1 | 12/2003 | Zoller et al. | |
| 2004/0081964 A1 | 4/2004 | Bachmanor et al. | |
| 2004/0171042 A1 | 9/2004 | Adler et al. | |
| 2004/0191862 A1 | 9/2004 | Zoller et al. | |
| 2004/0219632 A1 | 11/2004 | Margolskee et al. | |
| 2005/0032158 A1 | 2/2005 | Adler et al. | |
| 2006/0046253 A1 * | 3/2006 | Nakao et al. | 435/6 |

FOREIGN PATENT DOCUMENTS

| | | |
|---|---|---|
| WO | WO 00/06592 | 2/2000 |
| WO | WO 01/64882 | 9/2001 |
| WO | WO 01/66563 | 9/2001 |
| WO | WO 01/68858 | 9/2001 |
| WO | WO 01/72842 | 10/2001 |
| WO | WO 01/83749 | 11/2001 |
| WO | WO 01/90359 | 11/2001 |
| WO | WO 02/03848 | 1/2002 |
| WO | WO 02/24885 | 3/2002 |
| WO | WO 02/30981 | 4/2002 |
| WO | WO 02/061087 | 8/2002 |
| WO | WO 02/064631 | 8/2002 |
| WO | WO 02/064631 A2 * | 8/2002 |
| WO | WO 02/086079 | 10/2002 |
| WO | WO 03/000893 | 1/2003 |
| WO | WO 03/001876 | 1/2003 |
| WO | WO 03/004992 | 1/2003 |
| WO | WO 03/025137 | 3/2003 |
| WO | WO 2005/033125 | 4/2005 |

OTHER PUBLICATIONS

NEB catalog (1998/1999), pp. 121, 284.*
EMBL-EBI Record having accession AQ842059, Sep. 28, 1999.*
Inoue et al., "Allelic variation of the Tas1r3 taste receptor gene selectively affects behavioral and neural taste responses to sweeteners in the F2 hybrids between C57BL/6ByJ and 129P3/J mice," *Journal of Neuroscience* 24(9): 2296-2303 (2004).
Kim et al., "Variation in the Human TAS1R Taste Receptor Genes," *Chemical Senses* 31(7): 599-611 (2006).
Lu et al., "No relationship between sequence variation in protein coding regions of the Tas1r3 gene and saccharin preference in rats," *Chemical Senses* 30(3): 231-240 (2005).
Reed et al., "Polymorphisms in the taste receptor gene (Tas1r3) region are associated with saccharin preference in 30 mouse strains," *Journal of Neuroscience* 24(4): 938-946, 2004.
Database SNP, "RefSNP ID: rs10864628," XP002397976, retrieved from NCBI Database accession No. NCBI Assay ID: ss18109834.
Adler et al., "A Novel Family of Mammalian Taste Receptors," *Cell*, 100:693-702 (2000).
Bachmanov et al., "Positional Cloning of the Mouse Saccharin Preference (Sac) Locus," *Chem. Senses*, 26:925-933 (2001).
Damak et al., "Detection of sweet and umami taste in the absence of taste receptor T1r3," *Science*, 301(5634):850-3 (2003).
Duffy et al., "Food Acceptance and genetic variation in taste," *J. Am. Diet Assoc.*, 100(6):647-55 (2000).
Gilbertson et al., "The molecular physiology of taste transduction," *Current Opinion in Neurobiology*, 10:519-527 (2000).
Kim et al., "Genetics of Human Taste Perception," *J. Dent. Res*, 83(6):445-453 (2004).
Kitagawa et al., "Molecular genetic identification of a candidate receptor gene for sweet taste," *Biochem. Biophys. Res. Commun.* 282:236-242 (2001).

(Continued)

*Primary Examiner* — Juliet Switzer
(74) *Attorney, Agent, or Firm* — Klarquist Sparkman, LLP

(57) ABSTRACT

Identified herein are different forms of sweet and umami receptor encoding sequences that occur in different human populations. In particular, there are provided several single nucleotide polymorphisms (SNPs) that occur within the exons/coding sequence (and are therefore coding SNPs, cSNPs) of one of the three T1R genes. Some SNPs cause amino acid substitutions, while others introduce a chain termination codon, rendering a truncated product. Differences in these genes are believed to affect the sense of taste of individuals, such that individuals with different SNPs (or different haplotypes) are believed to perceive the taste of sweet or umami (e.g., glutamate) substances differently than the rest of the population. The ability to assay this allelic information is useful in the development of flavorings and flavor enhancers, as it can be used to define groups and populations who perceive tastes differently. This in turn allows the taste preferences of these groups to be addressed at the molecular level.

16 Claims, 12 Drawing Sheets

(56) References Cited

OTHER PUBLICATIONS

Li et al., High-resolution genetic mapping of the saccharin preference locus (Sac) and the putative sweet taste receptor (T1R1) gene (Gpr70) to mouse distal Chromosome 4, *Mamm. Genome*, 12(1):13-6 (2001).

Liao et al., "Three sweet receptor genes are clustered in human chromosome 1," *Mamm. Genome*, 14:291-301 (2003).

Matsunami et al., "Taste Perception: How to make a Gourmet Mouse," *Current Biology*, vol. 14, R118-R120 (2004).

Mennella et al., "Genetic and Environmental Determinants of Bitter Perception and Sweet Preferences," *Pediatrics*, 115:216-222 (2005).

Montmayeur et al., "Receptors for bitter and sweet taste," *Current Opinion in Neurobiology*, 12:366-371 (2002).

Nelson et al., "An Amino-acid taste receptor," *Nature*, 416:199-202 (2002).

Nelson et al., "Mammalian sweet taste receptors," *Cell*, 106:381-390 (2001).

Xu et al., "Different functional roles of T1R subunits in the heteromeric taste receptors," *Proc. Nat. Acad. Sci.*, 101:14258-14263 (2004).

Zhao et al., "The Receptors for Mammalian Sweet and Umami Taste," *Cell*, 115:255-266 (2003).

* cited by examiner

FIG. 1A

Single Nucleotide Polymorphisms in Sweet and Umami Taste Receptor Subunits

| TAS1R1 | | | Chr 1 | BAC clone AL591866 | | CDS BK000153 2526 bp 841 AA | n = 40 | | | | | | | |
|---|---|---|---|---|---|---|---|---|---|---|---|---|---|---|
| dbSNP | Exon | Polymorphism | cSNP | Position of cSNP | amino acid change | Position of protein | Allele Frequency | CAM | AME | NOR | JAP | RUS | HUN | CH | PAR |
| NEW | 2 | C/T (68108) | C | 201 | Ser | 67 | SINGLETON (CAM) | 39 | 16 | 18 | 16 | 20 | 20 | 18 | 14 |
| | | | T | | Ser | | | 1 | 0 | 0 | 0 | 0 | 0 | 0 | 0 |
| NEW | 2 | A/G (68191) | A | 284 | Asn | 95 | SINGLETON (PAR) | 40 | 20 | 20 | 20 | 20 | 20 | 20 | 15 |
| | | | G | | Ser | | | 0 | 0 | 0 | 0 | 0 | 0 | 0 | 1 |
| NEW | 2 | C/T (68236) | C | 329 | Ala | 110 | SINGLETON (NOR) | 40 | 20 | 19 | 20 | 14 | 20 | 20 | 14 |
| | | | T | | Val | | | 0 | 0 | 1 | 0 | 0 | 0 | 0 | 0 |
| NEW | 2 | C/A (68283) | C | 376 | His | 126 | | 38 | 20 | 20 | 20 | 14 | 20 | 20 | 14 |
| | | | A | | Asn | | | 2 | 0 | 0 | 0 | 0 | 0 | 0 | 0 |
| NEW | 2 | T/C (68287) | T | 380 | Ile | 127 | | 38 | 20 | 20 | 20 | 14 | 20 | 17 | 14 |
| | | | C | | Thr | | | 0 | 0 | 0 | 0 | 0 | 0 | 3 | 0 |
| NEW | 3 | T/C (71823) | T | 501 | Ile | 167 | | 40 | 20 | 20 | 20 | 20 | 20 | 17 | 16 |
| | | | C | | Ile | | | 0 | 0 | 0 | 0 | 0 | 0 | 3 | 0 |
| NEW | 3 | C/G (71863) | C | 541 | Gln | 181 | | 38 | 20 | 20 | 20 | 20 | 20 | 20 | 16 |
| | | | G | | Glu | | | 2 | 0 | 0 | 0 | 0 | 0 | 0 | 0 |
| NEW | 3 | A/G (71867) | A | 545 | Tyr | 182 | SINGLETON (PAR) | 40 | 20 | 20 | 20 | 20 | 20 | 20 | 15 |
| | | | G | | Cys | | | 0 | 0 | 0 | 0 | 0 | 0 | 0 | 1 |
| NEW | 3 | A/G (71894) | A | 572 | Asn | 191 | | 40 | 20 | 20 | 20 | 20 | 20 | 16 | 16 |
| | | | G | | Ser | | | 0 | 0 | 0 | 0 | 0 | 0 | 4 | 0 |
| NEW | 3 | A/C (72031) | A | 709 | Ile | 237 | | 40 | 20 | 20 | 20 | 20 | 20 | 17 | 16 |
| | | | C | | Leu | | | 0 | 0 | 0 | 0 | 0 | 0 | 3 | 0 |
| rs10864628 | 3 | G/A (72361) | G | 1039 | Glu | 347 | | 31 | 20 | 20 | 20 | 20 | 20 | 20 | 16 |
| | | | A | | Lys | | | 9 | 0 | 0 | 0 | 0 | 0 | 0 | 0 |
| NEW | 3 | G/A (72436) | G | 1114 | Ala | 372 | | 36 | 20 | 15 | 13 | 19 | 13 | 12 | 15 |
| | | | A | | Thr | | | 4 | 0 | 5 | 7 | 1 | 7 | 8 | 1 |
| NEW | 3 | C/A (72439) | C | 1117 | His | 373 | SINGLETON (CAM) | 39 | 20 | 20 | 20 | 20 | 20 | 20 | 16 |
| | | | A | | Asn | | | 1 | 0 | 0 | 0 | 0 | 0 | 0 | 0 |
| NEW | 4 | T/C (73972) | T | 1448 | Ile | 483 | | 40 | 20 | 20 | 20 | 20 | 20 | 17 | 14 |

FIG. 1B

Single Nucleotide Polymorphisms in Sweet and Umami Taste Receptor Subunits

| dbSNP | Exon | Polymorphism | cSNP | Position of cSNP | amino acid change | Position of protein | Allele Frequency | CAM | AME | NOR | JAP | RUS | HUN | CH | PAR |
|---|---|---|---|---|---|---|---|---|---|---|---|---|---|---|---|
| NEW | 6 | G/A(76056) | G | 1808 | Arg | 603 | | 35 | 18 | 20 | 20 | 18 | 20 | 3 | 0 |
| | | | A | | His | | 1 | 5 | 0 | 0 | 0 | 0 | 0 | 20 | 16 |
| NEW | 6 | G/A(76522) | G | 2274 | Glu | 758 | | 25 | 14 | 20 | 20 | 16 | 16 | 18 | 0 |
| | | | A | | Glu | | | 9 | 0 | 0 | 0 | 0 | 0 | 0 | 16 |
| NEW | 6 | G/A(76566) | G | 2318 | Trp | 773 | | 32 | 14 | 20 | 20 | 20 | 16 | 18 | 0 |
| | | | A | | Stop | | 2 | 0 | 0 | 0 | 0 | 0 | 0 | 0 | 16 |

TAS1R2  Chr1  BAC clones: BX531760 (−) (exon 1 & 2) AL831755 (−) (exon 3–6)  CDS BK000151  2520bp  839AA  n = 40

| dbSNP | Exon | Polymorphism | cSNP | Position of cSNP | amino acid change | Position of protein | Allele Frequency | CAM | AME | NOR | JAP | RUS | HUN | CH | PAR |
|---|---|---|---|---|---|---|---|---|---|---|---|---|---|---|---|
| NEW | 1 | C/G (4985) | C | 26 | Ser | 9 | SINGLETON (CAM) | 10 | 6 | 8 | 4 | 7 | 4 | 3 | 2 |
| NEW | 1 | C/T (4949) | C | 62 | Pro | 21 | 7 POP | 30 | 14 | 12 | 16 | 13 | 16 | 17 | 12 |
| | | | T | | Leu | | | 39 | 20 | 20 | 20 | 20 | 20 | 20 | 16 |
| NEW | 3 | A/G (90090) | A | 571 | Ile | 191 | | 1 | 0 | 0 | 0 | 0 | 0 | 0 | 0 |
| | | | G | | Val | | | 27 | 14 | 14 | 17 | 10 | 12 | 20 | 11 |
| NEW | 3 | A/G (90027) | A | 634 | Ser | 212 | | 11 | 6 | 4 | 3 | 8 | 4 | 0 | 5 |
| | | | G | | Gly | | | 37 | 20 | 18 | 20 | 18 | 16 | 20 | 16 |
| NEW | 3 | A/G (89961) | A | 700 | Ile | 234 | SINGLETON (CAM) | 3 | 0 | 0 | 0 | 0 | 0 | 0 | 0 |
| | | | G | | Val | | | 39 | 20 | 18 | 20 | 18 | 16 | 20 | 16 |
| NEW | 3 | T/G (89779) | T | 882 | Thr | 294 | | 1 | 0 | 0 | 0 | 0 | 0 | 0 | 0 |
| | | | G | | Thr | | | 32 | 14 | 14 | 17 | 10 | 12 | 20 | 11 |
| NEW | 3 | G/C (89712) | G | 949 | Gly | 317 | | 8 | 6 | 4 | 3 | 8 | 4 | 0 | 5 |
| | | | C | | Arg | | | 8 | 6 | 4 | 3 | 7 | 4 | 0 | 5 |
| NEW | 4 | G/A (84679) | G | 1320 | Pro | 440 | SINGLETON (HUN) | 32 | 14 | 14 | 17 | 11 | 12 | 20 | 11 |
| | | | A | | Pro | | | 40 | 20 | 20 | 20 | 20 | 19 | 20 | 16 |
| NEW | 4 | G/A (84655) | G | 1344 | Leu | 448 | SINGLETON (CAM) | 0 | 0 | 0 | 0 | 0 | 1 | 0 | 0 |
| | | | A | | Leu | | | 39 | 20 | 20 | 20 | 20 | 20 | 20 | 16 |
| NEW | 4 | A/G (84543) | A | 1456 | Val | 486 | | 1 | 0 | 0 | 0 | 0 | 0 | 0 | 0 |
| | | | G | | Val | | | 35 | 11 | 17 | 20 | 14 | 16 | 20 | 12 |

FIG. 1C

Single Nucleotide Polymorphisms in Sweet and Umami Taste Receptor Subunits

| dbSNP | Exon | Polymorphism | cSNP | Position of cSNP | amino acid change | Position of protein | Allele Frequency | CAM | AME | NOR | JAP | RUS | HUN | CH | PAR |
|---|---|---|---|---|---|---|---|---|---|---|---|---|---|---|---|
| NEW | 6 | C/T (75591) | G | | Ile | | | 5 | 29 | 9 | 3 | 0 | 6 | 4 | 0 | 4 |
| | | | C | 1719 | Ala | 573 | | 0 | 5 | 0 | 0 | 0 | 0 | 0 | 0 | 0 |
| | | | T | | Ala | | | | | | | | | | | |
| NEW | 6 | G/A (75590) | G | 1720 | Ala | 574 | | 34 | 14 | 17 | 15 | 16 | 16 | 15 | 14 |
| | | | A | | Thr | | | 0 | 0 | 1 | 5 | 0 | 2 | 1 | 2 |
| NEW | 6 | A/C (75245) | A | 2065 | Lys | 689 | SINGLETON (CAM) | 33 | 18 | 18 | 18 | 18 | 18 | 16 | 14 |
| | | | C | | Gln | | | 1 | 0 | 0 | 0 | 0 | 0 | 0 | 0 |
| NEW | 6 | C/T (75218) | C | 2092 | Leu | 698 | | 31 | 18 | 18 | 18 | 18 | 18 | 16 | 14 |
| | | | T | | Leu | | | 3 | 0 | 0 | 0 | 0 | 0 | 0 | 0 |
| NEW | 6 | C/T (75198) | C | 2112 | Pro | 704 | SINGLETON (NOR) | 36 | 18 | 17 | 17 | 18 | 18 | 16 | 14 |
| | | | T | | Pro | | | 0 | 0 | 1 | 0 | 0 | 0 | 0 | 0 |
| NEW | 6 | C/T (74991) | C | 2319 | Ser | 773 | | 27 | 15 | 11 | 13 | 14 | 13 | 8 | 12 |
| | | | T | | Ser | | | 13 | 5 | 9 | 7 | 2 | 7 | 12 | 4 |
| NEW | 6 | C/T (74940) | C | 2370 | Ile | 790 | | 38 | 20 | 18 | 15 | 20 | 18 | 19 | 14 |
| | | | T | | Ile | | | 0 | 0 | 2 | 5 | 0 | 2 | 1 | 2 |
| NEW | 6 | G/A (74797) | G | 2513 | Arg | 838 | | 33 | 20 | 18 | 20 | 18 | 18 | 20 | 14 |
| | | | A | | Lys | | | 5 | 0 | 0 | 0 | 0 | 0 | 0 | 0 |

| TAS1R3 | Chr1 | BAC cloneAL139287 (+) | CDS BK000152 | 2559 bp | 852 AA | | n = 40 | | | | | | | | |
|---|---|---|---|---|---|---|---|---|---|---|---|---|---|---|---|
| dbSNP | Exon | Polymorphism | cSNP | Position of cSNP | amino acid change | Position of protein | Allele Frequency | CAM | AME | NOR | JAP | RUS | HUN | CH | PAR |
| NEW | 1 | G/A (31311) | G | 13 | Ala | 5 | 0.99 | 36 | 20 | 18 | 20 | 18 | 19 | 20 | 16 |
| | | | A | | Thr | | 0.01 | 0 | 0 | 2 | 0 | 0 | 1 | 0 | 0 |
| NEW | 2 | T/C (31683) | T | 284 | Leu | 95 | 0.99 SINGLETON (CAM) | 39 | 20 | 18 | 20 | 20 | 20 | 20 | 16 |
| | | | C | | Pro | | 0.01 | 1 | 0 | 0 | 0 | 0 | 0 | 0 | 0 |
| NEW | 3 | G/A (32224) | G | 740 | Arg | 247 | | 30 | 20 | 18 | 20 | 18 | 20 | 20 | 16 |
| | | | A | | His | | | 10 | 0 | 0 | 0 | 0 | 0 | 0 | 0 |
| NEW | 3 | G/T (32583) | G | 1099 | Gly | 367 | 0.99 | 38 | 18 | 20 | 20 | 20 | 20 | 20 | 16 |

FIG. 1D

Single Nucleotide Polymorphisms in Sweet and Umami Taste Receptor Subunits

| | | | | | | | | | | | | | | | | |
|---|---|---|---|---|---|---|---|---|---|---|---|---|---|---|---|---|
| rs3813210 | 3 | C/T (32732) | T | 1248 | Cys | | 0.01 | 2 | 0 | 0 | 0 | 0 | 0 | 0 | 0 | 0 |
| | | | C | | Pro | 416 | 0.68 | 23 | 18 | 18 | 17 | 20 | 18 | 20 | 19 | 16 |
| | | | T | | Pro | | 0.32 | 17 | 0 | 0 | 3 | 0 | 0 | 0 | 1 | 0 |
| NEW | 4 | G/A (32921) | G | 1323 | Pro | 441 | 0.95 | 30 | 16 | 18 | 20 | 19 | 20 | 20 | 20 | 12 |
| | | | A | | Pro | | 0.05 | 4 | 0 | 0 | 0 | 1 | 0 | 0 | 0 | 0 |
| NEW | 4 | C/T (32960) | C | 1362 | Tyr | 454 | 0.99 | 33 | 16 | 18 | 20 | 20 | 20 | 20 | 20 | 10 |
| | | | T | | Tyr | | 0.01 | 1 | 0 | 0 | 0 | 0 | 0 | 0 | 0 | 0 |
| NEW | 6 | C/T (33577) | C | 1719 | Leu | 573 | 0.99 | 38 | 20 | 20 | 18 | 16 | 20 | 20 | 20 | 16 |
| | | | T | | Leu | | 0.01 | 0 | 0 | 0 | 2 | 0 | 0 | 0 | 0 | 0 |
| NEW | 6 | C/T (33835) | C | 1977 | Phe | 659 | 0.99 SINGLETON (JAP) | 40 | 20 | 18 | 19 | 16 | 16 | 20 | 20 | 16 |
| | | | T | | Phe | | 0.01 | 0 | 0 | 0 | 1 | 0 | 0 | 0 | 0 | 0 |
| NEW | 6 | G/A (34061) | G | 2203 | Ala | 735 | 0.77 | 30 | 20 | 18 | 20 | 20 | 16 | 20 | 20 | 16 |
| | | | A | | Thr | | 0.23 | 10 | 0 | 0 | 0 | 0 | 0 | 0 | 0 | 0 |
| rs307377 | 6 | T/C (34127) | T | 2269 | Cys | 757 | 0.05 | 40 | 20 | 18 | 20 | 16 | 19 | 19 | 18 | 15 |
| | | | C | | Arg | | 0.95 | 0 | 0 | 0 | 0 | 0 | 1 | 0 | 0 | 1 |
| NEW | 6 | C/T (34265) | C | 2407 | Leu | 803 | 0.95 SINGLETON (RUS) | 40 | 20 | 18 | 20 | 17 | 20 | 20 | 18 | 16 |
| | | | T | | Leu | | 0.01 | 0 | 0 | 0 | 0 | 1 | 0 | 0 | 0 | 0 |

FIG. 2A

Alignment of T1R1 Isoforms (based on differential splicing)

```
            1          15 16         30 31         45 46         60 61         75 76         90
1 T1R1v4  ATGCTGCTCTGCACG GCTCGCCTGGTCGGC CTGCAGCTTCTCATT TCCTGCTGCTGGGCC TTTGCCTGCCATAGC ACGGAGTCTTCTCCT   90
2 T1R1v3  ATGCTGCTCTGCACG GCTCGCCTGGTCGGC CTGCAGCTTCTCATT TCCTGCTGCTGGGCC TTTGCCTGCCATAGC ACGGAGTCTTCTCCT   90
3 T1R1v1  ATGCTGCTCTGCACG GCTCGCCTGGTCGGC CTGCAGCTTCTCATT TCCTGCTGCTGGGCC TTTGCCTGCCATAGC ACGGAGTCTTCTCCT   90
4 T1R1v2  ATGCTGCTCTGCACG GCTCGCCTGGTCGGC CTGCAGCTTCTCATT TCCTGCTGCTGGGCC TTTGCCTGCCATAGC ACGGAGTCTTCTCCT   90

91        105 106       120 121       135 136       150 151       165 166       180
1 T1R1v4  GACTTCACCCTCCCC GGAGATTACCTCCTG GCAGGCCTGTTCCCT CTCCATTCTGGCTGT CTGCAGGTGAGGCAC AGACCCGAGGTGACC  180
2 T1R1v3  GACTTCACCCTCCCC GGAGATTACCTCCTG GCAGGCCTGTTCCCT CTCCATTCTGGCTGT CTGCAGGTGAGGCAC AGACCCGAGGTGACC  180
3 T1R1v1  GACTTCACCCTCCCC GGAGATTACCTCCTG GCAGGCCTGTTCCCT CTCCATTCTGGCTGT CTGCAGGTGAGGCAC AGACCCGAGGTGACC  180
4 T1R1v2  GACTTCACCCTCCCC GGAGATTACCTCCTG GCAGGCCTGTTCCCT CTCCATTCTGGCTGT CTGCAGGTGAGGCAC AGACCCGAGGTGACC  180

181        195 196       210 211       225 226       240 241       255 256       270
1 T1R1v4  CTGTGTGACAGGTCT TGTAGCTTCAATGAG CATGGCTACCACCTC TTCCAGGCTATGCGG CTTGGGGTTGAGGAG ATAAACAACTCCACG  270
2 T1R1v3  CTGTGTGACAGGTCT TGTAGCTTCAATGAG CATGGCTACCACCTC TTCCAGGCTATGCGG CTTGGGGTTGAGGAG ATAAACAACTCCACG  270
3 T1R1v1  CTGTGTGACAGGTCT TGTAGCTTCAATGAG CATGGCTACCACCTC TTCCAGGCTATGCGG CTTGGGGTTGAGGAG ATAAACAACTCCACG  270
4 T1R1v2  CTGTGTGACAGGTCT TGTAGCTTCAATGAG CATGGCTACCACCTC TTCCAGGCTATGCGG CTTGGGGTTGAGGAG ATAAACAACTCCACG  270
                             T 271        285 286       300 301       315 316       330 331       345 346       360
1 T1R1v4  GCCCTGCTGCCCAAC ATCACCCTGGGGTAC CAGCTGTATGATGTG TGTTCTGACTCTGCC AATGTGTATGCCACG CTGAGAGTGCTCTCC  360
2 T1R1v3  GCCCTGCTGCCCAAC ATCACCCTGGGGTAC CAGCTGTATGATGTG TGTTCTGACTCTGCC AATGTGTATGCCACG CTGAGAGTGCTCTCC  360
3 T1R1v1  GCCCTGCTGCCCAAC ATCACCCTGGGGTAC CAGCTGTATGATGTG TGTTCTGACTCTGCC AATGTGTATGCCACG CTGAGAGTGCTCTCC  360
4 T1R1v2  GCCCTGCTGCCCAAC ATCACCCTGGGTAC  CAGCTGTATGATGTG TGTTCTGACTCTGCC AATGTGTATGCCACG CTGAGAGTGCTCTCC  360
                              G                                  T 361        375 376       390 391       405 406       420 421       435 436       450
1 T1R1v4  CTGCCAGGGCAACAC CACATAGAGCTCCAA GGAGACCTTCTCCAC TATTCCCCTACGGTG CTGGCAGTGATTGGG CCTGACACAGCACCAAC 450
2 T1R1v3  CTGCCAGGGCAACAC CACATAGAGCTCCAA GGAGACCTTCTCCAC TATTCCCCTACGGTG CTGGCAGTGATTGGG CCTGACACAGCACCAAC 450
3 T1R1v1  CTGCCAGGGCAACAC CACATAGAGCTCCAA GGAGACCTTCTCCAC TATTCCCCTACGGTG CTGGCAGTGATTGGG CCTGACACAGCACCAAC 450
4 T1R1v2  CTGCCAGGGCAACAC CACATAGAGCTCCAA GGAGACCTTCTCCAC TATTCCCCTACGGTG CTGGCAGTGATTGGG CCTGACACAGCACCAAC 450
                          A   C 451        465 466       480 481       495 496       510 511       525 526       540
1 T1R1v4  CGTGCTGCCACCACA GCCGCCCTGCTGAGC CCTTTCCTGGTGCCC ATGCTT--------- --------------- ---------------  501
2 T1R1v3  CGTGCTGCCACCACA GCCGCCCTGCTGAGC CCTTTCCTGGTGCCC ATGCTT--------- --------------- ---------------  501
3 T1R1v1  CGTGCTGCCACCACA GCCGCCCTGCTGAGC CCTTTCCTGGTGCCC ATGATTAGCTATGCG GCCAGCAGCGAGACG CTCAGCGTGAAGCGG  540
4 T1R1v2  CGTGCTGCCACCACA GCCGCCCTGCTGAGC CCTTTCCTGGTGCCC ATGATTAGCTATGCG GCCAGCAGCGAGACG CTCAGCGTGAAGCGG  540
                                                                       C
```

FIG. 2B

Alignment of T1R1 Isoforms (based on differential splicing)

```
         541         555 556         570 571         585 586         600 601         615 616         630
1 T1R1v4 ---         --- ---         --- ---         --- ---         --- ---         --- ---         ---    501
2 T1R1v3 ---         --- ---         --- ---         --- ---         --- ---         --- ---         ---    501
3 T1R1v1 CAGTATCCCTCTTTC CTGCGCACCATCCCC AATGACAAGTACCAG GTGGAGACCATGGTG CTGCTGCTGCAGAAG TTCGGGTGGACCTGG    630
4 T1R1v2 CAGTATCCCTCTTTC CTGCGCACCATCCCC AATGACAAGTACCAG GTGGAGACCATGGTG CTGCTGCTGCAGAAG TTCGGGTGGACCTGG    630
         G G                             G 631         645 646         660 661         675 676         690 691         705 706         720
1 T1R1v4 ---         --- ---         --- ---         --- ---         --- ---         --- ---         ---    501
2 T1R1v3 ---         --- ---         --- ---         --- ---         --- ---         --- ---         ---    501
3 T1R1v1 ATCTCTCTGGTTGGC AGCAGTGACGACTAT GGGCAGCTAGGGGTG CAGGCCACTGGAGAAC CAGGCCACTGGTCAG GGGATCTGCATTGCT    720
4 T1R1v2 ATCTCTCTGGTTGGC AGCAGTGACGACTAT GGGCAGCTAGGGGTG CAGGCCACTGGAGAAC CAGGCCACTGGTCAG GGGATCTGCATTGCT    720
                                                                                                        C 721         735 736         750 751         765 766         780 781         795 796         810
1 T1R1v4 ---         --- ---         --- ---         --- ---         --- ---         --- ---         ---    501
2 T1R1v3 ---         --- ---         --- ---         --- ---         --- ---         --- ---         ---    501
3 T1R1v1 TTCAAGGACATCATG CCCTTCTCTGCCCAG GTGGGCGATGAGAGG ATGCAGTGCCTCATG CGCCACCTGGCCCAG GCCGGGGCCACCGTC    810
4 T1R1v2 TTCAAGGACATCATG CCCTTCTCTGCCCAG GTGGGCGATGAGAGG ATGCAGTGCCTCATG CGCCACCTGGCCCAG GCCGGGGCCACCGTC    810

811         825 826         840 841         855 856         870 871         885 886         900
1 T1R1v4 ---         --- ---         --- ---         --- ---         --- ---         --- ---         ---    501
2 T1R1v3 ---         --- ---         --- ---         --- ---         --- ---         --- ---         ---    501
3 T1R1v1 GTGGTTGTTTTTTCC AGCCGGCAGTTGGCC AGGGTGTTTTTCGAG TCCGTGGTGCTGACC AACCTGACTGGCAAG GTGTGGGTCGCCTCA    900
4 T1R1v2 GTGGTTGTTTTTTCC AGCCGGCAGTTGGCC AGGGTGTTTTTCGAG TCCGTGGTGCTGACC AACCTGACTGGCAAG GTGTGGGTCGCCTCA    900

901         915 916         930 931         945 946         960 961         975 976         990
1 T1R1v4 ---         --- ---         --- ---         --- ---         --- ---         --- ---         ---    501
2 T1R1v3 ---         --- ---         --- ---         --- ---         --- ---         --- ---         ---    501
3 T1R1v1 GAAGCCTGGCCCTC TCCAGGCACATCACT GGGGTGCCCGGGATC CAGCGCATTGGGATG GTGCTGGGCGTGGCC ATCCAGAAGAGGGCT    990
4 T1R1v2 GAAGCCTGGCCCTC TCCAGGCACATCACT GGGGTGCCCGGGATC CAGCGCATTGGGATG GTGCTGGGCGTGGCC ATCCAGAAGAGGGCT    990

991         1005 1006       1020 1021       1035 1036       1050 1051       1065 1066       1080
1 T1R1v4 ---         ---  ---         ---  ---         ---  ---         ---  ---         ---  ---         ---   501
2 T1R1v3 ---         ---  ---         ---  ---         ---  ---         ---  ---         ---  ---         ---   501
3 T1R1v1 GTCCCTGGCCTGAAG GCGTTTGAAGAAGCC TATGCCCGGGCAGAC AAGAAGGCCCCCTAGG CCTTGCCACAAGGGC TCCTGGTGCAGCAGC    1080
4 T1R1v2 GTCCCTGGCCTGAAG GCGTTTGAAGAAGCC TATGCCCGGGCAGAC AAGAAGGCCCCCTAGG CCTTGCCACAAGGGC TCCTGGTGCAGCAGC    1080
                                                           G
```

FIG. 2C

Alignment of T1R1 Isoforms (based on differential splicing)

```
            1081       1095 1096                                                      1155 1156                         1170
1 T1R1v4    ----------------------------------------------------------------------------------------------------------      501
2 T1R1v3    ----------------------------------------------------------------------------------------------------------      501
3 T1R1v1    AATCAGCTCTGCAGA GAATGCCAAGCTTTC ATGGCACACACGATG CCCAAGCTCAAAGCC TTCTCCATGAGTTCT GCCTACAACGCATAC                  1170
4 T1R1v2    AATCAGCTCTGCAGA GAATGCCAAGCTTTC ATGGCACACACGATG CCCAAGCTCAAAGCC TTCTCCATGAGTTCT GCCTACAACGCATAC                  1170
                                             A A 1171       1185 1186                 1200 1201       1215 1216       1230 1231       1245 1246                 1260
1 T1R1v4    ----------------------------------------------------------------------------------------------------------      501
2 T1R1v3    ----------------------------------------------------------------------------------------------------------      501
3 T1R1v1    CGGGCTGTGTATGCG GTGGCCCATGGCCTC CACCAGCTCCTGGGC TGTGCCTCTGGAGCT TGTTCCAGGGGCCGA GTCTACCCCTGGCAG                  1260
4 T1R1v2    CGGGCTGTGTATGCG GTGGCCCATGGCCTC CACCAGCTCCTGGGC TGTGCCTCTGGAGCT TGTTCCAGGGGCCGA GTCTACCCCTGGCAG                  1260

1261       1275 1276                 1290 1291       1305 1306       1320 1321       1335 1336                 1350
1 T1R1v4    ---TTGGAGCAGATC CACAAGGTGCATTTC CTTCTACACAAGGAC ACTGTGGCGTTTAAT GACAACAGAGATCCC CTCAGTAGCTATAAC                   588
2 T1R1v3    ---TTGGAGCAGATC CACAAGGTGCATTTC CTTCTACACAAGGAC ACTGTGGCGTTTAAT GACAACAGAGATCCC CTCAGTAGCTATAAC                   588
3 T1R1v1    ----------------------------------------------------------------------------------------------------------     1260
4 T1R1v2    CTTTTGGAGCAGATC CACAAGGTGCATTTC CTTCTACACAAGGAC ACTGTGGCGTTTAAT GACAACAGAGATCCC CTCAGTAGCTATAAC                  1350

1351       1365 1366                 1380 1381       1395 1396       1410 1411       1425 1426                 1440
1 T1R1v4    ATAATTGCCTGGGAC TGGAATGGACCCAAG TGGACCTTCACGGTC CTCGGTTCCTCCACA TGGTCTCCAGTTCAG CTAAACATAAATGAG                   678
2 T1R1v3    ATAATTGCCTGGGAC TGGAATGGACCCAAG TGGACCTTCACGGTC CTCGGTTCCTCCACA TGGTCTCCAGTTCAG CTAAACATAAATGAG                   678
3 T1R1v1    ----------------------------------------------------------------------------------------------------------     1260
4 T1R1v2    ATAATTGCCTGGGAC TGGAATGGACCCAAG TGGACCTTCACGGTC CTCGGTTCCTCCACA TGGTCTCCAGTTCAG CTAAACATAAATGAG                  1440

1441       1455 1456                 1470 1471       1485 1486       1500 1501       1515 1516                 1530
1 T1R1v4    ACCAAAATCCAGTGG CACGGAAAGGACAAC CAGGTGCCTAAGTCT GTGTGTTCCAGCGAC TGTCTTGAAGGGCAC CAGCGAGTGGTTACG                   768
2 T1R1v3    ACCAAAATCCAGTGG CACGGAAAGGACAAC CAGGTGCCTAAGTCT GTGTGTTCCAGCGAC TGTCTTGAAGGGCAC CAGCGAGTGGTTACG                   768
3 T1R1v1    ----------------------------------------------------------------------------------------------------------     1260
4 T1R1v2    ACCAAAATCCAGTGG CACGGAAAGGACAAC CAGGTGCCTAAGTCT GTGTGTTCCAGCGAC TGTCTTGAAGGGCAC CAGCGAGTGGTTACG                  1530
               C 1531       1545 1546                 1560 1561       1575 1576       1590 1591       1605 1606                 1620
1 T1R1v4    GGTTTCCATCACTGC TGCTTTGAGTGTGTG CCCTGTGGGGCTGGG ACCTTCCTCAACAAG AGT------------ ---------------                   831
2 T1R1v3    GGTTTCCATCACTGC TGCTTTGAGTGTGTG CCCTGTGGGGCTGGG ACCTTCCTCAACAAG AGTGACCTCTACACA TGCCAGCCTTGTGGG                   858
3 T1R1v1    --------------- --------------- --------------- --------------- ---ACCTCTACAGA TGCCAGCCTTGTGGG                  1286
4 T1R1v2    GGTTTCCATCACTGC TGCTTTGAGTGTGTG CCCTGTGGGGCTGGG ACCTTCCTCAACAAG AGTGACCTCTACAGA TGCCAGCCTTGTGGG                  1620
```

FIG. 2D

Alignment of T1R1 Isoforms (based on differential splicing)

```
         1621       1635 1636                                                                             1695 1696                           1710
1 T1R1v4 ------------------------------------------------------------------------------------------------------------------------------------  831
2 T1R1v3 AAAGAAGAGAGTGGGCA CCTGAGGGAAGCCAG ACCTGCTTCCCGCGC ACTGTGGTGTTTTTG GCTTTGCGTGAGCAC ACCTCTTGGTGCTG  948
3 T1R1v1 AAAGAAGAGAGTGGGCA CCTGAGGGAAGCCAG ACCTGCTTCCCGCGC ACTGTGGTGTTTTTG GCTTTGCGTGAGCAC ACCTCTTGGTGCTG 1376
4 T1R1v2 AAAGAAGAGAGTGGGCA CCTGAGGGAAGCCAG ACCTGCTTCCCGCGC ACTGTGGTGTTTTTG GCTTTGCGTGAGCAC ACCTCTTGGTGCTG 1710

1711       1725 1726            1740 1741            1755 1756            1770 1771            1785 1786                           1800
1 T1R1v4 ------------------------------------------------------------------------------------------------------------------------------------  831
2 T1R1v3 CTGCAGCTAACACG CTGCTGCTGCTGCTG CTGCTGCTGCTGCTG GGCCTGTTTGCCTGG CACCTAGACACCCCT GTGGTGAGGTCAGCA 1038
3 T1R1v1 CTGGCAGCTAACACG CTGCTGCTGCTGCTG CTGCTGCTGCTGCTG GGCCTGTTTGCCTGG CACCTAGACACCCCT GTGGTGAGGTCAGCA 1466
4 T1R1v2 CTGGCAGCTAACACG CTGCTGCTGCTGCTG CTGCTGCTGCTGCTG GGCCTGTTTGCCTGG CACCTAGACACCCCT GTGGTGAGGTCAGCA 1800

1801       1815 1816            1830 1831            1845 1846            1860 1861            1875 1876                           1890
1 T1R1v4 ------------------------------------------------------------------------------------------------------------------------------------  831
2 T1R1v3 GGGGGCCGCCTGTGC TTTCTTATGCTGGGC TCCCTGGCAGCAGGT AGTGGCAGCCTCTAT GGCTTCTTTGGGAA CCCACAAGGCCTGCG 1128
3 T1R1v1 GGGGGCCGCCTGTGC TTTCTTATGCTGGGC TCCCTGGCAGCAGGT AGTGGCAGCCTCTAT GGCTTCTTTGGGAA CCCACAAGGCCTGCG 1556
4 T1R1v2 GGGGGCCGCCTGTGC TTTCTTATGCTGGGC TCCCTGGCAGCAGGT AGTGGCAGCCTCTAT GGCTTCTTTGGGAA CCCACAAGGCCTGCG 1890
              A 1891       1905 1906            1920 1921            1935 1936            1950 1951            1965 1966                           1980
1 T1R1v4 ------------------------------------------------------------------------------------------------------------------------------------  831
2 T1R1v3 TGCTTGCTACGCCAG GCCCTCTTTGCCCTT GGTTTCACCATCTTC CTGTCCTGCCTGACA GTTCGCTCATTCCAA CTAATCATCATCTTC 1218
3 T1R1v1 TGCTTGCTACGCCAG GCCCTCTTTGCCCTT GGTTTCACCATCTTC CTGTCCTGCCTGACA GTTCGCTCATTCCAA CTAATCATCATCTTC 1646
4 T1R1v2 TGCTTGCTACGCCAG GCCCTCTTTGCCCTT GGTTTCACCATCTTC CTGTCCTGCCTGACA GTTCGCTCATTCCAA CTAATCATCATCTTC 1980

1981       1995 1996            2010 2011            2025 2026            2040 2041            2055 2056                           2070
1 T1R1v4 ------------------------------------------------------------------------------------------------------------------------------------  831
2 T1R1v3 AAGTTTTCCACCAAG GTACCTACATTCTAC CACGCCTGGGTCCAA AACCACGGTGCTGGC CTGTTTGTGATGATC AGCTCAGCGGCCCAG 1308
3 T1R1v1 AAGTTTTCCACCAAG GTACCTACATTCTAC CACGCCTGGGTCCAA AACCACGGTGCTGGC CTGTTTGTGATGATC AGCTCAGCGGCCCAG 1736
4 T1R1v2 AAGTTTTCCACCAAG GTACCTACATTCTAC CACGCCTGGGTCCAA AACCACGGTGCTGGC CTGTTTGTGATGATC AGCTCAGCGGCCCAG 2070

2071       2085 2086            2100 2101            2115 2116            2130 2131            2145 2146                           2160
1 T1R1v4 ------------------------------------------------------------------------------------------------------------------------------------  831
2 T1R1v3 CTGCTTATCTGTCTA ACTTGGCTGGTGGTG TGGACCCCACTGCCT GCTAGGGAATACCAG CGCTTCCCCCATCTG GTGATGCTTGAGTGC 1398
3 T1R1v1 CTGCTTATCTGTCTA ACTTGGCTGGTGGTG TGGACCCCACTGCCT GCTAGGGAATACCAG CGCTTCCCCCATCTG GTGATGCTTGAGTGC 1826
4 T1R1v2 CTGCTTATCTGTCTA ACTTGGCTGGTGGTG TGGACCCCACTGCCT GCTAGGGAATACCAG CGCTTCCCCCATCTG GTGATGCTTGAGTGC 2160

2161       2175 2176            2190 2191            2205 2206            2220 2221            2235 2236                           2250
1 T1R1v4 ------------------------------------------------------------------------------------------------------------------  845
2 T1R1v3 ACAGAGACCAACTCC CTGGGCTTCATACTG GCCTTCCTCTACAAT GGCCTCCTCTCCATC AGTGCCTTTGCCTGC -GCTACCTGGGTAAG 1488
3 T1R1v1 ACAGAGACCAACTCC CTGGGCTTCATACTG GCCTTCCTCTACAAT GGCCTCCTCTCCATC AGTGCCTTTGCCTGC AGCTACCTGGGTAAG 1916
```

FIG. 2E

Alignment of T1R1 Isoforms (based on differential splicing)

```
4 T1R1v2 ACAGAGACCAACTCC CTGGGCTTCATACTG GCCTTCCTCTACAAT GGCCTTCCTCTCCATC AGTGCCTTTGCCTGC AGCTACCTGGGTAAG 2250

2251            2266            2281            2296            2311            2326
1 T1R1v4 GACTTGCCAGAGAAC TACAACGAGGCCAAA TGTGTCACCTTCAGC CTGCTCTTCAACTTC GTGTCCTGGATCGCC TTCTTCACCACGGCC  935
2 T1R1v3 GACTTGCCAGAGAAC TACAACGAGGCCAAA TGTGTCACCTTCAGC CTGCTCTTCAACTTC GTGTCCTGGATCGCC TTCTTCACCACGGCC 1578
3 T1R1v1 GACTTGCCAGAGAAC TACAACGAGGCCAAA TGTGTCACCTTCAGC CTGCTCTTCAACTTC GTGTCCTGGATCGCC TTCTTCACCACGGCC 2006
4 T1R1v2 GACTTGCCAGAGAAC TACAACGAGGCCAAA TGTGTCACCTTCAGC CTGCTCTTCAACTTC GTGTCCTGGATCGCC TTCTTCACCACGGCC 2340
                                              A
           2341            2356            2371            2386            2401            2416
1 T1R1v4 AGCGTCTACGACGGC AAGTACCTGCCTGCG GCCAACATGATGCT GGGCTGAGCAGCCTG AGCAGCGGCTTCGGT GGGTATTTTCTGCCT 1025
2 T1R1v3 AGCGTCTACGACGGC AAGTACCTGCCTGCG GCCAACATGATGCT GGGCTGAGCAGCCTG AGCAGCGGCTTCGGT GGGTATTTTCTGCCT 1668
3 T1R1v1 AGCGTCTACGACGGC AAGTACCTGCCTGCG GCCAACATGATGCT GGGCTGAGCAGCCTG AGCAGCGGCTTCGGT GGGTATTTTCTGCCT 2096
4 T1R1v2 AGCGTCTACGACGGC AAGTACCTGCCTGCG GCCAACATGATGGCT GGGCTGAGCAGCCTG AGCAGCGGCTTCGGT GGGTATTTTCTGCCT 2430
                                                    A
           2431            2446            2461            2476            2491            2506
1 T1R1v4 AAGTGCTACGTGATC CTCTGCCGCCCAGAC CTCAACAGCACAGAG CACTTCCAGGCCCTC ATTCAGGACTACACG AGGCGCTGCGGCTCC 1115
2 T1R1v3 AAGTGCTACGTGATC CTCTGCCGCCCAGAC CTCAACAGCACAGAG CACTTCCAGGCCCTC ATTCAGGACTACACG AGGCGCTGCGGCTCC 1758
3 T1R1v1 AAGTGCTACGTGATC CTCTGCCGCCCAGAC CTCAACAGCACAGAG CACTTCCAGGCCCTC ATTCAGGACTACACG AGGCGCTGCGGCTCC 2186
4 T1R1v2 AAGTGCTACGTGATC CTCTGCCGCCCAGAC CTCAACAGCACAGAG CACTTCCAGGCCCTC ATTCAGGACTACACG AGGCGCTGCGGCTCC 2520

2521            2536            2551            2566            2581            2596
1 T1R1v4 ACCTGACCAGTGGGT CAGCAGGCACGGCTG GCAGCCTTCTCTCGC CTGAGGGTCGAAGGT CGAGCAGGCCGGGGG TGTCCGGGAGGTCTT 1205
2 T1R1v3 ACCTGACCAGTGGGT CAGCAGGCACGGCTG GCAGCCTTCTCTCGC CTGAGGGTCGAAGGT CGAGCAGGCCGGGGG TGTCCGGGAGGTCTT 1848
3 T1R1v1 ACCTGACCAGTGGGT CAGCAGGCACGGCTG GCAGCCTTCTCTCGC CTGAGGGTCGAAGGT CGAGCAGGCCGGGGG TGTCCGGGAGGTCTT 2276
4 T1R1v2 ACCTGACCAGTGGGT CAGCAGGCACGGCTG GCAGCCTTCTCTGCC CTGAGGGTCGAAGGT CGAGCAGGCCGGGGG TGTCCGGGAGGTCTT 2610

2611            2626            2641            2656            2671            2686
1 T1R1v4 TGGGCATCGCGGTCT GGGGTTGGACGTGT AAGCGCCTGGGAGAG CCTAGACCAGGCTCC GGGCTGCCAATAAAG AAGTGAAATGCGTAA 1295
2 T1R1v3 TGGGCATCGCGGTCT GGGGTTGGACGTGT AAGCGCCTGGGAGAG CCTAGACCAGGCTCC GGGCTGCCAATAAAG AAGTGAAATGCGTAA 1938
3 T1R1v1 TGGGCATCGCGGTCT GGGGTTGGACGTGT AAGCGCCTGGGAGAG CCTAGACCAGGCTCC GGGCTGCCAATAAAG AAGTGAAATGCGTAA 2366
4 T1R1v2 TGGGCATCGCGGTCT GGGGTTGGACGTGT AAGCGCCTGGGAGAG CCTAGACCAGGCTCC GGGCTGCCAATAAAG AAGTGAAATGCGTAA 2700

2701
1 T1R1v4 AAAAAAA         1302   (CDS 975) NOT IN EMBL
2 T1R1v3 AAAAAAA         1945   (CDS 1764) ENST00000351136
3 T1R1v1 AAAAAAA         2373   (CDS 1443) ENST00000328191
4 T1R1v2 AAAAAAA         2707   (CDS 2526) ENST00000312526
```

Figure 3
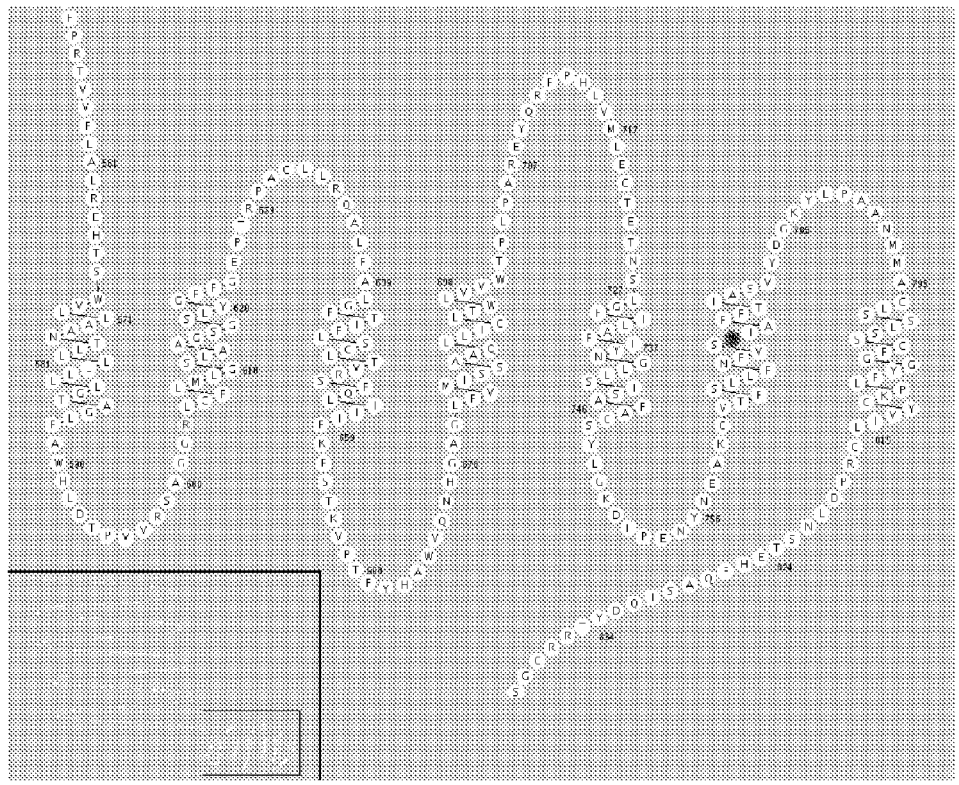
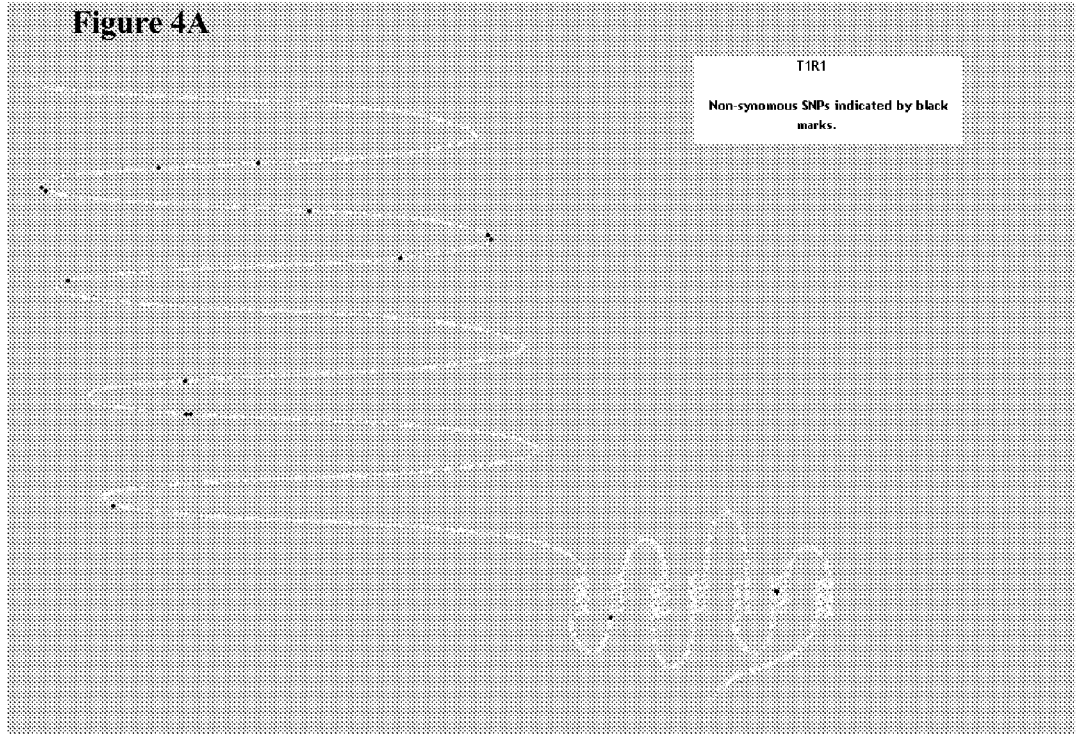

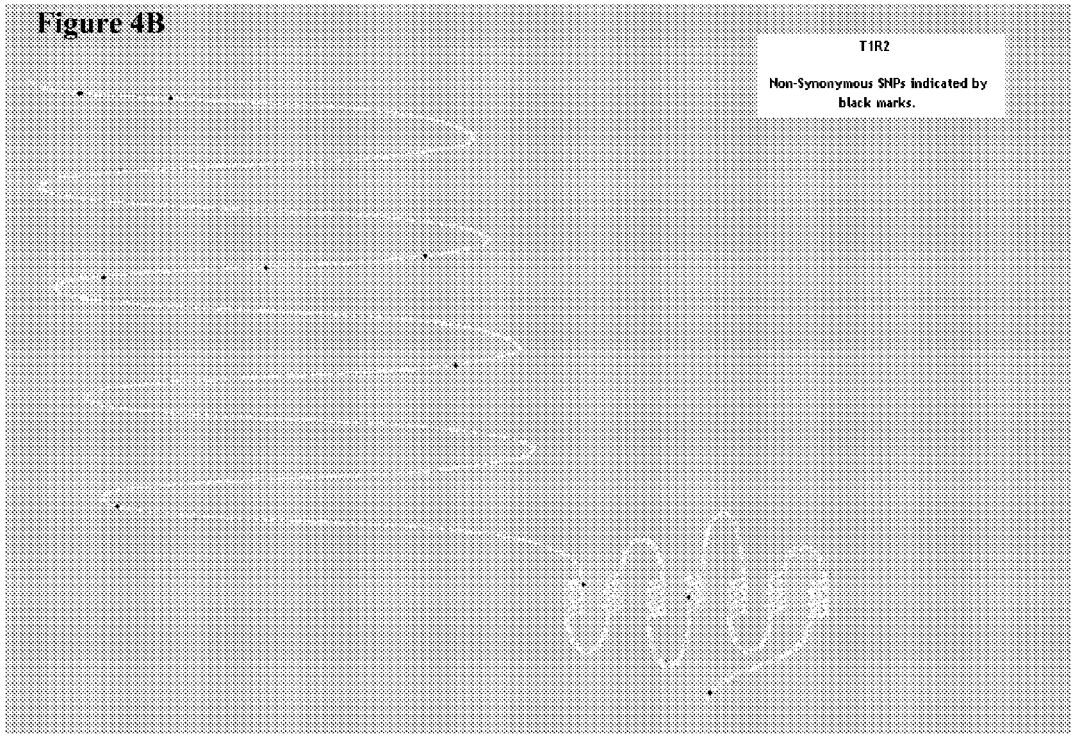
Figure 4B — T1R2 — Non-Synonymous SNPs indicated by black marks.
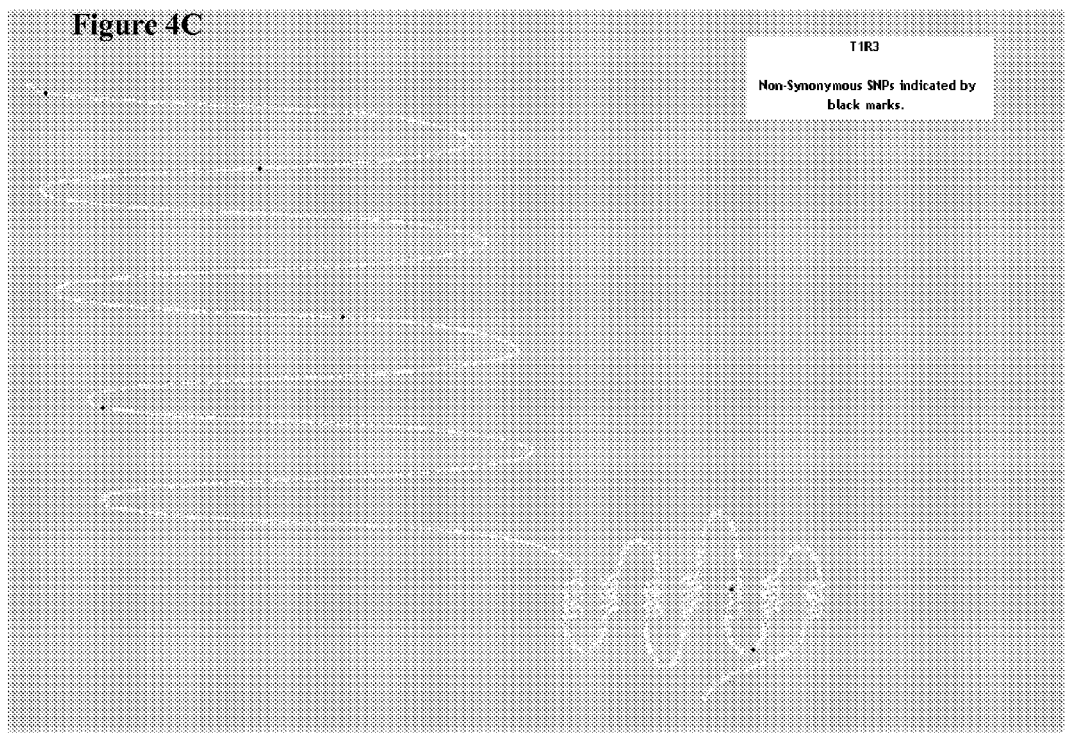
Figure 4C — T1R3 — Non-Synonymous SNPs indicated by black marks.

*TAS1R01*

*TAS1R02*

*TAS1R03*

HUMAN SWEET AND UMAMI TASTE RECEPTOR VARIANTS

CROSS REFERENCE TO RELATED APPLICATIONS

This is the U.S. National Stage of International Application No. PCT/US2006/014045, filed Apr. 13, 2006, which was published in English under PCT Article 21(2), and which in turn claims the benefit of U.S. Provisional Application No. 60/671,173, filed Apr. 13, 2005. Both applications are incorporated herein in their entirety.

FIELD

This disclosure relates to the field of taste reception, and more particularly to variations in taste receptors, such as sweet/umami taste receptors including those in the T1R family. It further relates to methods for identifying individuals and populations having certain taste receptor variants, and identifying compounds that interact with taste receptors, including compounds that interact differentially with different variants of a taste receptor.

BACKGROUND

Sweet and umami (the taste of glutamate) tastes play a major role on the perception of calorically rich and essential nutrients. In humans, three members of the T1R class of taste-specific G protein-coupled receptors (T1R1, T1R2, and T1R3), which reside on chromosome 1, are known to function in combination as heterodimeric receptors for sweet and umami tastes. The T1R proteins each have a large amino-terminal extracellular domain, which is thought to be the site of ligand binding. Unlike the T2R (bitter) taste receptors, T1R proteins are encoded by large genes that span 3 kb to 23 kb in the genome; T1R1 and T1R2 both have six exons, while T1R3 has seven exons.

It is proposed that single nucleotide polymorphisms (SNPs) or variant haplotypes of the T1R genes in humans may underlie individual differences in the perception and recognition threshold for sweeteners and amino acids.

SUMMARY OF THE DISCLOSURE

To enable study of genotype/phenotype correlations for the two tastes sweet and umami, coding sequence variation was identified by sequencing these genes in a cohort of unrelated individuals. To achieve substantial genetic diversity in the sample, sequences were obtained and analyzed from a panel of subjects from several different populations (Cameroonian, Amerindian, Japanese, Chinese, Pakistani, Russian, North European, and Hungarian). In the combined sample, a total of 28 SNPs was found in the three T1R genes. Sixty percent of these SNPs caused an amino acid substitution in the encoded receptor protein, and one SNP, in the T1R1 gene, introduced an in-frame stop codon. These SNPs are shown in FIG. 1, and are reflected in the variations noted in the Sequence Listing.

Although the three T1R sweet/umami taste receptor genes are much larger than the T2R genes that encode bitter taste receptors, the number of cSNPs in the T1R genes is small compared to the number of cSNPs in T2R genes. This suggests that the sequence of the T1R receptor proteins is more conserved than those of T2R receptors, and may explain why individuals show less variation in these taste modalities.

Based on the identification of SNPs in the T1R genes, isolated T1R variant-specific nucleic acid molecules are provided (based on a sequence shown in SEQ ID NO: 1, 3, 5, 7, 9, 11, or 13), each of which comprises at least about 10 contiguous nucleotides that spans at least one SNP identified as new in FIG. 1. Though by no means limited to such use, these molecules are useful in genotyping and haplotyping individuals and populations with regard to their sweet/umami taste receptors.

Also provided herein are isolated T1R isoform polypeptide fragments, each of which comprises an amino acid sequence comprising at least 10 contiguous amino acids corresponding to a sequence shown in SEQ ID NOs: 2, 4, 6, 8, 10, 12 or 14, which fragment includes at least one amino acid variation defined by a cSNP (which alters an amino acid encoded by the nucleic acid SNP) set forth in FIG. 1.

Yet a further embodiment is an isolated nucleic acid molecule comprising a nucleotide sequence for a T1R allele, wherein the nucleotide sequence is selected from a sequence corresponding substantially to SEQ ID NO: 1, 3, or 5, as modified by at least one SNP shown in FIG. 1 (and referred to in the Sequence Listing as variant positions).

There are also provided vectors comprising any of the herein described isolated nucleic acids, as well as host cells comprising such vectors.

The foregoing and other features and advantages will become more apparent from the following detailed description of several embodiments, which proceeds with reference to the accompanying figures.

BRIEF DESCRIPTION OF THE FIGURES

FIG. 1 (FIGS. 1A-1D) is a table showing SNPs identified in the indicated T1R taste receptor genes. CAM: Cameroonian; AME: Amerindian; NOR: North European; JAP: Japanese; RUS: Russian; HUN: Hungarian; CH: Chinese; PAR: Pakistani.

FIG. 2 (FIGS. 2A-2E) is an alignment of isoforms T1R1v4 (SEQ ID NO: 7), T1R1v3 (SEQ ID NO: 9), T1R1v1 (SEQ ID NO: 11), and T1R1v2 (SEQ ID NO: 13) of the T1R1 taste receptor, which isoforms are formed based on differential splicing. Specific SNPs are indicated.

FIG. 3 is a schematic representation of the trans-membrane domain of the T1R1 receptor protein.

FIG. 4 is a series of schematic representations of the T1R1 (FIG. 4A), T1R2 (FIG. 4B), and T1R3 (FIG. 4C) receptor proteins. The positions corresponding to cSNPs in each protein are indicated in black.

SEQUENCE LISTING

Figure 5A:
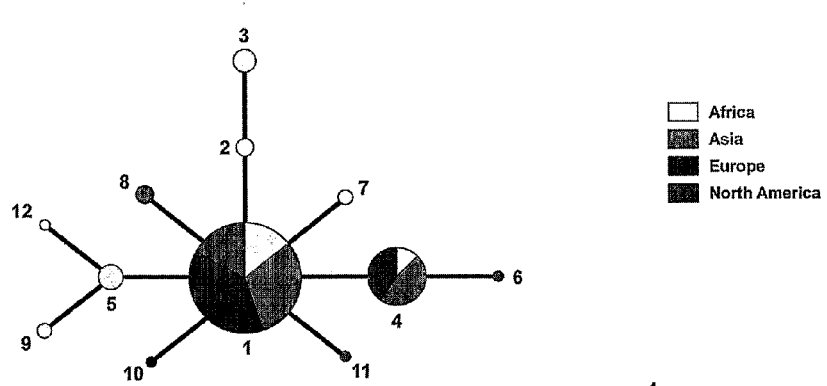
FIG. 5 is a diagram showing minimum haplotype spanning trees for the TAS1R genes. Each circle represents a haplotype, and the size of each circle represents the relative frequency for each haplotype. Within a circle, shading indicates the fraction of observations in the populations indicated. Each connection between haplotypes corresponds to one nucleotide substitution.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 show the nucleotide and amino acid sequence of T1R1. SNPs are indicated as variants, and parallel those shown in FIG. 1.

SEQ ID NOs: 3 and 4 show the nucleotide and amino acid sequence of T1R2. SNPs are indicated as variants, and parallel those shown in FIG. 1.

SEQ ID NOs: 5 and 6 show the nucleotide and amino acid sequence of T1R3. SNPs are indicated as variants, and parallel those shown in FIG. 1.

SEQ ID NOs: 7 and 8 are the nucleotide and amino acid sequence of the T1R1 variant 4.

SEQ ID NOs: 9 and 10 are the nucleotide and amino acid sequence of the T1R1 variant 3.

SEQ ID NOs: 11 and 12 are the nucleotide and amino acid sequence of the T1R1 variant 1.

SEQ ID NOs: 13 and 14 are the nucleotide and amino acid sequence of the T1R1 variant 2.

DETAILED DESCRIPTION

I. Abbreviations

2D-PAGE two-dimensional polyacrylamide gel electrophoresis
ASO allele-specific oligonucleotide
ASOH allele-specific oligonucleotide hybridization
cSNP coding SNP
DASH dynamic allele-specific hybridization
ELISA enzyme-linked immunosorbant assay
HPLC high pressure liquid chromatography
MALDI-TOF matrix-assisted laser desorption/ionization time-of-flight
PCR polymerase chain reaction
RT-PCR reverse-transcription polymerase chain reaction
SNP single nucleotide polymorphism
SSCP single-strand conformation polymorphism II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Addressable: Capable of being reliably and consistently located and identified, as in an addressable location on an array.

Allele: A particular form of a genetic locus, distinguished from other forms by its specific nucleotide sequence.

Amplified RNA (amRNA): A molecule of RNA generated through in vitro transcription, for instance with a T7 or other promoter region attached to the 5' end of the template.

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Array: An arrangement of molecules, particularly biological macromolecules (such as polypeptides or nucleic acids) or biological samples (such as tissue sections) in addressable locations on a substrate, usually a flat substrate such as a membrane, plate or slide. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized to such an extent that it benefits from microscopic examination for evaluation.

Within an array, each arrayed molecule (e.g., oligonucleotide) or sample (more generally, a "feature" of the array) is addressable, in that its location can be reliably and consistently determined within the at least two dimensions on the array surface. Thus, in ordered arrays the location of each feature is usually assigned to a sample at the time when it is spotted onto or otherwise applied to the array surface, and a key may be provided in order to correlate each location with the appropriate feature.

Often, ordered arrays are arranged in a symmetrical grid pattern, but samples could be arranged in other patterns (e.g., in radially distributed lines, spiral lines, or ordered clusters). Arrays are computer readable, in that a computer can be programmed to correlate a particular address on the array with information (such as identification of the arrayed sample and hybridization or binding data, including for instance signal intensity). In some examples of computer readable array formats, the individual spots on the array surface will be arranged regularly, for instance in a Cartesian grid pattern, that can be correlated to address information by a computer.

The sample application spot (or feature) on an array may assume many different shapes. Thus, though the term "spot" is used herein, it refers generally to a localized deposit of nucleic acid or other biomolecule, and is not limited to a round or substantially round region. For instance, substantially square regions of application can be used with arrays, as can be regions that are substantially rectangular (such as a slot blot-type application), or triangular, oval, irregular, and so forth. The shape of the array substrate itself is also immaterial, though it is usually substantially flat and may be rectangular or square in general shape.

Binding or interaction: An association between two substances or molecules, such as the hybridization of one nucleic acid molecule to another (or itself). Disclosed arrays are used to detect binding of, in some embodiments, a labeled nucleic acid molecule (target) to an immobilized nucleic acid molecule (probe) in one or more features of the array. A labeled target molecule "binds" to a nucleic acid molecule in a spot on an array if, after incubation of the (labeled) target molecule (usually in solution or suspension) with or on the array for a period of time (usually 5 minutes or more, for instance 10 minutes, 20 minutes, 30 minutes, 60 minutes, 90 minutes, 120 minutes or more, for instance over night or even 24 hours), a detectable amount of that molecule associates with a nucleic acid feature of the array to such an extent that it is not removed by being washed with a relatively low stringency buffer (e.g., higher salt (such as 3×SSC or higher), room temperature washes). Washing can be carried out, for instance, at room temperature, but other temperatures (either higher or lower) also can be used. Targets will bind probe nucleic acid molecules within different features on the array to different extents, based at least on sequence homology, and the term "bind" encompasses both relatively weak and relatively strong interactions. Thus, some binding will persist after the array is washed in a more stringent buffer (e.g., lower salt (such as about 0.5 to about 1.5×SSC), 55-65° C. washes).

Where the probe and target molecules are both nucleic acids, binding of the test or reference molecule to a feature on the array can be discussed in terms of the specific complementarity between the probe and the target nucleic acids. Also contemplated herein are protein-based arrays, where the probe molecules are or comprise proteins, and/or where the target molecules are or comprise proteins.

cDNA: A DNA molecule lacking internal, non-coding segments (e.g., introns) and regulatory sequences that determine transcription. By way of example, cDNA may be synthesized in the laboratory by reverse transcription from messenger RNA extracted from cells.

DNA (deoxyribonucleic acid): DNA is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

Enriched: The term "enriched" means that the concentration of a material is at least about 2, 5, 10, 100, or 1000 times its natural concentration (for example), advantageously at least 0.01% by weight. Enriched preparations of about 0.5%, 1%, 5%, 10%, and 20% by weight are also contemplated.

EST (Expressed Sequence Tag): A partial DNA or cDNA sequence, typically of between 200 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores are provided in U.S. Pat. No. 5,866,366 to Nazarenko et al., and include for instance: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Examples of fluorophores that are sensitive to ion concentration (such as $Ca^{2+}$ concentration or flux) include, but are not limited to, bis-(1,3-dibutylbarbituric acid)trimethine oxonol (DiBAC4(3) (B-438), Quin-2 (AM Q-1288), Fura-2 (AM F-1225), Indo-1 (AM 1-1226), Fura-3 (AM F-1228), Fluo-3 (AM F-1241), Rhod-2, (AM R-1244), BAPTA (AM B-1205), 5,5'-dimethyl BAPTA (AM D-1207), 4,4'-difluoro BAPTA (AM D-1216), 5,5'-difluoro BAPTA (AM D-1209), 5,5'-dibromo BAPTA (AM D-1213), Calcium Green (C-3011), Calcium Orange (C-3014), Calcium Crimson (C-3017), Fura-5 (F-3023), Fura-Red (F-3020), SBFI (S-1262), PBFI (P-1265), Mag-Fura-2 (AM M-1291), Mag-Indo-1 (AM M-1294), Mag-Quin-2 (AM M-1299), Mag-Quin-1 (AM M-1297), SPQ (M-440), SPA (S-460), Calcien (Fluorescein-bis(methyliminodiacetic acid); Fluorexon), and Quin-2 (2-{[2-Bis-(carboxymethyl)amino-5-methylphenoxy]-methyl}-6-methoxy-8-bis-(carboxymethyl)aminoquinoline tetrapotassium salt). Many of these (and other calcium sensing compounds known to those of ordinary skill) are available, for instance, from Molecular Probes, Invitrogen Detection Technologies, Eugene, Oreg.

Haplotype: The ordered, linear combination of polymorphisms (e.g., SNPs) in the sequence of each form of a gene (on individual chromosomes) that exists in a population.

Haplotyping: Any process for determining one or more haplotypes in an individual. Example methods are described herein, and may include use of family pedigrees, molecular biological techniques, statistical inference, or any combination thereof.

High throughput genomics: Application of genomic or genetic data or analysis techniques that use microarrays or other genomic technologies to rapidly identify large numbers of genes or proteins, or distinguish their structure, expression or function from normal or abnormal cells or tissues, or from cells or tissues of subjects with known or unknown phenotype and/or genotype.

Human Cells: Cells obtained from a member of the species *Homo sapiens*. The cells can be obtained from any source, for example peripheral blood, urine, saliva, tissue biopsy, surgical specimen, amniocentesis samples and autopsy material. From these cells, genomic DNA, mRNA, cDNA, RNA, and/or protein can be isolated.

Hybridization: Nucleic acid molecules that are complementary to each other hybridize by hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA or PNA target. An oligonucleotide need not be 100% complementary to its target nucleic acid sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, for example under physiological conditions in the case of in vivo assays, or under conditions in which the assays are performed.

Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. in *Molecular Cloning: A Laboratory Manual*, Cold Spring Harbor Laboratory Press (1989), chapters 9 and 11, herein incorporated by reference.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isoform: As used herein, the term isoform refers to a protein with a unique amino acid sequence specified by one haplotype of a gene, such as a T1R receptor gene. By way of example, specific examples of T1R isoforms are shown in the sequence listing, SEQ ID NOs: 2, 4, 6, 8, 10, 12, and 14 as well as the variants of these sequences described by the cSNPs listed in FIG. 1.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: Detectable marker or reporter molecules, which can be attached to nucleic acids. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as defined below, but generally refers to the subset of constitutional alterations.

Nucleic acid: A deoxyribonucleotide or ribonucleotide polymer in either single or double stranded form, and unless otherwise limited, encompassing known analogues of natural nucleotides that hybridize to nucleic acids in a manner similar to naturally occurring nucleotides.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA or RNA, of any length suitable for use as a probe or other indicator molecule, and that is informative about the corresponding gene.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear single-stranded polynucleotide sequence ranging in length from 2 to about 5,000 bases, for example a polynucleotide (such as DNA or RNA) which is at least 6 nucleotides, for example at least 10, 12, 15, 18, 20, 25, 50, 100, 200, 1,000, or even 5,000 nucleotides long. Oligonucleotides are often synthetic but can also be produced from naturally occurring polynucleotides.

An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Such analog molecules may also bind to or interact with polypeptides or proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): A series of nucleotide triplets (codons) coding for amino acids without any internal termination codons. These sequences are usually translatable into a peptide.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with compositions provided herein are conventional. By way of example, Martin, in *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stemloop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of taste reception or likely taste reception. It is also appropriate to generate probes and primers based on fragments or portions of these nucleic acid molecules, particularly in order to distinguish between and among different alleles and haplotypes within a single gene. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as any of the sweet/umami taste receptor sequences and specific alleles thereof described herein, for example, by using computer programs intended for that purpose such as PRIMER (Version 0.5, © 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a taste receptor protein encoding nucleotide will anneal to a target sequence, such as homolog of a designated taste receptor protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a taste receptor gene.

Also provided are isolated nucleic acid molecules that comprise specified lengths of taste receptor-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a specified nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Another mode of division, provided by way of example, is to divide a taste receptor sequence based on the regions of the sequence that are relatively more or less homologous to other sweet/umami taste receptor sequences.

Nucleic acid molecules may be selected that comprise at least 10, 15, 20, 25, 30, 35, 40, 50, 100, 150, 200, 250, 300 or more consecutive nucleotides of any of these or other portions of a taste receptor nucleic acid molecule or a specific allele thereof, such as those disclosed herein. Thus, representative nucleic acid molecules might comprise at least 10 consecutive nucleotides of the taste receptor nucleic acid coding sequence shown in any one of SEQ ID NOs: 1, 3, 5, 7, 9, 11, or 13, as modified to include one or more of the SNPs indicated in FIG. 1. More particularly, probes and primers in some embodiments are selected so that they overlap (e.g., include) or reside adjacent to at least one of the indicated SNPs indicated in the Sequence Listing or in FIG. 1.

Purified: The term purified does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

RNA: A typically linear polymer of ribonucleic acid monomers, linked by phosphodiester bonds. Naturally occurring RNA molecules fall into three classes, messenger (mRNA, which encodes proteins), ribosomal (rRNA, components of ribosomes), and transfer (tRNA, molecules responsible for transferring amino acid monomers to the ribosome during protein synthesis). Total RNA refers to a heterogeneous mixture of all three types of RNA molecules.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of nucleic acid or amino acid sequences will possess a relatively high degree of sequence identity when aligned using standard methods. This homology will be more significant when the orthologous proteins or nucleic acids are derived from species which are more closely related (e.g., human and chimpanzee sequences), compared to species more distantly related (e.g., human and *C. elegans* sequences). Typically, orthologs are at least 50% identical at the nucleotide level and at least 50% identical at the amino acid level when comparing human orthologous sequences.

Methods of alignment of sequences for comparison are well known. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. Biosci.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx. Each of these sources also provides a description of how to determine sequence identity using this program.

Homologous sequences are typically characterized by possession of at least 60%, 70%, 75%, 80%, 90%, 91%, 92%, 93%, 94%, 95%, 96%, 97%, or at least 98% or 99% sequence identity counted over the full length alignment with a sequence using the NCBI Blast 2.0, gapped blastp set to default parameters. Queries searched with the blastn program are filtered with DUST (Hancock and Armstrong, *Comput. Appl. Biosci.* 10:67-70, 1994). It will be appreciated that these sequence identity ranges are provided for guidance only; it is entirely possible that strongly significant homologs could be obtained that fall outside of the ranges provided.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that all encode substantially the same protein.

An alternative indication that two nucleic acid molecules are closely related is that the two molecules hybridize to each other under stringent conditions, as described under "specific hybridization."

Single Nucleotide Polymorphism (SNP): A single base (nucleotide) difference in a specific location in the DNA sequence among individuals in a population. A subset of SNPs give rise to changes in the encoded amino acid sequence; these are referred to as coding SNPs, or cSNPs.

Specific binding agent: An agent that binds substantially only to a defined target. Thus a protein-specific binding agent binds substantially only the specified protein. By way of example, as used herein, the term "X-protein specific binding agent" includes anti-X protein antibodies (and functional fragments thereof) and other agents (such as soluble receptors) that bind substantially only to the X protein (where "X" is a specified protein, or in some embodiments a specified domain or form of a protein, such as a particular allelic form of a protein, or a particular isoform).

Anti-X protein antibodies may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-X protein monoclonal antibody, binds substantially only to the X protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Traditional hybridization with a target nucleic acid molecule labeled with [$^{32}$P]-dCTP is generally carried out in a solution of high ionic strength such as 6×SSC at a temperature that is 20-25° C. below the melting temperature, $T_m$, described below. For Southern hybridization experiments where the target DNA molecule on the Southern blot contains 10 ng of DNA or more, hybridization is typically carried out for 6-8 hours using 1-2 ng/ml radiolabeled probe (of specific activity equal to 10$^9$ CPM/μg or greater). Following hybridization, the nitrocellulose filter is washed to remove background hybridization. The washing conditions should be as stringent as possible to remove background hybridization but to retain a specific hybridization signal.

The term $T_m$ represents the temperature (under defined ionic strength, pH and nucleic acid concentration) at which 50% of the probes complementary to the target sequence hybridize to the target sequence at equilibrium. Because the target sequences are generally present in excess, at $T_m$ 50% of the probes are occupied at equilibrium. The $T_m$ of such a hybrid molecule may be estimated from the following equation (Bolton and McCarthy, *Proc. Natl. Acad. Sci. USA* 48:1390, 1962):

$$T_m = 81.5° C. - 16.6(\log_{10}[Na^+]) + 0.41(\% G+C) - 0.63(\% \text{formamide}) - (600/l)$$

where l=the length of the hybrid in base pairs.

This equation is valid for concentrations of Na$^+$ in the range of 0.01 M to 0.4 M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al. (*Molecular Cloning: A Laboratory Manual*, Cold Spring Harbor, N.Y., 1989).

Thus, by way of example, for a 150 base pair DNA probe derived from a cDNA (with a hypothetical % GC of 45%), a calculation of hybridization conditions required to give particular stringencies may be made as follows: For this example, it is assumed that the filter will be washed in 0.3× SSC solution following hybridization, thereby: [Na+]=0.045 M; % GC=45%; Formamide concentration=0; l=150 base pairs; $T_m$=81.5−16.6($\log_{10}$[Na+])+(0.41×45)−(600/150); and so $T_m$=74.4° C.

The $T_m$ of double-stranded DNA decreases by 1-1.5° C. with every 1% decrease in homology (Bonner et al., *J. Mol. Biol.* 81:123, 1973). Therefore, for this given example, washing the filter in 0.3×SSC at 59.4-64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4-68.4° C. will yield a hybridization stringency of 94%; that is, DNA molecules with more than 6% sequence variation relative to the target cDNA molecule will not hybridize. The above example is given entirely by way of theoretical illustration. It will be appreciated that other hybridization techniques may be utilized and that variations in experimental conditions will necessitate alternative calculations for stringency.

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Transcription levels can be quantitated absolutely or relatively. Absolute quantitation can be accomplished by inclusion of known concentrations of one or more target nucleic acids (for example control nucleic acids or with a known amount the target nucleic acids themselves) and referencing the hybridization intensity of unknowns with the known target nucleic acids (for example by generation of a standard curve).

Subject: Living, multicellular vertebrate organisms, a category that includes both human and veterinary subjects for example, mammals, birds and primates.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Single Nucleotide Polymorphisms in T1R Taste Receptor Subunits

The food and beverage industry is one of the world's largest, amounting to trillions of dollars per year. Food and beverage companies tend to operate in highly penetrated, highly competitive markets, and often product sales growth can best be achieved by gaining acceptance from the fraction of the population that perceives a given product as less desirable. For example, approximately 10% of consumers perceive Diet Coke as aversive; they perceive its primary sweetener Aspartame/Nutrasweet as bitter rather than sweet. Overcoming this problem is viewed as the best way to grow the market for this product. Information about sweet and umami taste receptor variants could be used to classify populations, which as shown herein often have very different frequencies of taste receptor variants. This enables generation of population-specific food and beverage products. Taste receptor variants also might be used to better understand the molecular mechanisms of sweet and umami taste, and may facilitate development of improved artificial sweeteners and flavor enhancers.

Described herein are coding sequence polymorphisms in the three human TAS1R genes. The products of these genes are 7 transmembrane domain G protein-coupled receptors (GPCR's) that are expressed on the surface of taste cells of the tongue, that sense sweet taste (as TAS1R2+TAS1R3 dimers) and the taste of umami (exemplified by the taste of monosodium glutamate, MSG, as TAS1R1+TAS1R3 dimers) (Li et al., 2002, Zhao et al., 2003). This variation may account for individual preferences in sweet and umami tastes in foods, and will serve the public health need to better understand and control dietary preferences that lead to obesity and diabetes, which are rapidly growing causes of morbidity and mortality in the population today.

IV. Variants of Human Taste Receptor Genes

The inventors herein have discovered many novel polymorphic sites (polymorphisms, SNPs) in the T1R genes. These SNPs are listed in FIG. 1. The SNPs were identified from a panel of subjects consisting of Cameroonians, Amerindians, Japanese, Chinese, Pakistani, Russians, North Europeans, and Hungarians. Distributions and frequency of SNPs in the various populations are shown herein, for instance in FIG. 1.

Thus, in one embodiment there are provided methods, compositions and kits for genotyping one or more T1R gene(s) in an individual. The genotyping method comprises identifying the nucleotide pair that is present at one or more variant sites selected from the group listed in FIG. 1, in one or both copies of the selected T1R gene(s) from the individual. Examples of such methods further comprise identifying the nucleotide pairs at all (or some subset of) variant sites within any one T1R gene. Also contemplated are methods of genotyping two genes, for instance the two genes involved in detecting sweet taste (T1R2 and T1R3) or umami taste (T1R1 and T1R3), at one or more variant positions as described.

Specific contemplated genotyping compositions comprise an oligonucleotide probe or primer that overlaps (e.g., includes) and is designed to specifically hybridize to a target region containing, or adjacent to, one of the listed T1R SNP sites, for instance specifically one of the SNPs that is referred to in FIG. 1 as newly identified by the inventors. A representative genotyping kit comprises one or more oligonucleotide(s) designed to genotype one or more of the T1R SNP sites. Examples of such kits include at least one oligonucleotide designed to genotype a single T1R gene at all identified SNP sites (which is also useful in haplotyping the individual). Other examples of such kits include at least one oligonucleotide designed to genotype at least one SNP within each of the three T1R genes. One specific example is a kit that comprises at least one oligonucleotide designed to genotype each and every SNP described herein. The provided genotyping methods, compositions, and kits are useful, for instance, for identifying an individual, or collection of individuals, that has one of the genotypes described herein, or a naturally occurring haplotype.

Also provided herein are methods for haplotyping T1R genes, singly or in combination with one or both other T1R genes, in an individual. In examples of such methods, the method comprises determining the identity of the nucleotide at one or more SNP sites (such as those listed in FIG. 1) for one or both copies (also referred to as diplotyping) of the chosen T1R gene(s).

For example, the haplotyping method can be used to validate a specific T1R protein, or isoform (as defined by a given haplotype) as a candidate target for a ligand, such as a sweet or umami tasting compound, or an enhancer, or a blocker, or other compound that interferes with or influences perception of sweet or umami taste perception. Determining for a particular population the frequency of one or more of the individual T1R haplotypes or haplotype pairs will facilitate a decision on whether to pursue it as a target for influencing taste perception, for instance to alter medicine, food or drink preparations, in a way particularly suited to a given population.

If variable T1R activity or tastant binding is associated with perception of (or failure to perceive) a sweet or umami tastant, then one or more T1R variants (e.g., haplotypes or haplotype pairs) is expected to be found at a higher frequency in taster (or non-taster) cohorts than in appropriately genetically matched control individuals. An exemplar situation has been illustrated herein with the T2R38 gene (also referred to as the PTC receptor), as described in patent publications US20040248123A1 and WO05007891A2 (or the equivalent U.S. application corresponding thereto) (both of which are incorporated herein by reference). The practitioner or other individual, without a priori knowledge as to the phenotypic effect of any specific T1R variant(s), haplotype or haplotype pair, can apply the information derived from detecting T1R variants or haplotypes in an individual to decide whether modulating activity of the chosen T1R would be expected to be useful in influencing taste in an individual or a population. Various methods are provided herein for testing whether a compound or ligand interacts with a specific T1R isoform/variant, including ex vivo systems and in vivo systems. Some of these systems measure perceived taste or changes thereto directly; others measure an upstream signal for taste perception, such as for instance release of intracellular calcium based on the activity of the T1R or another protein in the taste perception pathway.

The provided T1R SNPs are also useful in screening for compounds targeting a T1R (or family of T1R) protein to influence a phenotype associated with the T1R isoform, such as perception of a taste such as a sweet or umami taste. For example, detecting which of the T1R variants disclosed herein are present in individual members of a target population will enable the practitioner or other individual to screen for a compound(s) that display the highest desired agonist or antagonist activity for each of the T1R isoforms present in the target population, or the most common isoforms present in the target population. Thus, without requiring any a priori knowledge of the phenotypic effect of any particular T1R variant (or haplotype), the provided analysis methods provide the practitioner or other individual with tools to identify lead compounds that are more likely to show efficacy in influencing taste perception.

The methods for analyzing (e.g., haplotyping) one or more T1R gene(s) in an individual are also useful in the design of trials of candidate compounds for influencing perception of taste, particularly sweet or umami taste, that are predicted to be associated with T1R activity. For example, instead of randomly assigning subjects to the test or control group as is typically done now, determining which T1R variant(s) or haplotype(s) are present in individuals in the study enables one to select the distribution of T1R variants, haplotypes and/or sets of T1R haplotypes to test and control groups, thereby controlling any possible bias in the results that could be introduced by a larger frequency of any one T1R variant, set of variants, haplotype or set of haplotypes that had a previously unknown association with response to the tastant or other ligand being studied. Thus, with the information provided herein, one can more confidently rely on the results of the trial, without needing to first determine the specific phenotypic effect of any T1R variant(s), haplotype or haplotype pair.

Another embodiment provides a method for identifying an association between a trait and a T1R genotype, haplotype, or set of haplotypes for one or more of the T1R genes described herein. The method comprises comparing the frequency of the T1R genotype, haplotype, or set of haplotypes in a population exhibiting the trait (e.g., taste recognition of a compound, or activation of the target T1R isoform) with the frequency of the T1R genotype or haplotype in a reference population. A higher frequency of the T1R genotype, haplotype, or set of haplotypes in the population having the trait than in the reference population indicates the trait is associated with the T1R genotype, haplotype, or set of haplotypes. In examples of such methods, the T1R SNP is selected from a SNP indicated in FIG. 1 as being newly identified by the inventors. Such methods have applicability, for instance, in developing diagnostic tests for taste perception and development and identification of compounds useful for influencing taste, particularly perception of sweet or umami taste, in, for example, a specific target population.

Yet another embodiment is an isolated polynucleotide comprising a nucleotide sequence which is a polymorphic variant (such as an allele) of a reference sequence for a T1R gene, or a fragment thereof, particularly a fragment of 10 or more contiguous nucleotides that overlaps (or includes) a SNP identified herein (e.g., a SNP listed in FIG. 1). The reference sequence for each T1R gene is indicated by GenBank Accession number herein, as follows: T1R1 reference BK000153; T1R2 reference BK000151; T1R3 reference BK000152 (each as available on Apr. 12, 2005). Polymorphisms in T1R genes are indicated in FIG. 1, and those SNPs indicated as new in that figure are particularly relevant. Specifically contemplated herein are isolated nucleic acid molecules that comprise a nucleotide sequence for a T1R variant, wherein the nucleotide sequence is selected from SEQ ID NO: 1, 3, 5, 7, 9, 11, or 13 as modified by any one or more of the SNPs shown in FIG. 1.

Other embodiments provide recombinant expression vectors comprising at least one of the T1R allele variants operably linked to expression regulatory elements, and recombinant host cells transformed or transfected with such an expression vector. The recombinant vector and host cell may be used, for instance, to express a T1R isoform for protein structure analysis and compound binding studies, as discussed more fully herein.

Also provided are T1R polypeptide isoforms, which comprise a polymorphic variant of a reference amino acid sequence for a T1R protein. The reference sequence for each T1R protein is indicated by GenBank Accession number herein, for instance the amino acid sequences are shown in the following Accessions: T1R1 reference BK000153 (as available on Apr. 12, 2005); T1R2 reference BK000151 (as available on Apr. 12, 2005); T1R3 reference BK000152 (as available on Apr. 12, 2005). Example sequences are also shown in SEQ ID NOs: 2, 4, 6, 8, 10, 12, and 14. Polymorphisms in T1R proteins are indicated in FIG. 1, and particularly relevant are those cSNPs indicated as new in that figure, which cause a change in the protein sequence and therefore result in a new T1R isoform. T1R variants are useful in studying the effect of the variation on the biological activity of the T1R, as well as on the binding affinity of candidate compounds (e.g., tastants) targeting T1R for influence perception of sweet and/or umami taste.

Also provided are T1R sequence anthologies, which are collections of T1R alleles or isoforms found in a selected population. The population may be any group of at least two individuals, including but not limited to a reference population, a target population, a geographic population (e.g., based on continent, country, region, and so forth), a family population, a clinical population, and a sex-selected population. A T1R sequence anthology may comprise individual T1R haplotype nucleic acid molecules stored in separate containers such as tubes, separate wells of a microtiter plate and the like. Individual allele nucleic acid molecules or isoforms, or groups of such molecules, in a T1R sequence anthology, may be stored in any convenient and stable form, including but not limited to in buffered solutions, as DNA precipitates, freeze-dried preparations and the like. Also contemplated are anthologies that comprise subsets of T1R sequences, such as a set of all of the variants (for instance, haplotypes or encoded isoforms) for a single T1R gene, or a set of at least one haplotype (or encoded isoform) for each T1R gene, and so forth.

Another embodiment provides specific binding agents, such as antibodies, that recognize and specifically bind to one of the T1R protein variants described herein.

Yet another embodiment is a nonhuman transgenic animal, comprising at least one polymorphic genomic T1R variant allele described herein, as well as methods for producing such animals. The transgenic animals are useful for studying expression of the T1R isoforms in vivo, for screening and testing of compositions targeted against the T1R protein, and for analyzing the effectiveness of agents and compounds for influencing taste, for instance blocking sweet or umami taste, in a biological system.

Yet another embodiment is a computer system for storing and displaying polymorphism, and particularly haplotype, data determined for T1R genes as described herein. A typical computer system includes a computer processing unit, a display, and a database containing the data. Representative T1R polymorphism data includes T1R SNPs (such as those listed in FIG. 1), T1R genotypes, T1R haplotypes, and population or other information about the individuals in one or more populations.

V. Representative Uses of Taste Receptor (e.g., T1R) SNPs and Haplotypes

Identifying receptor-ligand relationships has been difficult and the nature of the ligand that binds to each receptor and initiates taste perception (e.g., sweet, umami, or bitter) is known for only a few receptors. In humans, in vitro studies have shown that the taste receptor T2R16 responds to salicin and other beta-glucopyranosides, and the receptor T2R10 responds to strychnine. Using an alternative human genetic approach has revealed that T2R38 encodes the receptor for phenylthiocarbamide (PTC), a classic variant trait in humans. Distinct phenotypes have been clearly associated only with specific haplotypes of the PTC receptor and there are now five SNPs described corresponding to seven haplotypes, including taster, non-taster and intermediate alleles (see, e.g., PCT/US02/23172, published as WO 03/008627, which is incorporated herein by reference). The non-taster allele may encode an isoform that serves as a functional receptor for another as yet unidentified toxic bitter substance. T2R38 (PTC) studies suggest that there may be substantial additional complexity in identifying specific ligands for each taste receptor, as different alleles of each gene may encode receptors that recognize different ligands.

Identifying in isolation the different DNA variants (SNPs) in a family of taste receptor genes provides a set of variants that could possibly exist in a huge number of different genetically-linked combinations (haplotypes) able to encode a correspondingly huge number of taste receptors expressed on the surface of the tongue. The number of possible proteins increases by $2^N$ as the number (N) of different cSNPs (SNPs able to give rise to changes in amino acid sequence) in the coding sequence of the gene increases, where N is the number of different cSNPs in the coding sequence of the gene.

Thus, the identification of T1R haplotypes based on the SNPs provided herein is valuable because the combination of individual sequence variants (SNPs) that occur together in a system determines the receptor protein produced in a cell. For example, the three variant sites in a single protein are capable of producing eight different protein isoforms, depending on the combination of variant forms present at each of the three sites ($2^3$=eight potential haplotype sequences). In reality, these three sites likely will be found in fewer than the eight possible combinations, in that some possible haplotypes will not exist in any population. This becomes particularly important when a gene contains many coding sequence variants, such as the 17 SNPs that occur in T1R1. These 17 coding SNP's could potentially occur together in over 4000 possible combinations, potentially producing over 130,000 different forms of the T1R1 receptor protein.

It is believed that different T1R haplotypes encode receptor isoforms with different chemical specificities for sweet and/or umami tastants/ligands, analogous to the situation that exists for T2R38 (a bitter taste receptor).

Also reported herein are T1R methods for determining haplotype frequencies in each of several populations, including for instance Europeans, East Asians, and Africans. This information can be used to design foods and beverages for different worldwide markets, in at least two ways. First, in food and beverage research and development, population-specific haplotype distribution information will allow the selection of panels of taste sensors in a rational and efficient manner. This information will also be useful in either pure in vitro systems, or in panels of human volunteer tasters, which can be genotyped or selected using these discoveries. Second, knowledge of the genetic underpinnings in individual taste preferences in target populations will provide powerful predictive information for food and beverage palatability in different populations. Thus population-specific, and indeed even region-specific, anthologies or databases may be developed using this information; these can provide T1R haplotype frequencies in regional or local populations. These resources can be used to improve both development and marketing decisions in the flavorings, food, and beverages industries.

Also provided based on the discoveries described herein are methods and devices for high throughput analysis of T1R genotype and/or phenotype in an individual or group of individuals. A specific example of such a high throughput device is a DNA or protein microarray, which contains a collection of two or more T1R alleles or SNP-specific oligonucleotides (in the case of a DNA microarray) or isoform proteins or variant fragments thereof (in the case of a protein microarray). Examples of such arrays of molecules include at least one molecule representing each of the variants listed in FIG. 1. Specific example arrays include at least two sequences selected from SEQ ID NOs: 1, 3 5, 7, 9, 11, or 13 as modified by any one or more of the SNPs shown in FIG. 1, or an oligonucleotide comprising at least 6 or at least 10 contiguous nucleotides selected from one of these sequences and which oligonucleotide overlaps (or includes) at least one SNP or SNP positions listed in FIG. 1. Other specific example array includes at least five such sequences, at least 10, at least 20, at least 30, at least 50 or more sequences generated by substituting one or more nucleotides of SEQ ID NO: 1, 3, 5, 7, 9, 11, or 13 with one of the SNP variant nucleotides shown in FIG. 1, or an oligonucleotide fragment of each of these sequences, wherein the oligonucleotide includes or overlaps at least one SNP from the sequence.

By way of example, such arrays can be used in genotyping and haplotyping of individuals or groups of individuals. In certain embodiments, the results from such genotyping/haplotyping are used to select a cohort of individuals of known genotype/haplotype for at least one T1R receptor (or a combination of two or more T1R receptors, or all T1R receptors). These individuals could then be trained (as necessary) and used in flavor panel evaluation. Because the population of taste evaluators are of a known (or partially known) genotype as it relates to T1R receptor(s), a relatively small panel of tasters can provide results that can be extrapolated to a large (e.g., commercially relevant) population. Such a large population is beneficially characterized by the frequency of occurrence of specific T1R isoforms/haplotypes, so that panels can be matched to the expected taste preference(s) of the population. The teachings herein enable such methods of extrapolating the sweet/umami taste receptor haplotype from a small group to a large (commercially relevant) population, thus representing a savings in time and cost. Such an approach could be used, for instance, for "deorphanising" T1R receptors for specific sweet and/or umami tastes/tastants or combinations thereof, for evaluating likely population response to tastants or blockers, or to characterize or develop new tastant molecules or blockers. This would allow decisions about population-specific taste variation to aid decisions about worldwide marketing of specific flavorings and food and beverage products.

Also contemplated are in vitro biochemical functional assays of T1R taste receptor function. Such studies employ a variety of different assays, which produce information about G protein activation upon binding of tastant ligands to T1R receptors. One long term goal of such studies is the development of an "artificial tongue" that could be used to perform taste tests without the intervention of living humans as taste sensors.

VI. Representative Ex Vivo Uses of T1R Receptor Haplotype-Specific Isoforms

Haplotypes developed based on the SNP variants described herein can be used to make protein expression constructs and generate unique T1R receptor proteins. These proteins can be arranged in a battery or an array to create a group of sensors for sweet and/or umami tastants ligands, when arrayed in association, for instance, with the correct combination of monomers to form functional (responsive) heterodimers. Such an array could be employed in large parallel high-throughput systems, which would allow the testing of the effects of sweet or umami tastant ligands on all forms of all receptors without the intervention of human tasters.

These expressed isoform receptors can be used in ex vivo reporter assays of several types; it is believed, for instance, that methods useful in examining the T2R receptor activities will similarly be useful in examining activity of T1Rs. One type of assay is exemplified in the publication of Adler et al. *Cell* 100:693, 2000 (incorporated herein by reference in its entirety). The method employs calcium-sensitive dyes to assay the release of calcium from intracellular stores in response to G protein activation by ligand binding to the expressed receptor protein. Another contemplated method employs direct measurement of G protein activation by binding of a radioactive, nonhydrolyzable analog of GTP in a cell-free reconstituted system containing G proteins, T1R receptor (usually both subunits required for forming a heterodimer), and ligand, as described by Sainz et al., *Abstracts of the XXVI Meeting of the Association for Chemoreception Sciences,* 211:55, 2004 (incorporated herein by reference). Either of these systems can be used, for instance in an array-based format, to identify or develop ligands that interact with T1R isoforms or sets of isoforms, or with specific T1R genes, as well as to identify agents that influence the binding of such ligands. For instance, agents that reduce (e.g., block) the binding of a ligand to a specific T1R variant or isoform (or set thereof), or that compete with the binding of a known ligand, can be identified by a reduction in signal in a calcium-sensitive dye system, or by the reduction in binding of the radioactive GTP analog. Agents that increase or enhance the binding of a ligand can be identified by increased signals in either system.

The following examples are provided to illustrate certain particular features and/or embodiments. These examples should not be construed to limit the invention to the particular features or embodiments described.

EXAMPLES

Example 1

Characterization of SNPs in T1R (TAS1R) Taste Receptor Genes

This example provides identification of single nucleotide polymorphisms in the TAS1R1 (T1R1), TAS1R2 (T1R2), and TAS1R3 (T1R3) genes.

Primers were designed to amplify coding regions of each T1R gene. Amplified sequences from individuals from various populations (Cameroonian, N=20; Amerindian, N=10; Japanese, N=10; Chinese, N=10; Pakistani, N=8; Russian, N=10; North European, N=10; and Hungarian, N=10) were sequenced. Single nucleotide polymorphisms, particularly coding SNPs (cSNPs) in the exons of the genes, were identified. These are listed in FIG. 1, and detailed in the Sequence Listing for each of T1R1 (17 SNPs), T1R2 (18 SNPs), and T1R3 (12 SNPs).

Of the 47 cSNPs observed, 29 (60%) cause an amino acid substitution. One introduces an in-frame stop codon in T1R1. The majority (76%) of cSNPs were found in the ~570 amino acid extracellular domain of the T1R proteins (see FIGS. 3 and 4), and the majority of cSNPs showed a minor allele frequency of less than 10% in all populations (FIG. 1).

The genes TAS1R1 and TAS1R3, which encode proteins that act as a dimer to form the umami (glutamate) taste receptor, showed less variation than the TAS1R2 gene, which acts as a dimer with TAS1R3 to form the sweet taste receptor. The TAS1R3 gene, which encodes a subunit common to both the sweet and umami receptors, was the most conserved.

Methods

Population Samples

Human Genomic DNA was obtained from 88 unrelated individuals in eight different geographic populations, including 20 Cameroonians, 10 Northern Europeans, 10 Russians, 8 Pakistani, 10 Hungarians, 10 Native Americans, 10 Chinese, 10 Japanese (N=176 chromosomes). All DNA samples except Cameroonian were purchased from Coriell Cell Repositories.

PCR and DNA Sequencing

SNPs were discovered and assayed by sequencing genomic DNA, with sequence and genotypes assigned after sequencing both strands. Each of the six exons of all three TAS1R genes covering the coding region was amplified with primers designed by software at the Primer3 Web site. PCR was performed in a total volume of 25 µl, containing 0.2 µM of each deoxynucleotide (Invitrogen), 15 pmol of each forward and reverse primers, 1.0-1.5 mM of $MgCl_2$, 10 mM Tris-HCl (pH8.3), 50 mM KCl, 0.75 U of Taq DNA polymerase (PE Biosystems), and 100 ng of genomic DNA. PCR conditions (PE9700, PE Biosystems) were as follows: 35 cycles of denaturation at 94° C. for 30 sec; annealing at 55° C. or 57° C., depending on the primers, for 30 sec; and extension at 72° C. for 1 min. The first step of denaturation and the last step of extension were 95° C. for 2 min and 72° C. for 10 ml, respectively. Five microliters of the PCR products were separated and visualized in a 2% agarose gel. Fifteen microliters of this PCR product were then treated with 0.3 U of shrimp alkaline phosphatase (USB) and 3 U of exonuclease I (USB) at 37° C. for 1 hr, followed by incubation at 80° C. for 15 min. This was diluted with an equal volume of $dH_2O$, and 6 µl was used for the final sequencing reaction. Sequencing reactions were performed in both directions on the PCR products in reactions containing 5 pmol of primer, 1 µl of Big Dye Terminator Ready Reaction Mix (PE Biosystems), and 1 µl of 5× dilution buffer (400 mM Tris-HCl, pH 9 and 10 mM $MgCl_2$). Cycling conditions were 95° C. for 2 min and 35 cycles of 94° C. for 20 sec, 55° C. for 20 sec, and 60° C. for 4 min. Sequencing reaction products were ethanol precipitated, and the pellets were resuspended in 10 µl of formamide loading dye. An ABI 3730 DNA sequencer was used to resolve the products, and data was analyzed by using ABI Sequencing Analysis (v. 5.0) and LASERGENE-SeqMan software.

Inference of Haplotypes

Some haplotypes could be specified from genotypes of individuals, while other haplotypes were inferred. Haplotypes were inferred from unphased genotype data using the PHASE 2.0.2 computer program (Stephens et al., *Am. J. Hum. Genet.* 68:978-89, 2001; Stephens and Donnelly, *Am. J. Hum. Genet.* 73:1162-9, 2003).

Measures of Genetic Diversity

Levels and patterns of genetic diversity in each gene were measured using three statistics: π (the mean pairwise difference between sequences in a population sample), per nucleotide; S (the number of variable nucleotide positions in the sample); and $F_{ST}$ (a measure of population differentiation). $F_{ST}$ values were calculated using the method of Slatkin, treating the major continental regions as populations (Slatkin, *Genet. Res.* 58:167-175, 1991).

Because the TAS1R genes encode protein subunits that interact to form a functional receptor, receptor diversity was also measured from a combinatorial standpoint, taking the different subunits into account. Here, diversity was measured as the expected total difference in amino acid sequence across both subunits, which is estimated by the sum of the mean pairwise amino acid sequence differences within subunits.

Tests of Evolutionary Neutrality

The hypothesis of evolutionary neutrality was tested using Tajima's D statistic, which compares the mean number of nucleotide differences between sequences with the number of variable nucleotide positions in a population sample (Tajima, *Genetics* 123:585-95, 1989). This test was originally designed for use in populations that have remained constant in size. However, several lines of evidence suggest that human population sizes have increased dramatically over the last 100,000 years. Such growth can have strong effects on tests of the D statistic.

Estimates of demographic parameters based on genetic data suggest that human populations have increased at least 100-fold over the last 75,000-100,000 years (Rogers, *Evolution* 49:608-615, 1995; Marth et al., *Proc. Natl. Acad. Sci. U.S.A.* 100:376-81, 1993; Wall and Przeworski, *Genetics* 155:1865-74, 2000). The consensus of these studies is that ancient effective population sizes in humans were small—approximately 10,000. However, estimates of the time and magnitude of growth from that initial size vary substantially. For this reason, the DFSC program (Wooding et al., *Am. J. Hum. Genet.* 74: 637-46, 2004) was used to test the hypothesis of neutrality under a range of population histories. For each gene, Tajima's D test was performed under the assumption that the ancient effective population size in humans was 10,000, with the onset of population expansion ranging from 0 to 200,000 years before present and the magnitude of population expansion ranging from 0- to 500-fold. These were two-tailed tests, where p indicated the probability of observing a smaller value of D, given the population history parameters.

Results

DNA Sequence Variation

Variation in TAS1R genes was identified by sequencing genomic DNA from different individuals. The polymorphisms observed in these genes are shown in FIG. 1. Comparisons of aligned exonic sequences revealed 17 SNPs in TAS1R1 (including 3 synonymous and 14 nonsynonymous variants), 18 SNPs in TAS1R2 (8 synonymous and 10 nonsynonymous), and 12 SNPs in TAS1R3 (6 nonsynonymous and 6 synonymous), for a total of 47 variant nucleotide and 30 variant amino acid sites. Most (64%) of the changes were non-conservative and resulted in variant amino acids encoded at that position.

Examination of the distribution of polymorphisms across the different domains of the protein showed that most (77%) of the variant amino acid positions reside in the large predicted first extracellular domain of these three receptors. This domain is hypothesized to contain the ligand binding site for these receptors (Pin et al., *Pharmacol. Ther.* 98:325-354, 2003). One SNP, which substitutes an A for the normal G at position 2318 in the TAS1R1 cDNA sequence, introduces a premature stop codon.

SNP Population Frequencies

The population frequencies of the TAS1R SNPs are summarized in Table 1. The majority (68%) of the SNPs in the TAS1R genes was observed in only one population, and all of the populations studied had at least one TAS1R SNP that was unique to that population. Only about half (47%) of the population-specific SNPs were uncommon within their population, with a minor allele frequency (MAF) less than 10%.

Only a few SNPs were widely distributed and observed in all populations, one in TAS1R1 and two in TAS1R2.

TABLE 1

Population frequency of SNPs

| Gene | # SNPs that were observed in only one population | # SNPs present in all populations surveyed |
|---|---|---|
| TAS1R1 | 16 | 1 |
| TAS1R2 | 8 | 2 |
| TAS1R3 | 8 | 0 |

TAS1R Gene Haplotypes

Haplotypes were first enumerated by evaluating individuals who were homozygous for all SNPs in each gene, as well as individuals who were heterozygous at a single SNP, allowing explicit determination of two haplotypes. Across the entire sample, the following was explicitly observed: a minimum of 11 haplotypes in TAS1R1, 17 haplotypes in TAS1R2, and 12 haplotypes in TAS1R3. As with the SNPs, African populations revealed the greatest haplotype diversity. Also as with the SNPs, some haplotypes were observed only within one population in the sample, although not all populations showed population-specific haplotypes.

Figure 5B:
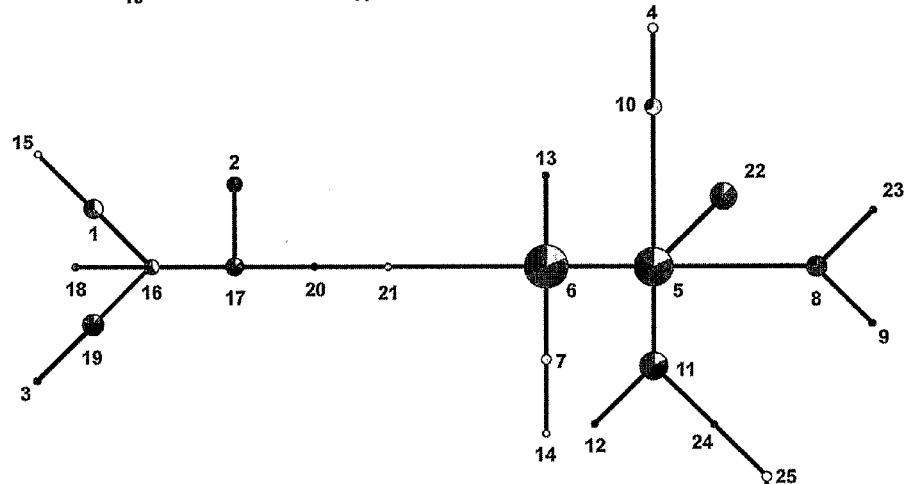
Figure 5C:
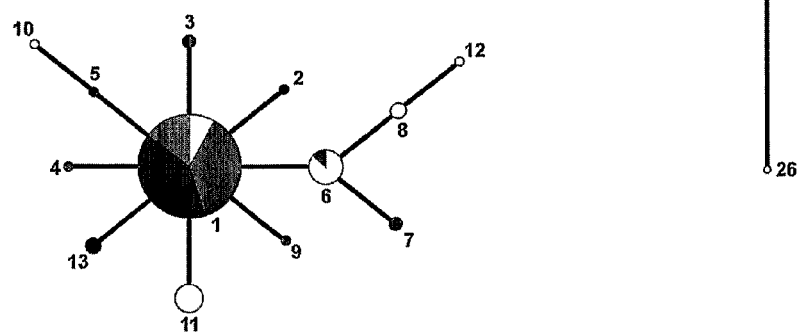

Analysis of all genotypes using PHASE revealed 12 haplotypes in TAS1R1, 26 haplotypes in TAS1R2, and 13 haplotypes in TAS1R3 (see Table 2). Minimum spanning trees were constructed to help visualize putative evolutionary relationships among haplotypes (FIG. 5). Haplotype trees were similar for TAS1R1 and TAS1R3, which were each characterized by a single common haplotype and several rare ones (FIGS. 5A, C). The minimum spanning tree relating TAS1R2 haplotypes was different, characterized by a large number of rare haplotypes, with many found at similar frequencies (FIG. 5B).

TABLE 2

Haplotypes of human TAS1R genes

TAS1R01

```
            Nucleotide position
                    1111122
            22333555570114823
            08278044703114071
            14960115299478848
            snnnnsnnnnnnnnnsn                    Population
HT                                Ca  Ch  Hu  Ja  NA  Eu  Pa  Ru   Total
 1    CACCTTCAAAGGCTGGG           17   9  13  13  20  14  14  19    119
 2    ...............A.            0   0   0   0   0   1   0   0      1
 3    ...............AA.           0   0   0   0   0   1   0   0      1
 4    ...........A.....            1   0   0   0   0   0   0   0      1
 5    ..........A......            3   0   0   0   0   0   0   0      3
 6    ........G..A.....            5   0   0   0   0   0   0   0      5
 7    ......G.........A            4   7   7   7   0   5   1   1     32
 8    ....CC..GC...C...            6   0   0   0   0   0   0   0      6
 9    ...A......A......            0   1   0   0   0   0   0   0      1
10    ..T..............            2   0   0   0   0   0   0   0      2
11    .G.....G.........            0   3   0   0   0   0   0   0      3
12    T........A.A..A.             2   0   0   0   0   0   0   0      2

Total                       40  20  20  20  20  20  16  20    176
      Unique                       6   2   0   0   0   1   1   0     10
```

TAS1R02

```
            Nucleotide position
                 11111222222
                 5678933477001335
                 267308424512691171
                 621402905690522903
                 nnnnnsnssnsnnssssn                Population
HT                                Ca  Ch  Hu  Ja  NA  Eu  Pa  Ru   Total
 1    GCGAAGGGGACGACCCCG           3   0   1   0   0   0   2   2      8
 2    ...............T..           3   0   2   0   7   1   2   3     18
 3    ..........A....T.            0   0   0   0   0   1   0   0      1
 4    .....TC...T......A           1   0   0   0   0   0   0   0      1
 5    ..A..TC...........           1   0   0   0   0   0   0   0      1
 6    ..A..TC........T..           2   0   0   1   1   0   0   1      5
 7    ..A..TC.......T.T..          1   0   0   1   3   2   0   0      7
 8    ..A..TC....A....T.           0   0   0   1   0   0   0   0      1
 9    ..A..TC...T......A           1   0   1   0   2   1   1   3      9
10    ..A..TC..G........           0   0   1   0   0   0   0   0      1
11    ..A..TC..G.....T..           0   0   0   0   0   0   0   1      1
12    ..A.GTC.......T.T..          0   0   2   0   0   1   1   1      5
13    .T................           1   0   0   0   0   0   0   0      1
14    C.................           2   3   3   1   0   4   0   2     15
15    C..............T..           0   0   1   0   0   0   0   0      1
16    C.........A....T.            0   0   0   0   0   1   0   0      1
17    C........G........           0   0   0   0   0   0   1   0      1
18    C......A.G........           2   0   0   0   0   0   0   0      2
19    C.....C........T..           1   0   0   0   0   0   0   0      1
```

TABLE 2-continued

Haplotypes of human TAS1R genes

| HT | | Ca | Ch | Hu | Ja | NA | Eu | Pa | Ru | Total |
|---|---|---|---|---|---|---|---|---|---|---|
| 20 | C....TC........T.. | 0 | 0 | 0 | 0 | 0 | 0 | 1 | 0 | 1 |
| 21 | C.A..TC.......... | 2 | 0 | 0 | 0 | 0 | 0 | 0 | 0 | 2 |
| 22 | C.A..TC....A....T. | 6 | 4 | 1 | 6 | 5 | 3 | 4 | 5 | 34 |
| 23 | C.A..TC....A..T.T. | 8 | 12 | 5 | 6 | 2 | 5 | 3 | 2 | 43 |
| 24 | C.A..TC..G....... | 2 | 0 | 0 | 0 | 0 | 0 | 0 | 0 | 2 |
| 25 | C.AG.TC..G....... | 0 | 1 | 1 | 4 | 0 | 1 | 1 | 0 | 8 |
| 26 | C.AG.TC.A...C..... | 4 | 0 | 2 | 0 | 0 | 0 | 0 | 0 | 6 |
| | Total | 40 | 20 | 20 | 20 | 20 | 20 | 16 | 20 | 176 |
| | Unique | 7 | 0 | 2 | 1 | 0 | 2 | 2 | 1 | 15 |

TAS1R03

Nucleotide position
```
    111111222
    27023379227
    184942617060
    340983297394
    nnnnsssssnns
```

| HT | | Ca | Ch | Hu | Ja | NA | Eu | Pa | Ru | Total |
|---|---|---|---|---|---|---|---|---|---|---|
| 1 | GTGGCGCCCGCC | 11 | 19 | 18 | 16 | 20 | 18 | 15 | 18 | 135 |
| 2 | ...........T | 1 | 0 | 0 | 0 | 0 | 0 | 0 | 0 | 1 |
| 3 | ..........T. | 10 | 0 | 0 | 0 | 0 | 0 | 0 | 0 | 10 |
| 4 | ........T... | 1 | 0 | 0 | 0 | 0 | 0 | 0 | 0 | 1 |
| 5 | ......T..... | 0 | 0 | 1 | 0 | 0 | 2 | 0 | 0 | 3 |
| 6 | ....T....... | 0 | 0 | 0 | 0 | 0 | 0 | 0 | 1 | 1 |
| 7 | ....T..T.... | 0 | 0 | 1 | 0 | 0 | 0 | 1 | 0 | 2 |
| 8 | ....TA...... | 0 | 0 | 0 | 1 | 0 | 0 | 0 | 0 | 1 |
| 9 | ...T........ | 0 | 0 | 0 | 0 | 0 | 0 | 0 | 1 | 1 |
| 10 | ...T..T..... | 13 | 1 | 0 | 1 | 0 | 0 | 0 | 0 | 15 |
| 11 | ..A......A.. | 0 | 0 | 0 | 2 | 0 | 0 | 0 | 0 | 2 |
| 12 | .C..TA...... | 3 | 0 | 0 | 0 | 0 | 0 | 0 | 0 | 3 |
| 13 | A........... | 1 | 0 | 0 | 0 | 0 | 0 | 0 | 0 | 1 |
| | Total | 40 | 20 | 20 | 20 | 20 | 20 | 16 | 20 | 176 |
| | Unique | 5 | 0 | 0 | 2 | 0 | 0 | 0 | 1 | 8 |

Measures of Genetic Diversity

Standard measures of genetic diversity were performed to help determine how the variation found in the TAS1R genes compares to that found in most human genes. The mean pairwise difference between sequences, per nucleotide ($\pi$) was highest in TAS1R02 (2.76 nt/2520 nt=0.110%), followed by TAS1R01 (0.86 nt/2526 ng=0.034%) and TAS1R03 (0.62 nt/2559 nt=0.024%). These values fall within the upper $95^{th}$ and lower $5^{th}$ percentiles of the distribution reported in a genome-wide analysis (Sachidanandam et al., Nature 409: 928-33, 2001), with the value for TAS1R02 being much higher than average and the values for TAS1R01 and TAS1R03 lower than average. Another comparison with values for 3,305 genes (Salisbury et al., Mutat. Res. 526: 53-61, 2003) revealed a similar pattern, with TAS1R02 falling in the top $10^{th}$ percentile and TAS1R01 and TAS1R03 falling in the lower $40^{th}$ and $25^{th}$ percentiles, respectively. Like $\pi$, S was highest in TAS1R02 (n=18), followed by TAS1R01 (n=17) and TAS1R03 (n=12).

$F_{ST}$ values were highest in TAS1R01 ($F_{ST}$=0.160), followed by TAS1R03 ($F_{ST}$=0.068) and TAS1R02 ($F_{ST}$=0.019). Comparisons with the distributions reported for the 3,305 genes by Salisbury et al. (Mutat. Res. 526: 53-61, 2003), along with values reported for ~25,000 SNPs by Akey et al. (Genome Res. 12:1805-14, 2002) revealed that while $F_{ST}$ in TAS1R1 was slightly higher than the average across a large number of genes, $F_{ST}$ was slightly lower than average in TAS1R02 and TAS1R03 which fell in the bottom $35^{th}$ and $20^{th}$ percentiles.

Comparisons across populations revealed that the continental samples studied herein differed substantially with respect to both nucleotide and amino acid diversity (see Table 3). In general, the patterns of diversity in the sample as a whole were reflected in the continental subsamples. For instance, TAS1R2 was the most diverse gene both in the sample as a whole and in each subsample. Among the subsamples, Africa was the most diverse at all three loci. A preponderance of diversity in Africa is common and is generally attributed to a combination of the antiquity and substructuring of African populations (Tishkoff and Verrelli, Ann. Rev. Genomics Hum. Genet. 4:293-340, 2003). Interestingly, while the Native American sample was the least diverse with respect to TAS1R1 and TAS1R3, it was the second most diverse with respect to TAS1R2.

TABLE 3

Nucleotide and amino acid diversity in continental populations

| | Nucleotide | (per nt) | Amino Acid | (per aa) |
|---|---|---|---|---|
| | TAS1R1 | | | |
| Africa | 1.51 | −5.97E−04 | 1.11 | −1.32E−03 |
| Asia | 1.04 | −4.12E−04 | 0.93 | −1.10E−03 |
| Europe | 0.38 | −1.50E−04 | 0.38 | −4.50E−04 |
| N. America | 0 | 0 | 0 | 0 |
| | TAS1R2 | | | |
| Africa | 3.17 | −1.30E−05 | 1.94 | −2.31E−03 |
| Asia | 2.15 | −8.53E−04 | 1.16 | −1.38E−03 |
| Europe | 2.93 | −1.20E−05 | 1.81 | −2.15E−03 |
| N. America | 2.68 | −1.10E−05 | 1.85 | −2.20E−03 |
| | TAS1R3 | | | |

TABLE 3-continued

Nucleotide and amino acid diversity in continental populations

| | Nucleotide | (per nt) | Amino Acid | (per aa) |
|---|---|---|---|---|
| Africa | 1.65 | −6.45E−04 | 0.92 | −1.07E−03 |
| Asia | 0.27 | −1.06E−04 | 0.04 | −4.68E−05 |
| Europe | 0.19 | −7.40E−05 | 0.13 | −1.50E−05 |
| N. America | 0 | 0 | 0 | 0 |

The combinatorial analysis of diversity confirmed that the majority of variation in the sweet and umami receptors is accounted for by TAS1R1 and TAS1R2, as opposed to TAS1R3, which is more conserved. For example, although the Native American sample was the least diverse with respect to TAS1R3, it was the second most diverse with respect to TAS1R2 and was thus the second most diverse with respect to overall variation in the sweet receptor (TAS1R2+TAS1R3).

Tests of Evolutionary Neutrality

Evolutionary genetic analysis can be used to distinguish genetic variation that has been influenced by natural selection (and thus is biologically functional) from other kinds of variation. Such analyses test for statistically significant deviation from evolutionarily neutral genetic drift. Tests of Tajima's D statistic were used to examine the hypothesis of evolutionary neutrality for the sequence variants observed in the TAS1R genes. The hypothesis was tested under several different models that account for different scenarios of population growth. The hypothesis of evolutionary neutrality of the variation in TAS1R2 was rejected under realistic assumptions about population growth. For example, under the assumption that the human population size increased 100-fold, 100,000 years ago, the hypothesis of evolutionary neutrality was strongly rejected ($p>0.99$). For TAS1R1 and TAS1R3 the results were less striking but still similar. Under slightly larger magnitudes of growth (e.g., 200-fold, 100,000 years ago), the hypothesis of neutrality was rejected for TAS1R1 and TAS1R3 as well, and thus all three observed values of D were significantly greater than expected. It was noted, however, that the comparison of D values in these genes with values calculated for roughly 3,300 genes reported by Salisbury et al. (Sal *Mutat. Res.* 526: 53-61, 2003) suggests that these values fall within the expected range, although the value for TAS1R2 was somewhat higher than average. Such general conclusions regarding evolutionary neutrality using Tajima's D measures may reflect selective sweeps that have occurred commonly in human evolutionary history, and the current Tajima's D measurements indicate such selective sweeps may have occurred in the TAS1R genes.

Discussion

The survey described above revealed significant nucleotide and protein sequence diversity in the TAS1R taste receptor family. This information is important for understanding receptor function, as different haplotypes encode significantly different proteins, and these protein subunits may, in turn, interact to further shape taste perception in human individuals. The different forms of TAS1R2, which encode the sweet-specific component of the receptor, are unusually diverse compared to other human genes. These differences appear unlikely to be evolutionarily neutral, and it is believed that they underlie inter-individual variation in sensitivity to sweet compounds.

The site of amino acid variation in the TAS1R receptor gene family is quite dissimilar from that in the TAS2R bitter receptor gene family (Kim et al., *Human Mutation* 26(3):199-204, 2005). In the TAS2R family, much of the variation occurs in the transmembrane domains, and little exists in the first extracellular domain. Conversely, the TAS1R's carry the majority of amino acid sequence variation in their first extracellular domain. Because TAS1R receptors are thought to bind ligands in their large first extracellular domain, while TAS2R receptors are thought to bind ligands in their transmembrane domains, it is proposed that the amino acid sequence diversity in these receptors is related to their ligand recognition and binding functions.

Among the human TAS1R genes, TAS1R3 reveals a relatively smaller degree of diversity. This gene encodes the subunit that is common to both sweet and umami tastes, and thus is likely constrained by the requirement of maintaining functional interactions with both the TAS1R1 and TAS1R2 receptor proteins. TAS1R1 is intermediate in the number of non-synonymous SNPs, and in the values of $\pi$ and S. TAS1R2 showed high levels of S, the pairwise differences between sequences, placing this level of variation in the top 5-10% of all human genes surveyed, depending on the study used for comparison.

The high levels of diversity observed in TAS1R2, including the presence of eight non-synonymous nucleotide substitutions, is notable. The minimum spanning tree for this gene reveals many different haplotypes that are present at low to moderate frequency (FIG. 5B). This pattern of variation, in conjunction with the rejection of evolutionary neutrality by Tajima's D test, suggests that human sweet taste perception mediated by this gene may have evolved to sense a wide variety of structurally different sweet substances.

Variation in TAS1R genes has recently been compared to variation in TAS2R genes across the phylogenetic spectrum (Shi and Zhang, *Mol Biol Evol* 23(2): 292-300, 2006). That study examined a number of different evolutionary genetic parameters from those examined in the current study, and concluded that variation in the TAS1R gene family has been under positive natural selection. Their conclusion is in agreement with the results presented herein, and supports our observation that the variants are functionally significant in taste perception.

Whatever the role of selection, the prevalence of amino acid variation in the TAS1R genes focuses interest on the patterns of phenotypic variance that might be associated with these variants. Although heritable inter-strain differences in sweet taste sensitivity have been documented in mice (Reed et al., *J Neurosci* 24(4):938-946, 2004), little was previously known about heritable inter-individual variation of sweet sensitivity in humans. The few surveys reported to date indicate thresholds to sugars exhibit variability in the population (Blakeslee & Salmon, *Proc Natl Acad Sci USA* 21:84-90, 1935), although no systematic surveys across different racial or ethnic groups have been reported. The findings reported herein suggest that substantial amino acid variation is present in all three TAS1R genes. Variation in these genes is localized to domains believed to be involved in ligand binding. Further, this variation is not distributed uniformly among human populations. Given these findings, it is predicted that (i) human populations will harbor more heritable variation in sweet-taste sensitivity than in umami-taste sensitivity; (ii) human populations will differ appreciably in heritable variation, with Africans being most diverse; and (iii) TAS1R3, while less than diverse than other TAS1R genes, may be an important source of covariance in sweet and umami sensitivity by virtue of the fact that it harbors amino acid substitutions that could affect both phenotypes.

As stated above, variation in TAS1R genes has recently been compared to variation in TAS2R genes across the phylogenetic spectrum (Shi and Zhang, *Mol Biol Evol* 23(2): 292-300, 2006). Although that study took a somewhat different approach and examined a number of different evolutionary genetic parameters from those examined in our study, it concluded that variation in the TAS1R gene family has been under positive natural selection. Taken with the data presented herein, there is now strong evidence that the substantial coding sequence variation observed in the human sweet and umami taste receptors is not random genetic drift, but represents adaptation as a result of selection. This argues strongly that the variants observed are functionally significant in taste perception.

The distribution of TAS1R polymorphisms among human populations may have implications for phenotypic similarities and differences, as well. While TAS1R1 and TAS1R3 have FST values that are near average for a substantial number of genes, FST at TAS1R2 is somewhat lower. The distribution of polymorphisms in these three genes reported herein, which polymorphisms may have effects on sweet and/or umami taste sensitivity, supports the proposal that human populations may be somewhat more homogeneous with respect to sweet taste than with respect to umami taste. This could have implications for diet preferences.

Example 2

Detecting Single Nucleotide Alterations

T1R taste receptor single nucleotide alterations, whether categorized as SNPs or new mutations, can be detected by a variety of techniques in addition to merely sequencing the target sequence. Constitutional single nucleotide alterations can arise either from new germline mutations, or can be inherited from a parent who possesses a SNP or mutation in their own germline DNA. The techniques used in evaluating either somatic or germline single nucleotide alterations include hybridization using allele specific oligonucleotides (ASOs) (Wallace et al., *CSHL Symp. Quant. Biol.* 51:257-261, 1986; Stoneking et al., *Am. J. Hum. Genet.* 48:370-382, 1991), direct DNA sequencing (Church and Gilbert, *Proc. Natl. Acad. Sci. USA* 81:1991-1995, 1988), the use of restriction enzymes (Flavell et al., *Cell* 15:25, 1978; Geever et al., 1981), discrimination on the basis of electrophoretic mobility in gels with denaturing reagent (Myers and Maniatis, Cold Spring Harbor Symp. Quant. Biol. 51:275-284, 1986), RNase protection (Myers et al., *Science* 230:1242, 1985), chemical cleavage (Cotton et al., *Proc. Natl. Acad. Sci. USA* 85:4397-4401, 1985), and the ligase-mediated detection procedure (Landegren et al., *Science* 241:1077, 1988).

Allele-specific oligonucleotide hybridization (ASOH) involves hybridization of probes to the sequence, stringent washing, and signal detection. Other new methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

Oligonucleotides specific to normal or allelic sequences can be chemically synthesized using commercially available machines. These oligonucleotides can then be labeled radioactively with isotopes (such as $^{32}P$) or non-radioactively, with tags such as biotin (Ward and Langer et al., *Proc. Natl. Acad. Sci. USA* 78:6633-6657, 1981), and hybridized to individual DNA samples immobilized on membranes or other solid supports by dot-blot or transfer from gels after electrophoresis. These specific sequences are visualized by methods such as autoradiography or fluorometric (Landegren et al., *Science* 242:229-237, 1989) or colorimetric reactions (Gebeyehu et al., *Nucleic Acids Res.* 15:4513-4534, 1987). Using an ASO specific for a normal allele, the absence of hybridization would indicate a mutation in the particular region of the gene, or a deleted gene. In contrast, if an ASO specific for a mutant allele hybridizes to a sample then that would indicate the presence of a mutation in the region defined by the ASO.

A variety of other techniques can be used to detect the mutations or other variations in DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods. Additional methods include fluorescence polarization methods such as those developed by Pui Kwok and colleagues (see, e.g., Kwok, *Hum. Mutat.*, 19(4):315-23, 2002), microbead methods such as those developed by Mark Chee at Illumina (see, e.g., Oliphant et al., *Biotechniques.* 2002 June; Suppl: 56-8, 60-61, Shen et al., *Genet. Eng. News*, 23(6), 2003), and mass spectrophotometery methods such as those being developed at Sequenom (on the Web at sequenom.com) (see, e.g., Jurinke et al., *Methods Mol Biol.* 187:179-92, 2002; Amexis et al., *Proc Natl Acad Sci USA* 98(21):12097-102, 2001; Jurinke et al., *Adv Biochem Eng Biotechnol.* 2002; 77:57-74; Storm et al., *Meth. Mol. Biol.*, 212:241 262, 2002; Rodi et al., *BioTechniques.*, 32:S62 S69, 2002); U.S. Pat. No. 6,300,076; and WO9820166).

Example 3

Differentiation of Individuals Homozygous Versus Heterozygous for Sequence Variation(s)

Since it is believed that the sequence and/or haplotype of any taste receptor can influence the perception of taste by a subject, it may sometimes be beneficial to determine whether a subject is homozygous or heterozygous for SNPs within any one or more of the T1R taste receptors described herein.

By way of example, the oligonucleotide ligation assay (OLA), as described by Nickerson et al. (*Proc. Natl. Acad. Sci. USA* 87:8923-8927, 1990), allows the differentiation between individuals who are homozygous versus heterozygous for alleles or SNPs indicated in FIG. 1. This feature allows one to rapidly and easily determine whether an individual is homozygous for at least one taste receptor variant, which condition believed to influence taste perception, particularly sweet/umami taste reception, in the individual. Alternatively, OLA can be used to determine whether a subject is homozygous for either of these mutations.

As an example of the OLA assay, when carried out in microtiter plates, one well is used for the determination of the presence of the T1R taste allele in the T1R1 gene that contains an A at nucleotide position 284 (numbering from SEQ ID NO: 1, and as shown in FIG. 1) and a second well is used for the determination of the presence of the T1R taste allele in the same gene that contains a G at that nucleotide position in the alternate allele sequence. Thus, the results for an individual who is heterozygous for the mutation will show a signal in each of the A and G wells.

Example 4

Sweet or Umami Taste Profiles

With the provision herein of specific SNPs within the family of sweet/umami taste receptors, in particular SNPs that can be used to distinguish populations from each other, genetic profiles that provide information on the sweet/umami taste perception and/or regionality of a subject are now enabled. Such profiles are useful in myriad applications, including for instance selecting subjects for inclusion in (or exclusion from) a protocol (such as a taste test), Sweet/umami taste-related genetic profiles comprise the distinct and identifiable pattern of alleles or haplotypes, or sets of alleles or haplotypes, of the SNPs in taste receptor molecules identified herein. The set of taste receptors analyzed in a particular profile will usually include at least one of T1R1, T1R2, and T1R3, but usually two or all three of these receptors. For instance, in the analysis of sweet taste, a profile will usually include T1R2 and T1R3, while a profile of umami taste will usually include T1R1 and T1R3. It is also contemplated that a profile may include both monomers T1R1 and T1R2.

By way of example, any subset of the molecules listed in FIG. 1 (or corresponding to the molecules in these lists) may be included in a single taste profile. Specific examples of such subsets include those molecules that show a SNP that introduces a stop codon (e.g., the variant of T1R1 at position 2318); that show a novel SNP (e.g., those T1R genes with a "new" SNP indicated in FIG. 1); and so forth. Alternatively, gene profiles may be further broken down by the type of taste receptors included in the profile, for instance, those which form the heterodimer that is sensitive to sweet (T1R2 and T1R3) or umami (T1R1 and T1R3), or all of the haplotypes/isoforms of a single T1R gene. Specific contemplated subsets of sequences will include at least one of the following: two or more nucleotides selected from SEQ ID NO: 1, 3, 5, 7, 9, 11, or 13 as modified by one or more of the SNPs listed in FIG. 1, or two or more polypeptides having a sequence selected from SEQ ID NO: 2, 4, 6, 8, 10, 12, or 14 as modified by one or more of the cSNPs listed in FIG. 1; or at least one fragment from each of two or more of such molecules, which fragment overlaps a variant defined in any one or more of the SNPs listed in FIG. 1.

The alleles/haplotypes of each taste receptor included in a specific profile can be determined in any of various known ways, including the specific methods provided herein. One particular contemplated method for detecting and determining the genotype and/or haplotype of multiple taste receptors employs an array of allele-specific oligonucleotides which are used for qualitative and/or quantitative hybridization detection of the presence of specific alleles or SNPs in a sample from a subject.

Optionally, a subject's taste profile can be correlated with one or more appropriate enhancers, inhibitors, or blockers of taste, or other compounds that influence the ability of a subject to perceive a taste, which may be correlated with a control (or set of control) profile(s) condition linked to or associated with, for instance, sensitivity to one or a set of test compounds (such as sweet or umami test compounds). Optionally, the subject's taste profile can be correlated with one or more appropriate treatments, for instance, treatments with compounds that inhibit or enhance the activity of one or more of the taste alleles identified in the profile, or compositions in which the taste of a target component (e.g., sweet or umami) is specifically masked by a blocker (or stimulated by an enhancer) that is added based on the information in the profile.

Example 5

Expression of T1R Taste Receptor Variant Polypeptides

The expression and purification of proteins, such as a T1R taste receptor variant protein, can be performed using standard laboratory techniques, though these techniques are preferentially adapted to be fitted to express the T1R proteins. For instance, if the receptor is to be expressed as a function dimer, the correct pair of subunits (e.g., T1R1 and T1R3 or T1R2 and T1R3) will be co-expressed. Also, for expression under native or near native conditions, where the entire gene is expressed, art-recognized methods can be used to deal with the long genomic size of the T1R genes. By way of example, full genomic clones can be expressed from mammalian artificial chromosomes or extra large payload viral expression vectors.

Additional examples of such method adaptations are discussed or referenced herein. After expression, purified protein may be used for functional analyses, antibody production, diagnostics, and patient therapy. Furthermore, the DNA sequences of the T1R taste receptor variant cDNAs can be manipulated in studies to understand the expression of the gene and the function of its product. Variant or allelic forms of a human T1R taste receptor gene may be isolated based upon information contained herein, and may be studied in order to detect alteration in expression patterns in terms of relative quantities, tissue specificity and functional properties of the encoded T1R taste receptor variant protein (e.g., influence on perception of taste). Partial or full-length cDNA sequences, which encode for the subject protein, may be ligated into bacterial expression vectors. Methods for expressing large amounts of protein from a cloned gene introduced into, for example, *Escherichia coli* (*E. coli*) or baculovirus/Sf9 cells may be utilized for the purification, localization and functional analysis of proteins. For example, fusion proteins consisting of amino terminal peptides encoded by a portion of a gene native to the cell in which the protein is expressed (e.g., a *E. coli* lacZ or trpE gene for bacterial expression) linked to a T1R taste receptor variant protein may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in large amounts for functional studies. Methods and plasmid vectors for producing fusion proteins and intact native proteins in culture are well known in the art, and specific methods are described in Sambrook et al. (In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986).

Fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous cDNA.

For expression in mammalian cells, the cDNA sequence may be ligated to a heterologous promoter, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell. Biol.* 1:486, 1981) or Epstein-Barr (Sugden et al., *Mol. Cell. Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). T1R encoding sequences can also be delivered to target cells in vitro via non-infectious systems, for instance liposomes.

These eukaryotic expression systems can be used for studies of T1R taste receptor variant encoding nucleic acids and mutant forms of these molecules, T1R taste receptor variant proteins and mutant forms of these proteins. The eukaryotic expression systems may also be used to study the function of the normal complete protein, specific portions of the protein, or of naturally occurring or artificially produced mutant proteins.

Using the above techniques, the expression vectors containing a T1R gene sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the T1R taste receptor variant gene or cDNA sequences, for expression in a suitable host. The T1R taste receptor DNA is operatively linked in the vector to an expression control sequence in the recombinant DNA molecule so that a T1R taste receptor polypeptide can be expressed. The expression control sequence may be selected from the group consisting of sequences that control the expression of genes of prokaryotic or eukaryotic cells and their viruses and combinations thereof.

The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant T1R taste receptor DNA sequences, similar systems are employed to express and produce the mutant product. In addition, fragments of a T1R taste receptor protein can be expressed essentially as detailed above. Such fragments include individual T1R taste receptor protein domains or sub-domains, as well as shorter fragments such as peptides. T1R sweet/umami taste receptor protein fragments having therapeutic properties may be expressed in this manner also, including, for instance, substantially soluble fragments.

Example 6

Production of Protein Specific Binding Agents

Monoclonal or polyclonal antibodies may be produced to either a wildtype or reference T1R sweet/umami taste receptor protein or specific allelic forms of these proteins, for instance particular portions that contain a differential amino acid encoded by a SNP and therefore may provide a distinguishing epitope. Optimally, antibodies raised against these proteins or peptides would specifically detect the protein or peptide with which the antibodies are generated. That is, an antibody generated to the specified taste receptor protein or a fragment thereof would recognize and bind that protein and would not substantially recognize or bind to other proteins found in human cells. In some embodiments, an antibody is specific for (or measurably preferentially binds to) an epitope in a variant protein (e.g., an allele of a T1R taste receptor as described herein) versus the reference protein, or vice versa, as discussed more fully herein.

The determination that an antibody specifically detects a target protein or form of the target protein is made by any one of a number of standard immunoassay methods; for instance, the western blotting technique (Sambrook et al., In *Molecular Cloning: A Laboratory Manual*, CSHL, New York, 1989). To determine that a given antibody preparation (such as one produced in a mouse) specifically detects the target protein by western blotting, total cellular protein is extracted from human cells (for example, lymphocytes) and electrophoresed on a sodium dodecyl sulfate-polyacrylamide gel. The proteins are then transferred to a membrane (for example, nitrocellulose) by western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target protein will, by this technique, be shown to bind to the target protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-target protein binding.

Substantially pure T1R taste receptor protein or protein fragment (peptide) suitable for use as an immunogen may be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the target protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against a specific T1R taste receptor protein or peptide (e.g., a peptide that is specific to a variant T1R taste receptor such as those disclosed herein) is to use one or more synthetic peptides synthesized on a commercially available peptide synthesizer based upon the predicted amino acid sequence of the protein or peptide. Polyclonal antibodies can be generated by injecting these peptides into, for instance, rabbits or mice.

D. Antibodies Raised by Injection of Encoding Sequence

Antibodies may be raised against proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356: 152-154, 1992). Expression vectors suitable for this purpose may include those that express the T1R taste receptor-encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the specified protein.

Optionally, antibodies, e.g., sweet/umami taste receptor-specific monoclonal antibodies, can be humanized by methods known in the art. Antibodies with a desired binding specificity can be commercially humanized (Scotgene, Scotland, UK; Oxford Molecular, Palo Alto, Calif.).

E. Antibodies Specific for Specific T1R Taste Receptor Variants

With the provision of several variant T1R taste receptor proteins, the production of antibodies that specifically recognize these protein variants (and peptides derived therefrom) is enabled. In particular, production of antibodies (and fragments and engineered versions thereof) that recognize at least one variant receptor with a higher affinity than they recognize a corresponding wild type T1R taste receptor, or another taste receptor, is beneficial, as the resultant antibodies can be used in analysis, diagnosis and treatment (e.g., inhibition or enhancement of taste perception), as well as in study and examination of the T1R taste receptor proteins themselves.

In particular embodiments, it is beneficial to generate antibodies from a peptide taken from a variation-specific region of the desired T1R sweet/umami taste receptor protein. By way of example, such regions include any peptide (usually four or more amino acids in length) that overlaps with one or more of the SNP-encoded variants described herein. More particularly, it is beneficial to raise antibodies against peptides of four or more contiguous amino acids that overlap the variants identified in FIG. 1, and particularly which comprise at least four contiguous amino acids including the residue(s) indicated in FIG. 1 to be variable in different alleles of the specified T1R putative taste receptors/isoforms.

Longer peptides also can be used, and in some instances will produce a stronger or more reliable immunogenic response. Thus, it is contemplated in some embodiments that more than four amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual mutation identified in each variant. Instead, it is contemplated that variant-specific antibodies also may each recognize an epitope located anywhere throughout the specified T1R taste receptor variant molecule, which epitopes are changed in conformation and/or availability because of the activating mutation. Antibodies directed to any of these variant-specific epitopes are also encompassed herein.

By way of example, the following references provide descriptions of methods for making antibodies specific to mutant proteins: Hills et al., (*Int. J Cancer*, 63: 537-543, 1995); Reiter & Maihle (*Nucleic Acids Res.*, 24: 4050-4056, 1996); Okamoto et al. (*Br. J. Cancer*, 73: 1366-1372, 1996); Nakayashiki et al. (*Jpn. J. Cancer Res.*, 91: 1035-1043, 2000); Gannon et al. (*EMBO J.*, 9: 1595-1602, 1990); Wong et al. (*Cancer Res.*, 46: 6029-6033, 1986); and Carney et al. (*J. Cell Biochem.*, 32: 207-214, 1986). Similar methods can be employed to generate antibodies specific to specific T1R sweet/umami taste receptor variants.

Example 7

Knockout and Overexpression Transgenic Animals

Mutant organisms that under-express or over-express one or more specific alleles (isoforms) of one or more specific taste receptor protein are useful for research. Such mutants allow insight into the physiological and/or psychological role of taste perception in a healthy and/or pathological organism. These "mutants" are "genetically engineered," meaning that information in the form of nucleotides has been transferred into the mutant's genome at a location, or in a combination, in which it would not normally exist. Nucleotides transferred in this way are said to be "non-native." For example, a non-taste receptor promoter inserted upstream of a native taste receptor-encoding sequence would be non-native. An extra copy of a specific taste receptor gene on a plasmid, transformed into a cell, would be non-native.

Mutants may be, for example, produced from mammals, such as mice or rats, that either express, over-express, or under-express a specific allelic variant or haplotype or diplotype of a defined taste receptor (or combination of sweet and/or umami taste receptors), or that do not express a specified receptor (or combination of receptors) at all. Over-expression mutants are made by increasing the number of specified genes in the organism, or by introducing a specific taste receptor allele into the organism under the control of a constitutive or inducible or viral promoter such as the mouse mammary tumor virus (MMTV) promoter or the whey acidic protein (WAP) promoter or the metallothionein promoter. Mutants that under-express a taste receptor, or that do not express a specific allelic variant of a taste receptor, may be made by using an inducible or repressible promoter, or by deleting the taste receptor gene, or by destroying or limiting the function of the taste receptor gene, for instance by disrupting the gene by transposon insertion.

Antisense genes or molecules (such as siRNAs) may be engineered into the organism, under a constitutive or inducible promoter, to decrease or prevent expression of a specific T1R taste receptor, as known to those of ordinary skill in the art.

A mutant mouse over-expressing a heterologous protein (such as a variant T1R sweet/umami taste receptor protein) may be made by constructing a plasmid having a taste receptor allele encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which a specific taste receptor gene is deleted can be made by removing all or some of the coding regions of the gene from embryonic stem cells. Exemplar methods of creating deletion mutations by using a targeting vector have been described (Thomas and Capecchi, *Cell* 51:503-512, 1987).

Example 8

Knock-In Organisms

In addition to knock-out systems, it is also beneficial to generate "knock-ins" that have lost expression of the native protein but have gained expression of a different, usually mutant or identified allelic form of the same protein. By way of example, any one or more of the allelic protein isoforms provided herein (e.g., as shown in SEQ ID NO: 2, 4, 6, 8, 10, 12, or 14 as modified by any one or more of the cSNPs shown in FIG. 1) can be expressed in a knockout background in order to provide model systems for studying the effects of these mutants. In particular embodiments, the resultant knock-in organisms provide systems for studying taste reception, for instance how the taste of specific molecules is perceived.

Those of ordinary skill in the relevant art know methods of producing knock-in organisms. See, for instance, Rane et al. (*Mol. Cell. Biol.*, 22: 644-656, 2002); Sotillo et al. (*EMBO J.*, 20: 6637-6647, 2001); Luo et al. (*Oncogene*, 20: 320-328, 2001); Tomasson et al. (*Blood*, 93: 1707-1714, 1999); Voncken et al. (86: 4603-4611, 1995); Andrae et al. (*Mech. Dev.*, 107: 181-185, 2001); Reinertsen et al. (*Gene Expr.*, 6: 301-314, 1997); Huang et al. (*Mol. Med.*, 5: 129-137, 1999); Reichert et al. (*Blood*, 97: 1399-1403, 2001); and Huettner et al. (*Nat. Genet.*, 24: 57-60, 2000), by way of example.

Example 9

Screening Assays for Compounds that Modulate Taste Receptor Expression or Activity The following assays are designed to identify compounds that interact with (e.g., bind to) a variant form of a T1R sweet/umami taste receptor (including, but not limited to an extracellular domain (ECD) or a cellular domain (CD) or a transmembrane domain (TMD) of a variant T1R taste receptor), a heterodimer formed by the association of two components of a sweet or umami taste receptor complex (e.g., T1R2 and T1R3 or T1R1 and T1R3), compounds that interact with (e.g., bind to) intracellular proteins that interact with a variant form of a T1R taste receptor (including, but not limited to, a TMD or a CD of a variant form of a T1R taste receptor), compounds that interfere with the interaction of a taste receptor with transmembrane or intracellular proteins involved in taste receptor-mediated signal transduction (for instance, but not limited to, compounds that inhibit or otherwise alter association between components in a heterodimer), and to compounds which modulate the activity of a taste receptor gene (i.e., modulate the level of gene expression) or modulate the level of taste receptor activity of a variant form of a T1R taste receptor. Assays may additionally be utilized which identify compounds which bind to taste receptor gene regulatory sequences (e.g., promoter sequences) and which may modulate taste receptor gene expression. See, e.g., Platt, *J Biol Chem* 269:28558-28562, 1994.

The compounds which may be screened in accordance with the invention include, but are not limited to peptides, antibodies and fragments thereof, and other organic compounds (e.g., peptidomimetics, small molecules) that bind to one or more ECDs of a variant T1R taste receptor as described herein and either mimic the activity triggered by the natural ligand (i.e., agonists) or inhibit the activity triggered by the natural ligand (i.e., antagonists); as well as peptides, antibodies or fragments thereof, and other organic compounds that mimic the ECD of a variant T1R taste receptor (or a portion thereof) and bind to and "neutralize" natural ligand.

Such compounds may include, but are not limited to, peptides such as, for example, soluble peptides, including but not limited to members of random peptide libraries; (see, e.g., Lam et al., *Nature* 354:82-84, 1991; Houghten et al., *Nature* 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell* 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds which can be screened in accordance with the invention include but are not limited to small organic molecules that are able to gain entry into an appropriate cell and affect the expression of a variant T1R sweet or umami taste receptor gene or some other gene involved in a taste receptor signal transduction pathway (e.g., by interacting with the regulatory region or transcription factors involved in gene expression); or such compounds that affect the activity of a variant T1R taste receptor or the activity of some other intracellular factor involved in the taste receptor signal transduction pathway.

Computer modeling and searching technologies permit identification of compounds, or the improvement of already identified compounds, that can modulate expression or activity of a variant T1R taste receptor. Having identified such a compound or composition, the active sites or regions are identified. Such active sites might typically be ligand binding sites, such as the interaction domains of a molecule with a variant T1R sweet/umami taste receptor itself, or the interaction domains of a molecule with a specific allelic variant T1R taste receptor isoform in comparison to the interaction domains of that molecule with another isoform of the same or a different T1R taste receptor (to reproduce the effect of an amino acid substitution).

The active site can be identified using methods known in the art including, for example, from the amino acid sequences of peptides, from the nucleotide sequences of nucleic acids, or from study of complexes of the relevant compound or composition with its natural ligand. In the latter case, chemical methods can be used to find the active site by finding where on the factor the complexed ligand is found. Next, the three dimensional geometric structure of the active site may be determined. This can be done by known methods to determine a complete molecular structure. On the other hand, solid or liquid phase NMR can be used to determine certain intramolecular distances. Any other experimental method of structure determination can be used to obtain partial or complete geometric structures, such as high resolution electron microscopy. The geometric structures may be measured with a complexed ligand, natural or artificial, which may increase the accuracy of the active site structure determined. In another embodiment, the structure of the specified taste receptor is compared to that of a "variant" of the specified taste receptor and, rather than solve the entire structure, the structure is solved for the protein domains that are changed.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. Compounds identified by this search are potential variant T1R taste receptor modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

In another embodiment, the structure of a specified allelic taste receptor (the reference form) is compared to that of a variant taste receptor (encoded by a different allele of the same specified receptor). Then, potential sweet/umami taste inhibitors are designed that bring about a structural change in the reference form so that it resembles the variant form. Or, potential sweet/umami taste mimics are designed that bring about a structural change in the variant form so that it resembles another variant form, or the form of the reference receptor.

Further experimental and computer modeling methods useful to identify modulating compounds based upon identification of the active sites of sweet and/or umami compounds, various variants of the T1R taste receptors described herein, and related transduction and transcription factors will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen et al., *Acta Pharmaceutical Fennica* 97:159-166, 1988; Ripka, *New Scientist* 54-57, 1988; McKinaly and Rossmann, *Annu Rev Pharmacol Toxicol* 29:111-122, 1989; Perry and Davies, *OSAR: Quantitative Structure-Activity Relationships in Drug Design* pp. 189-193, 1989 (Alan R. Liss, Inc.); Lewis and Dean, *Proc R Soc Lond* 236:125-140 and 141-162, 1989; and, with respect to a model receptor for nucleic acid components, Askew et al., *J Am Chem Soc* 111:1082-1090, 1989. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of a variant T1R sweet/umami taste receptor gene product, and for designing sweet and/or umami taste blockers, enhancers, and mimics.

Example 10

In Vitro Screening Assays for Compounds that Bind to a Variant T1R Taste Receptor In vitro systems may be designed to identify compounds capable of interacting with (e.g., binding to) a variant T1R taste receptor (including, but not limited to, an ECD, or a TMD, or a CD of a variant T1R taste receptor). Compounds identified may be useful, for example, in modulating the activity of "wild type" and/or "variant" T1R sweet/umami taste receptor gene products; may be useful in elaborating the biological function of taste receptors; may be utilized in screens for identifying compounds that disrupt normal T1R taste receptor interactions; or may in themselves disrupt such interactions.

By way of non-limiting example, screening methods that have been used with T1R proteins are described in U.S. Pat. No. 6,955,887.

The principle of assays used to identify compounds that bind to a variant T1R sweet/umami taste receptor involves preparing a reaction mixture of a variant T1R taste receptor polypeptide and a test compound under conditions and for a time sufficient to allow the two components to interact and bind, thus forming a complex which can be removed and/or detected in the reaction mixture. The variant T1R taste receptor species used can vary depending upon the goal of the screening assay. For example, where agonists or antagonists are sought, the full length variant T1R taste receptor, or a soluble truncated taste receptor, e.g., in which a TMD and/or a CD is deleted from the molecule, a peptide corresponding to an ECD or a fusion protein containing a variant T1R taste receptor ECD fused to a protein or polypeptide that affords advantages in the assay system (e.g., labeling, isolation of the resulting complex, etc.) can be utilized. Where compounds that interact with the cytoplasmic domain are sought to be identified, peptides corresponding to a variant T1R taste receptor CD and fusion proteins containing a variant T1R taste receptor CD can be used.

The screening assays can be conducted in a variety of ways. For example, one method to conduct such an assay would involve anchoring the variant T1R taste receptor protein, polypeptide, peptide or fusion protein or the test substance onto a solid phase and detecting taste receptor/test compound complexes anchored on the solid phase at the end of the reaction. In one embodiment of such a method, the taste receptor reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a variant T1R taste receptor protein, polypeptide, peptide or fusion protein or the test compound to anchor any complexes formed in solution, and a labeled antibody specific for the other component of the possible complex to detect anchored complexes.

Alternatively, cell-based assays, membrane vesicle-based assays and membrane fraction-based assays can be used to identify compounds that interact with a variant T1R sweet/umami taste receptor. To this end, cell lines that express a variant T1R taste receptor (or combination thereof) or cell lines (e.g., COS cells, CHO cells, HEK293 cells, etc.) that have been genetically engineered to express a variant T1R taste receptor (e.g., by transfection or transduction of taste receptor DNA) can be used. Interaction of the test compound with, for example, an ECD or a CD of a variant T1R taste receptor expressed by the host cell can be determined by comparison or competition with a sweet or "umami" compound or analog thereof.

A variant T1R sweet/umami taste receptor polypeptide (such as those described herein) may be employed in a screening process for compounds which bind the receptor and which activate (agonists) or inhibit activation (antagonists) of the receptor polypeptide of the present invention. Thus, polypeptides described herein may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al. *Current Protocols in Immunology* 1 (2): Chapter 5, 1991.

In general, such screening procedures involve providing appropriate cells which express a receptor polypeptide of the present invention on the surface thereof. Such cells include cells from mammals, insects, yeast, and bacteria. In particular, a polynucleotide encoding the receptor of the present invention is employed to transfect cells to thereby express a variant T1R taste receptor. The expressed receptor is then contacted with a test compound to observe binding, stimulation or inhibition of a functional response.

One such screening procedure involves the use of melanophores that are transfected to express a variant T1R taste receptor. Such a screening technique is described in PCT WO 92/01810, published Feb. 6, 1992, and incorporated herein by reference. Such an assay may be employed to screen for a compound which inhibits activation of a receptor of the present invention by contacting the melanophore cells which encode the receptor with both a receptor ligand, such as saccharine or another sweet compound, and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express a variant T1R taste receptor (for example, transfected CHO cells) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a variant T1R sweet/umami taste receptor in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of labeled ligand, such as saccharine or another sweet compound, to cells which have the receptor on the surface thereof, or cell membranes containing the receptor. Such a method involves transfecting a eukaryotic cell with a DNA encoding a variant T1R sweet/umami taste receptor such that the cell expresses the receptor on its surface, or using eukaryotic cells that express the receptor or receptor variant of the present disclosure on their surface. The cell is then contacted with a potential antagonist in the presence of a labeled form of a ligand, such as a sweet or "umami" compound. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand that binds to the receptors. This method is called a binding assay.

Another such screening procedure involves the use of eukaryotic cells, which are transfected to express the receptor of the present invention, or the use of eukaryotic cells that express the receptor of the present invention on their surface. The cells are loaded with an indicator dye that produces a fluorescent signal when bound to calcium, and the cells are contacted with a test substance and a receptor agonist, such as a sweet or umami compound. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another such screening procedure involves use of eukaryotic cells, which are transfected to express the receptor(s) or receptor variant(s) of the present disclosure (or the use of eukaryotic cells that naturally express such receptor(s)), and which are transfected with a reporter gene construct that is coupled to activation of the receptor (for example, luciferase or beta-galactosidase behind an appropriate promoter). The cells are contacted with a test substance and a receptor agonist, such as a sweet or umami compound, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another such screening technique for antagonists or agonists involves introducing RNA encoding a T1R taste receptor into *Xenopus* oocytes to transiently express the receptor. The receptor expressing oocytes are then contacted with a receptor ligand, such as a sweet or umami taste compound, and a compound to be screened. Inhibition or activation of the receptor is then determined by detection of a signal, such as, cAMP, calcium, proton, or other ions.

Another such technique of screening for antagonists or agonists involves determining inhibition or stimulation of T1R taste receptor-mediated cAMP and/or adenylate cyclase accumulation or diminution. Such a method involves transiently or stably transfecting a eukaryotic cell with a variant T1R taste receptor to express the receptor on the cell surface (or using a eukaryotic cell that expresses the receptor of the present invention on its surface). The cell is then exposed to potential antagonists in the presence of ligand, such as a sweet or umami compound. The amount of cAMP accumulation is then measured, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits taste receptor binding, the levels of variant T1R taste receptor-mediated cAMP, or adenylate cyclase activity, will be reduced or increased. Additional techniques for examining the activity of G-protein receptor pathways, and components therein, are known to those of ordinary skill in the art.

Example 11

Assays for Intracellular Proteins that Interact with a Variant T1R Taste Receptor Any method suitable for detecting protein-protein interactions may be employed for identifying transmembrane proteins or intracellular proteins that interact with a variant T1R taste receptor. Among the traditional methods which may be employed are co-immunoprecipitation, crosslinking and co-purification through gradients or chromatographic columns of cell lysates or proteins obtained from cell lysates and a variant T1R taste receptor to identify proteins in the lysate that interact with the PTC taste receptor. For these assays, a variant T1R taste receptor component used can be a full length taste receptor, a soluble derivative lacking the membrane-anchoring region (e.g., a truncated taste receptor in which all TMDs are deleted resulting in a truncated molecule containing ECDs fused to CDs), a peptide corresponding to a CD or a fusion protein containing a CD of a T1R taste receptor.

Once isolated, such an intracellular protein can be identified and can, in turn, be used, in conjunction with standard techniques, to identify proteins with which it interacts. For example, at least a portion of the amino acid sequence of an intracellular protein which interacts with the variant T1R sweet/umami taste receptor can be ascertained using techniques well known to those of skill in the art, such as via the Edman degradation technique. See, e.g., Creighton *Proteins: Structures and Molecular Principles*, W.H. Freeman & Co., N.Y., pp. 34-49, 1983. The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well known. See, e.g., Ausubel et al. *Current Protocols in Molecular Biology* Green Publishing Associates and Wiley Interscience, N.Y., 1989; and Innis et al., eds. *PCR Protocols: A Guide to Methods and Applications* Academic Press, Inc., New York, 1990.

Additionally, methods may be employed which result in the simultaneous identification of genes, which encode the transmembrane or intracellular proteins interacting with a variant T1R taste receptor. These methods include, for example, probing expression libraries, in a manner similar to the well known technique of antibody probing of λgt11 libraries, using labeled taste receptor protein, or a variant T1R taste receptor polypeptide, peptide or fusion protein, e.g., a variant T1R taste receptor polypeptide or taste receptor domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al., *PNAS USA* 88:9578-9582, 1991) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a variant T1R sweet/umami taste receptor nucleotide sequence encoding a variant T1R taste receptor, a variant T1R taste receptor polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, sweet/umami taste receptor may be used as the bait gene product. Total genomic or cDNA sequences are fused to the DNA encoding an activation domain. This library and a plasmid encoding a hybrid of a bait variant T1R/taste receptor gene product fused to the DNA-binding domain are cotransformed into a yeast reporter strain, and the resulting transformants are screened for those that express the reporter gene. For example, and not by way of limitation, a bait variant T1R taste receptor gene sequence, such as the open reading frame of variant T1R taste receptor (or a domain of a taste receptor) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait variant T1R sweet/umami taste receptor gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait taste receptor gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait PTC taste receptor gene product will reconstitute an active GAL4 protein and thereby drive expression of the HIS3 gene. Colonies, which express HIS3, can be detected by their growth on Petri dishes containing semi-solid agar based media lacking histidine. The cDNA can then be purified from these strains, and used to produce and isolate the bait T1R taste receptor gene-interacting protein using techniques routinely practiced in the art.

Example 12

Assays for Compounds that Interfere with Taste Receptor/Intracellular or Taste Receptor/Transmembrane Macromolecule Interaction The macromolecules that interact with a variant T1R sweet/umami taste receptor are referred to, for purposes of this discussion, as "binding partners". These binding partners are likely to be involved in a variant T1R taste receptor signal transduction pathway, and therefore, in the role of taste receptors and taste receptor variants in sweet/umami tasting. Therefore, it is desirable to identify compounds that interfere with or disrupt the interaction of such binding partners with variant and/or normal T1R taste receptors, which may be useful in regulating the activity of variant T1R taste receptors and control the sensitivity to tastes associated with certain taste receptor activity.

The basic principle of the assay systems used to identify compounds that interfere with the interaction between a variant T1R sweet/umami taste receptor and its binding partner or partners involves preparing a reaction mixture containing variant T1R taste receptor protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of a variant T1R taste receptor moiety and its binding partner. Control reaction mixtures are incubated without the test compound or with a placebo. The formation of any complexes between a variant T1R taste receptor moiety and the binding partner is then detected. The formation of a complex in the control reaction, but not in the reaction mixture containing the test compound, indicates that the compound interferes with the interaction of a variant T1R taste receptor and the binding partner. Additionally, complex formation within reaction mixtures containing the test compound and reference T1R taste receptor variant may also be compared to complex formation within reaction mixtures containing the test compound and a different allelic or other variant of the same T1R sweet/umami taste receptor. This comparison may be important in those cases wherein it is desirable to identify compounds that disrupt interactions of reference but not variant T1R taste receptors, or differentially disrupt interactions between different variant T1R taste receptors.

The assay for compounds that interfere with the interaction of a variant T1R taste receptor and binding partners can be conducted in a heterogeneous or homogeneous format. Heterogeneous assays involve anchoring either a variant T1R taste receptor moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with a variant T1R taste receptor moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either a variant T1R sweet/umami taste receptor moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of a variant T1R taste receptor gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of a variant T1R taste receptor moiety and the interactive binding partner is prepared in which either a variant T1R taste receptor or its binding partner is labeled, but the signal generated by the label is quenched due to formation of the complex (see, e.g., U.S. Pat. No. 4,109,496 by Rubenstein, which utilizes this type of approach for immunoassays). The addition of a test substance that competes with and displaces one of the species from the preformed complex will result in the generation of a signal above background. In this way, test substances that disrupt taste receptor/intracellular binding partner interaction can be identified.

In a particular embodiment, a variant T1R taste receptor fusion can be prepared for immobilization. For example, a variant T1R sweet/umami taste receptor or a peptide fragment, e.g., corresponding to a CD, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}I$, for example, by methods routinely practiced in the art. In a heterogeneous assay, e.g., the GST-taste receptor fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between a variant T1R taste receptor gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-taste receptor fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of a variant T1R taste receptor/binding partner interaction can be detected by adding the labeled antibody and measuring the radioactivity associated with the beads.

In another embodiment, these same techniques can be employed using peptide fragments that correspond to the binding domains of a variant T1R sweet/umami taste receptor and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a variant T1R taste receptor gene product can be anchored to a solid material as described above, by making a GST-taste receptor fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-taste receptor fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

Example 13

Assays for Identification of Compounds that Modulate Taste Perception

Compounds, including but not limited to compounds identified via assay techniques such as those described above, can be tested for the ability to modulate sweet and/or umami tastes. The assays described above can identify compounds that affect variant T1R sweet/umami taste receptor activity (e.g., compounds that bind to a variant T1R taste receptor, inhibit binding of the natural ligand, and either activate signal transduction (agonists) or block activation (antagonists), and compounds that bind to a ligand of a variant T1R taste receptor and neutralize ligand activity); or compounds that affect variant T1R taste receptor gene activity (by affecting T1R taste receptor gene expression, including molecules, e.g., proteins or small organic molecules, that affect or interfere with events so that expression of the full length variant or wild-type T1R taste receptor can be modulated). However, it should be noted that the assays described can also identify compounds that modulate variant T1R taste receptor signal transduction (e.g., compounds which affect downstream signaling events, such as inhibitors or enhancers of protein kinases or phosphatase activities which participate in transducing the signal activated by binding of a sweet or umami compound (e.g., saccharine or MSG) to a variant T1R taste receptor). The identification and use of such compounds which affect another step in a variant T1R taste receptor signal transduction pathway in which a variant T1R taste receptor and/or variant T1R taste receptor gene product is involved and, by affecting this same pathway may modulate the effect of variant T1R taste receptor on the sensitivity to tastes are within the scope of the invention. Such compounds can be used as part of a therapeutic method for modulating sweet and/or umami tastes.

Cell-based systems, membrane vesicle-based systems and membrane fraction-based systems can be used to identify compounds that may act to modulate sweet or umami tastes. Such cell systems can include, for example, recombinant or non-recombinant cells, such as cell lines, which express a sweet/umami taste receptor gene or pair of genes (to generate a functional heterodimer. In addition, expression host cells (e.g., COS cells, CHO cells, HEK293 cells) genetically engineered to express a functional variant T1R taste receptor and to respond to activation by the natural ligand, e.g., as measured by a chemical or phenotypic change, induction of another host cell gene, change in ion flux (e.g., $Ca^{2+}$), phosphorylation of host cell proteins, etc., can be used as an end point in the assay.

In utilizing such cell systems, cells may be exposed to a compound suspected of exhibiting an ability to modulate sweet/umami tastes, at a sufficient concentration and for a time sufficient to elicit such a modulation in the exposed cells. After exposure, the cells can be assayed to measure alterations in the expression of a variant T1R sweet/umami taste receptor gene, e.g., by assaying cell lysates for taste receptor mRNA transcripts (e.g., by Northern analysis) or for variant T1R taste receptor protein expressed in the cell; compounds which regulate or modulate expression of a variant T1R taste receptor gene are good candidates as therapeutics. Alternatively, the cells are examined to determine whether one or more cellular phenotypes have been altered to resemble a taster or nontaster type. Still further, the expression and/or activity of components of the signal transduction pathway of which a variant T1R taste receptor is a part, or the activity of a T1R taste receptor signal transduction pathway itself can be assayed.

For example, after exposure, the cell lysates can be assayed for the presence of phosphorylation of host cell proteins, as compared to lysates derived from unexposed control cells. The ability of a test compound to inhibit phosphorylation of host cell proteins in these assay systems indicates that the test compound alters signal transduction initiated by taste receptor activation. The cell lysates can be readily assayed using a Western blot format; i.e., the host cell proteins are resolved by gel electrophoresis, transferred and probed using a detection antibody (e.g., an antibody labeled with a signal generating compound, such as radiolabel, fluor, enzyme, etc.), see, e.g., Glenney et al., *J Immunol Methods* 109:277-285, 1988; Frackelton et al., *Mol Cell Biol* 3:1343-1352, 1983. Alternatively, an ELISA format could be used in which a particular host cell protein involved in the taste receptor signal transduction pathway is immobilized using an anchoring antibody specific for the target host cell protein, and the presence or absence of a phosphorylated residue on the immobilized host cell protein is detected using a labeled antibody. (See, e.g., King et al., *Life Sci* 53:1465-1472, 1993).

In yet another approach, ion flux, such as calcium ion flux, can be measured as an end point for taste receptor stimulated signal transduction. Calcium flux can be measured, for instance, using calcium-sensitive dyes or probes, many of which are known to those of ordinary skill in the art. Examples of ion sensitive fluorophores include, but are not limited to, bis-(1,3-dibutylbarbituric acid)trimethine oxonol (DiBAC4(3) (B-438), Quin-2 (AM Q-1288), Fura-2 (AM F-1225), Indo-1 (AM I-1226), Fura-3 (AM F-1228), Fluo-3 (AM F-1241), Rhod-2, (AM R-1244), BAPTA (AM B-1205), 5,5'-dimethyl BAPTA (AM D-1207), 4,4'-difluoro BAPTA (AM D-1216), 5,5'-difluoro BAPTA (AM D-1209), 5,5'-dibromo BAPTA (AM D-1213), Calcium Green (C-3011), Calcium Orange (C-3014), Calcium Crimson (C-3017), Fura-5 (F-3023), Fura-Red (F-3020), SBFI (S-1262), PBFI (P-1265), Mag-Fura-2 (AM M-1291), Mag-Indo-1 (AM M-1294), Mag-Quin-2 (AM M-1299), Mag-Quin-1 (AM M-1297), SPQ (M-440), SPA (S-460), Calcien (Fluorescein-bis(methyliminodiacetic acid); Fluorexon), and Quin-2 (2-{[2-Bis-(carboxymethyl)amino-5-methylphenoxy]-methyl}-6-methoxy-8-bis-(carboxymethyl)aminoquinoline tetrapotassium salt).

Example 14

Other Assays for Modulators of Variant T1R Taste Receptors

A. Assays for Taste Receptor Protein Activity

T1R sweet/umami taste receptor family members are G-protein coupled receptors that participate in taste transduction, e.g., sweet/umami taste transduction. The activity of a T1R taste receptor protein variants can be assessed using a variety of in vitro and in vivo assays to determine functional, chemical, and physical effects, e.g., measuring ligand binding (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Furthermore, such assays can be used to test for inhibitors and activators of identified T1R taste receptor family member variants. Modulators can also be genetically altered versions of taste receptors. Such modulators of taste transduction activity are useful for customizing taste, for example to modify the detection of sweet and/or umami tastes.

Modulators of a T1R sweet/umami taste receptor protein variant activity are tested using taste receptor polypeptides as described herein, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation is tested using one of the in vitro or in vivo assays described herein. Taste transduction can also be examined in vitro with soluble or solid state reactions, using a full-length taste receptor or a chimeric molecule such as an extracellular domain or transmembrane domain, or combination thereof, of a taste receptor variant covalently linked to a heterologous signal transduction domain, or a heterologous extracellular domain and/or transmembrane domain covalently linked to the transmembrane and/or cytoplasmic domain of a T1R taste receptor protein variant. Furthermore, ligand-binding domains of the protein of interest can be used in vitro in soluble or solid state reactions to assay for ligand binding. In numerous embodiments, a chimeric receptor will be made that comprises all or part of a T1R taste receptor protein variant as well an additional sequence that facilitates the localization of the taste receptor to the membrane, such as a rhodopsin, e.g., an N-terminal fragment of a rhodopsin protein.

Ligand binding of a T1R taste receptor protein variant, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three known subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-C protein complex. In the presence of GTP, release of the known alpha subunit of the G protein from the other two known G protein subunits serves as a criterion of activation.

In an exemplar embodiment, T1R sweet or umami taste receptor protein variant-gustducin interactions are monitored as a function of taste receptor activation. One taste-cell specific G protein that has been identified is called gustducin (McLaughlin et al., *Nature* 357:563-569, 1992). Such ligand dependent coupling of taste receptors with gustducin can be used as a marker to identify modifiers of the T1R taste receptor protein variant.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

In a convenient embodiment, a T1R sweet/umami taste receptor protein variant is expressed in a eukaryotic cell as a chimeric receptor with a heterologous, chaperone sequence that facilitates its maturation and targeting through the secretory pathway. In a preferred embodiment, the heterologous sequence is a rhodopsin sequence, such as an N-terminal leader of a rhodopsin. Such chimeric taste receptors can be expressed in any eukaryotic cell, such as HEK293 cells. Preferably, the cells comprise a functional G protein, e.g., G$\alpha$15, that is capable of coupling the chimeric receptor to an intracellular signaling pathway or to a signaling protein such as phospholipase C$\beta$. Activation of such chimeric receptors in such cells can be detected using any standard method, such as by detecting changes in intracellular calcium by detecting FURA-2 dependent fluorescence in the cell.

An activated G-protein coupled receptor (GPCR) becomes a substrate for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117-127, 1991; Bourne et al., *Nature* 348:125-132, 1990; Pitcher et al., *Annu Rev Biochem* 67:653-692, 1998.

Samples or assays that are treated with a potential T1R taste receptor protein variant inhibitor or activator are compared to control samples without the test compound, to examine the extent of modulation. Such assays may be carried out in the presence of a sweet or umami tastant that is known to activate the particular receptor, and modulation of the sweet/umami-tastant-dependent activation monitored. Control samples (untreated with activators or inhibitors) are assigned a relative T1R sweet/umami taste receptor protein activity value of 100. Inhibition of a T1R taste receptor protein variant is achieved when the T1R taste receptor protein variant activity value relative to the control is about 90%, optionally about 50%, optionally about 25-0%. Activation of a T1R taste receptor protein variant is achieved when the T1R taste receptor protein variant activity value relative to the control is about 110%, optionally about 150%, about 200-500%, or about 1000-2000%.

Changes in ion flux may be assessed by determining changes in polarization (i.e., electrical potential) of the cell or membrane expressing a T1R taste receptor protein variant. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl J Med* 336:1575-1595, 1997). Whole cell currents are conveniently determined using the standard methodology (see, e.g., Hamil et al., *Pflugers Archiv* 391:85, 1981). Other known assays include: radiolabeled ion flux assays and fluorescence assays using voltage-sensitive dyes (see, e.g., Vestergarrd-Bogind et al., *J Membrane Biol* 88:67-75, 1988;

Gonzales & Tsien, *Chem Biol* 4:269-277, 1997; Daniel et al., *J Pharmacol Meth* 25:185-193, 1991; Holevinsky et al., *J Membrane Biology* 137:59-70, 1994). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Convenient assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al. *PNAS USA* 88:10049-10053, 1991). Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine *Nature,* 312:315-321, 1984). IP3 in tam stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *PNAS USA* 88:9868-9872, 1991; and Dhallan et al., *Nature* 347:184-187, 1990). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a convenient embodiment, a T1R sweet or umami taste receptor protein variant activity is measured by expressing a T1R taste receptor protein variant gene in a heterologous cell with a promiscuous G-protein that links the receptor to a phospholipase C signal transduction pathway (see, Offermanns & Simon, *J Biol Chem* 270:15175-15180, 1995). Optionally the cell line is HEK293 (which does not naturally express PTC taste receptor genes) and the promiscuous G-protein is $G\alpha15$ (Offermanns & Simon, *J Biol Chem* 270: 15175-15180, 1995). Modulation of taste transduction is assayed by measuring changes in intracellular $Ca^{2+}$ levels, which change in response to modulation of the a T1R taste receptor protein variant signal transduction pathway via administration of a molecule that associates with a T1R taste receptor protein variant. Changes in $Ca^{2+}$ levels are optionally measured using fluorescent $Ca^{2+}$ indicator dyes and fluorometric imaging. Examples of ion sensitive dyes and probes include, but are not limited to, bis-(1,3-dibutylbarbituric acid) trimethine oxonol (DiBAC4(3) (B-438), Quin-2 (AM Q-1288), Fura-2 (AM F-1225), Indo-1 (AM I-1226), Fura-3 (AM F-1228), Fluo-3 (AM F-1241), Rhod-2, (AM R-1244), BAPTA (AM B-1205), 5,5'-dimethyl BAPTA (AM D-1207), 4,4'-difluoro BAPTA (AM D-1216), 5,5'-difluoro BAPTA (AM D-1209), 5,5'-dibromo BAPTA (AM D-1213), Calcium Green (C-3011), Calcium Orange (C-3014), Calcium Crimson (C-3017), Fura-5 (F-3023), Fura-Red (F-3020), SBFI (S-1262), PBFI (P-1265), Mag-Fura-2 (AM M-1291), Mag-Indo-1 (AM M-1294), Mag-Quin-2 (AM M-1299), Mag-Quin-1 (AM M-1297), SPQ (M-440), SPA (S-460), Calcien (Fluorescein-bis(methyliminodiacetic acid); Fluorexon), and Quin-2 (2-{[2-Bis-(carboxymethyl)amino-5-methylphenoxy]-methyl}-6-methoxy-8-bis-(carboxymethyl)amino-quinoline tetrapotassium salt).

In one embodiment, the changes in intracellular cAMP or cGMP can be measured using immunoassays. The method described in Offermanns & Simon (*J Biol Chem* 270:15175-15180, 1995), for instance, may be used to determine the level of cAMP. Also, the method described in Felley-Bosco et al. (*Am J Resp Cell and Mol Biol* 11:159-164, 1994) may be used to determine the level of cGMP. Further, an assay kit for measuring cAMP and/or cGMP is described in U.S. Pat. No. 4,115,538.

In another embodiment, phosphatidyl inositol (PI) hydrolysis can be analyzed according to U.S. Pat. No. 5,436,128. Briefly, the assay involves labeling of cells with $^3$H-myo-inositol for 48 or more hours. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing a T1R sweet or umami taste receptor protein variant of interest (or containing two T1R proteins, sufficient to form a functional or potentially functional, or variant functional, receptor heterodimer) is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128. The reporter genes can be, e.g., chloramphenicol acetyltransferase, luciferase, β-galactosidase and alkaline phosphatase.

Furthermore, the protein of interest can be used as an indirect reporter via attachment to a second reporter such as green fluorescent protein (see, e.g., Mistili & Spector, *Nature Biotechnology* 15:961-964, 1997).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of a T1R sweet/umami taste receptor family member variant can be any small chemical compound, or a biological entity, such as a protein, sugar, nucleic acid or lipid. Alternatively, modulators can be genetically altered versions of a T1R taste receptor protein gene. Typically, test compounds will be small chemical molecules and peptides. Essentially any chemical compound can be used as a potential modulator or ligand in the assays of the invention, although most often compounds dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one convenient embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particularly chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int J Pept Prot Res* 37:487-493, 1991; and Houghton et al., *Nature* 354:84-88, 1991). Other chemistries for generating chemical diversity libraries can also be used. Such chemistries include, but are not limited to: peptides (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA* 90:6909-6913, 1993), vinylogous polypeptides (Hagihara et al., *J Amer Chem Soc* 114:6568, 1992), nonpeptidal peptidomimetics with glucose scaffolding (Hirschmann et al., *J Amer Chem Soc* 114:9217-9218, 1992), analogous organic syntheses of small compound libraries (Chen et al., *J Amer Chem Soc* 116:2661, 1994), oligocarbamates (Cho et al. 1993 *Science* 261:1303), and/or peptidyl phosphonates (Campbell et al., *J Org Chem* 59:658, 1994), nucleic acid libraries (see Sambrook et al. *Molecular Cloning, A Laboratory Manual*, Cold Springs Harbor Press, N.Y., 1989; and Ausubel et al. *Current Protocols in Molecular Biology* Green Publishing Associates and Wiley Interscience, N.Y., 1989), peptide nucleic acid libraries (see, e.g., U.S. Pat. No. 5,539,083), antibody libraries (see, e.g., Vaughn et al. *Nature Biotechnology* 14:309-314, 1996; and PCT/US96/10287), carbohydrate libraries (see, e.g., Liang et al., *Science* 274:1520-1522, 1996; and U.S. Pat. No. 5,593,853), small organic molecule libraries (see, e.g., benzodiazepines, Baum 1993 C&EN, Jan 18, page 33; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

C. Solid State and Soluble High Throughput Assays

In one embodiment is provided soluble assays using molecules such as a domain such as a ligand binding domain, an extracellular domain, a transmembrane domain, a transmembrane domain and a cytoplasmic domain, an active site, a subunit association region, etc.; a domain that is covalently linked to a heterologous protein to create a chimeric molecule; a T1R sweet/umami taste receptor protein variant/isoform; or a cell or tissue expressing a T1R taste receptor protein variant/isoform, either naturally occurring or recombinant. Another embodiment provides solid phase based in vitro assays in a high throughput format, where the domain, chimeric molecule, T1R taste receptor protein variant/isoform, or cell or tissue expressing a specific T1R taste receptor variant is attached to a solid phase substrate. It is particularly contemplated in some embodiments that multiple molecules are provided in such assays, for instance, a collection of two or more T1R isoforms proteins, or fragments thereof, such as those isoforms shown in SEQ ID NOs: 2, 4, 6, 8, 10, 12, or 14, optionally as modified by one or more of the cSNPs shown in FIG. 1.

In the high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis, Mo.

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, viral receptor ligands, cytokine receptors, chemokine receptors, interleukin receptors, immunoglobulin receptors and antibodies, the cadherein family, the integrin family, the selectin family, and the like; (see, e.g., Pigott & Power 1993 *The Adhesion Molecule Facts Book* 1). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J Am Chem Soc* 85:2149-2154, 1963 (describing solid phase synthesis of, e.g., peptides); Geysen et al., *J Immun Meth* 102:259-274, 1987 (describing synthesis of solid phase components on pins); Frank & Doring, *Tetrahedron* 44:6031-6040, 1988 (describing synthesis of various peptide sequences on cellulose disks); Fodor et al., *Science* 251:767-777, 1991; Sheldon et al., *Clinical Chemistry* 39:718-719, 1993; and Kozal et al., *Nature Medicine* 2:753759, 1996 (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate taste receptor protein activity involves computer assisted drug design, in which a computer system is used to generate a three-dimensional structure of a target taste receptor protein based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a T1R sweet/umami taste receptor polypeptide allelic variant into the computer system. The nucleotide sequence encoding the polypeptide, or the amino acid sequence thereof, can be any of the allelic variant taste receptors described. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Walls potentials. Biological molecules form the structures that minimize the energy terms in a cumulative fashion. The computer program is therefore using these terms encoded by the primary structure or amino acid sequence to create the secondary structural model. An example for G-protein cell receptors is presented in Vaidehi et al. (*PNAS* 99:15308-15312, 2002), which is incorporated herein by reference in its entirety.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been granted, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the target taste receptor protein variant to identify ligands that bind to the protein. Binding affinity between the protein and ligands is determined using energy terms to determine which ligands have an enhanced probability of binding to the protein.

Example 15

Pharmaceutical Preparations and Methods of Administration

Taste modulators can be administered directly to the mammalian subject for modulation of taste, e.g., modulation of sweet or umami taste, in vivo. Administration is by any of the routes normally used for introducing a modulator compound into ultimate contact with the tissue to be treated, optionally the tongue or mouth. The taste modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound in a particular subject.

In determining the effective amounts of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the $LD_{50}$ of the modulator, and the side effects of the inhibitor at various concentrations, as applied to the mass and overall health of the subject. Administration can be accomplished via single or divided doses.

Example 16

Kits

Kits are provided which contain reagents useful for determining the presence or absence of polymorphism(s) in at least one T1R-encoding sequence, such as probes or primers specific for a T1R SNP shown in FIG. 1. Such kits can be used with the methods described herein to determine a subject's T1R genotype or haplotype, for one or more T1R genes.

The provided kits may also include written instructions. The instructions can provide calibration curves or charts to compare with the determined (e.g., experimentally measured) values.

The oligonucleotide probes and primers disclosed herein can be supplied in the form of a kit for use in detection of a specific T1R sequence, such as a SNP or haplotype described herein, in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a T1R polymorphism can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

A kit may include more than two primers, in order to facilitate the in vitro amplification of T1R-encoding sequences, for instance a specific target T1R gene or the 5' or 3' flanking region thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of T1R polymorphism(s) or haplotypes. In certain embodiments, these probes will be specific for a potential polymorphic site that may be present in the target amplified sequences. The appropriate sequences for such a probe will be any sequence that includes one or more of the identified polymorphic sites, particularly those nucleotide positions indicated in FIG. 1, such that the sequence the probe is complementary to a polymorphic site and the surrounding T1R sequence. By way of example, such probes are of at least 6 nucleotides in length, and the polymorphic site occurs at any position within the length of the probe. It is often beneficial to use longer probes, in order to ensure specificity. Thus, in some embodiments, the probe is at least 8, at least 10, at least 12, at least 15, at least 20, at least 30 nucleotides or longer.

It may also be advantageous to provide in the kit one or more control sequences for use in the amplification reactions. The design of appropriate positive control sequences is well known to one of ordinary skill in the appropriate art. By way of example, control sequences may comprise human (or non-human) T1R nucleic acid molecule(s) with known sequence at one or more target SNP positions, such as those described in FIG. 1.

In some embodiments, kits may also include some or all of the reagents necessary to carry out RT-PCR in vitro amplification reactions, including, for instance, RNA sample preparation reagents (including e.g., an RNase inhibitor), appropriate buffers (e.g., polymerase buffer), salts (e.g., magnesium chloride), and deoxyribonucleotides (dNTPs).

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential polymorphism that may be present in the target amplified sequences.

It may also be advantageous to provide in the kit one or more control sequences for use in the RT-PCR reactions. The design of appropriate positive control sequences is well known to one of ordinary skill in the appropriate art.

Kits for the detection or analysis of T1R protein expression (such as over- or under-expression, or expression of a specific isoform) are also encompassed. Such kits may include at least one target protein specific binding agent (e.g., a polyclonal or monoclonal antibody or antibody fragment that specifically recognizes a T1R protein, or beneficially a specific T1R protein isoform) and may include at least one control (such as a determined amount of target T1R protein, or a sample containing a determined amount of T1R protein). The T1R-protein specific binding agent and control may be contained in separate containers.

T1R protein or isoform expression detection kits may also include a means for detecting T1R:binding agent complexes, for instance the agent may be detectably labeled. If the detectable agent is not labeled, it may be detected by second antibodies or protein A for example which may also be provided in some kits in one or more separate containers. Such techniques are well known.

Additional components in specific kits may include instructions for carrying out the assay. Instructions will allow the tester to determine T1R expression level. Reaction vessels and auxiliary reagents such as chromogens, buffers, enzymes, etc. may also be included in the kits.

Also provided are kits that allow differentiation between individuals who are homozygous versus heterozygous for specific SNPs (or haplotypes) of the described T1R taste receptors. Examples of such kits provide the materials necessary to perform oligonucleotide ligation assays (OLA), as described at Nickerson et al. (*Proc. Natl. Acad. Sci. USA* 87:8923-8927, 1990). In specific embodiments, these kits contain one or more microtiter plate assays, designed to detect polymorphism(s) in a T1R sequence of a subject, as described herein.

Additional components in some of these kits may include instructions for carrying out the assay. Instructions will allow the tester to determine whether a specified T1R allele is present, and whether it is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

This disclosure provides a collection of nucleotide variants (single nucleotide polymorphisms) in the sweet and umami taste receptors T1R1, T1R2, and T1R3. The disclosure further provides methods for using the corresponding allelic variants of the taste receptor genes, alone or in various combinations, to test and characterize a subject's sweet and/or umami tasting profile and to identify and analyze compounds that interact with and/or influence such tastes in different subjects and populations. It will be apparent that the precise details of the methods described may be varied or modified without departing from the spirit of the described invention. We claim all such modifications and variations that fall within the scope and spirit of the claims below.

The invention claimed is:

1. An isolated T1R1 variant-specific nucleic acid molecule comprising at least 30 contiguous nucleotides of SEQ ID NO: 1, and including at least one single nucleotide polymorphism (SNP), wherein the at least one SNP comprises T at position 201 of SEQ ID NO: 1, and wherein the T1R1 variant-specific nucleic acid molecule is substantially pure and is attached to a label, wherein the label comprises a fluorophore, a radioactive isotope, a ligand, a chemiluminescent agent, a metal colloid, an enzyme, a co-factor, a hapten or biotin.

2. The isolated nucleic acid molecule of claim 1, which is a nucleotide sequence encoding for a T1R1 allele, and wherein the at least one SNP further comprises at least one SNP selected from the group consisting of: G at position 284; T at position 329; A at position 376; C at position 380; C at position 501; G at position 541; G at position 545; G at position 572; C at position 709; A at position 1114; A position 1117; C at position 1448; A at position 1808; and A at position 2274 of SEQ ID NO: 1.

3. A vector comprising an isolated T1R1 variant-specific nucleic acid molecule comprising at least 30 contiguous nucleotides of SEQ ID NO: 1, and including at least one single nucleotide polymorphism (SNP), wherein the at least one SNP comprises T at position 201 of SEQ ID NO: 1, wherein the vector further comprises a heterologous promoter.

4. The vector of claim 3, wherein the isolated nucleic acid molecule is operably linked to one or more expression regulatory elements.

5. An isolated host cell comprising the vector of claim 3.

6. A kit for genotyping a T1R1 gene, comprising at least one oligonucleotide that specifically hybridizes to a target region containing a T1R1 SNP, wherein the SNP comprises T at position 201 of T1R1 of SEQ ID NO: 1,
wherein the at least one oligonucleotide is at least 30 nucleotides in length and comprises at least 30 contiguous nucleotides that are 100% complementary to the target region containing the SNP, and wherein the at least one oligonucleotide is attached a label or a tag, wherein the label or the tag comprises a fluorophore, a radioactive isotope, a ligand, a chemiluminescent agent, a metal colloid, an enzyme, a co-factor, a hapten or biotin.

7. The kit of claim 6, further comprising a plurality of oligonucleotides, wherein each oligonucleotide specifically hybridizes to a target region containing a T1R1 SNP selected from G at position 284; T at position 329; A at position 376; C at position 380; C at position 501; G at position 541; G at position 545; G at position 572; C at position 709; A at position 1114; A position 1117; C at position 1448; A at position 1808; and A at position 2274 of T1R1 of SEQ ID NO: 1, and wherein the plurality of oligonucleotides comprises at least one oligonucleotide that specifically hybridizes to each target region of the T1R1 gene and wherein each of the at least one oligonucleotides that specifically hybridizes to each target region of the T1R1 gene is attached to a label or a tag, wherein the label or the tag comprises a fluorophore, a radioactive isotope, a ligand, a chemiluminescent agent, a metal colloid, an enzyme, a co-factor, a hapten, or biotin.

8. The kit of claim 6, wherein the kit further comprises one or more reagents for amplifying the target region.

9. The kit of claim 6, wherein the at least one oligonucleotide is at least 50 nucleotides in length.

10. The isolated T1R1 variant-specific nucleic acid molecule of claim 1, comprising at least 35, at least 40, at least 45 or at least 50 contiguous nucleotides of SEQ ID NO: 1 and including T at position 201.

11. A vector comprising an isolated T1R1 variant-specific nucleic acid molecule comprising at least 20 contiguous nucleotides of SEQ ID NO: 1, and including at least one SNP, wherein the at least one SNP comprises T at position 201 of SEQ ID NO: 1, wherein the vector further comprises a heterologous promoter.

12. The vector of claim 11, wherein the isolated nucleic acid molecule is operably linked to one or more expression regulatory elements.

13. An isolated host cell comprising the vector of claim 11.

14. The isolated nucleic acid molecule of claim 1, which is a nucleotide sequence encoding for a T1R1 allele, wherein the nucleotide sequence comprises SEQ ID NO: 1 as modified by T at position 201; G at position 284; T at position 329; A at position 376; C at position 380; C at position 501; G at position 541; G at position 545; G at position 572; C at position 709; A at position 1114; A position 1117; C at position 1448; A at position 1808; and A at position 2274.

15. A vector comprising an isolated nucleic acid molecule encoding for a T1R1 allele, wherein the nucleotide sequence comprises SEQ ID NO: 1 as modified by T at position 201; G at position 284; T at position 329; A at position 376; C at position 380; C at position 501; G at position 541; G at position 545; G at position 572; C at position 709; A at position 1114; A position 1117; C at position 1448; A at position 1808; and A at position 2274; and a heterologous promoter.

16. An isolated host cell comprising the vector of claim 15.

* * * * *

SEQUENCE LISTING

```
<160> NUMBER OF SEQ ID NOS: 14

<210> SEQ ID NO 1
<211> LENGTH: 2526
<212> TYPE: DNA
<213> ORGANISM: Homo sapiens
```

```
<220> FEATURE:
<221> NAME/KEY: CDS
<222> LOCATION: (1)..(2526)
<220> FEATURE:
<221> NAME/KEY: variation
<222> LOCATION: (201)..(201)
<223> OTHER INFORMATION: n = C or T
<220> FEATURE:
<221> NAME/KEY: variation
<222> LOCATION: (284)..(284)
<223> OTHER INFORMATION: n = A or G
<220> FEATURE:
<221> NAME/KEY: variation
<222> LOCATION: (329)..(329)
<223> OTHER INFORMATION: n = C or T
<220> FEATURE:
<221> NAME/KEY: variation
<222> LOCATION: (376)..(376)
<223> OTHER INFORMATION: n = C or A
<220> FEATURE:
<221> NAME/KEY: variation
<222> LOCATION: (380)..(380)
<223> OTHER INFORMATION: n = T or C
<220> FEATURE:
<221> NAME/KEY: variation
<222> LOCATION: (501)..(501)
<223> OTHER INFORMATION: n = T or C
<220> FEATURE:
<221> NAME/KEY: variation
<222> LOCATION: (545)..(545)
<223> OTHER INFORMATION: n = A or G
<220> FEATURE:
<221> NAME/KEY: variation
<222> LOCATION: (572)..(572)
<223> OTHER INFORMATION: n = A or G
<220> FEATURE:
<221> NAME/KEY: variation
<222> LOCATION: (709)..(709)
<223> OTHER INFORMATION: n = A or C
<220> FEATURE:
<221> NAME/KEY: variation
<222> LOCATION: (1039)..(1039)
<223> OTHER INFORMATION: n = G or A
<220> FEATURE:
<221> NAME/KEY: variation
<222> LOCATION: (1114)..(1114)
<223> OTHER INFORMATION: n = G or A
<220> FEATURE:
<221> NAME/KEY: variation
<222> LOCATION: (1117)..(1117)
<223> OTHER INFORMATION: n = C or A
<220> FEATURE:
<221> NAME/KEY: variation
<222> LOCATION: (1448)..(1448)
<223> OTHER INFORMATION: n = T or C
<220> FEATURE:
<221> NAME/KEY: variation
<222> LOCATION: (1808)..(1808)
<223> OTHER INFORMATION: n = G or A
<220> FEATURE:
<221> NAME/KEY: variation
<222> LOCATION: (2274)..(2274)
<223> OTHER INFORMATION: n = G or A
<220> FEATURE:
<221> NAME/KEY: variation
<222> LOCATION: (2318)..(2318)
<223> OTHER INFORMATION: n = G or A

<400> SEQUENCE: 1 atg ctg ctc tgc acg gct cgc ctg gtc ggc ctg cag ctt ctc att tcc      48
Met Leu Leu Cys Thr Ala Arg Leu Val Gly Leu Gln Leu Leu Ile Ser
1               5                  10                  15 tgc tgc tgg gcc ttt gcc tgc cat agc acg gag tct tct cct gac ttc      96
Cys Cys Trp Ala Phe Ala Cys His Ser Thr Glu Ser Ser Pro Asp Phe
            20                  25                  30 acc ctc ccc gga gat tac ctc ctg gca ggc ctg ttc cct ctc cat tct     144
```

```
Thr Leu Pro Gly Asp Tyr Leu Leu Ala Gly Leu Phe Pro Leu His Ser
     35                  40                  45 ggc tgt ctg cag gtg agg cac aga ccc gag gtg acc ctg tgt gac agg        192
Gly Cys Leu Gln Val Arg His Arg Pro Glu Val Thr Leu Cys Asp Arg
 50                  55                  60 tct tgt agn ttc aat gag cat ggc tac cac ctc ttc cag gct atg cgg        240
Ser Cys Ser Phe Asn Glu His Gly Tyr His Leu Phe Gln Ala Met Arg
 65                  70                  75                  80 ctt ggg gtt gag gag ata aac aac tcc acg gcc ctg ctg ccc anc atc        288
Leu Gly Val Glu Glu Ile Asn Asn Ser Thr Ala Leu Leu Pro Asn Ile
                 85                  90                  95 acc ctg ggg tac cag ctg tat gat gtg tgt tct gac tct gnc aat gtg        336
Thr Leu Gly Tyr Gln Leu Tyr Asp Val Cys Ser Asp Ser Ala Asn Val
             100                 105                 110 tat gcc acg ctg aga gtg ctc tcc ctg cca ggg caa cac nac ana gag        384
Tyr Ala Thr Leu Arg Val Leu Ser Leu Pro Gly Gln His His Ile Glu
         115                 120                 125 ctc caa gga gac ctt ctc cac tat tcc cct acg gtg ctg gca gtg att        432
Leu Gln Gly Asp Leu Leu His Tyr Ser Pro Thr Val Leu Ala Val Ile
     130                 135                 140 ggg cct gac agc acc aac cgt gct gcc acc aca gcc gcc ctg ctg agc        480
Gly Pro Asp Ser Thr Asn Arg Ala Ala Thr Thr Ala Ala Leu Leu Ser
145                 150                 155                 160 cct ttc ctg gtg ccc atg atn agc tat gcg gcc agc agc gag acg ctc        528
Pro Phe Leu Val Pro Met Ile Ser Tyr Ala Ala Ser Ser Glu Thr Leu
                 165                 170                 175 agc gtg aag cgg cag tnt ccc tct ttc ctg cgc acc atc ccc ant gac        576
Ser Val Lys Arg Gln Tyr Pro Ser Phe Leu Arg Thr Ile Pro Asn Asp
             180                 185                 190 aag tac cag gtg gag acc atg gtg ctg ctg ctg cag aag ttc ggg tgg        624
Lys Tyr Gln Val Glu Thr Met Val Leu Leu Leu Gln Lys Phe Gly Trp
         195                 200                 205 acc tgg atc tct ctg gtt ggc agc agt gac gac tat ggg cag cta ggg        672
Thr Trp Ile Ser Leu Val Gly Ser Ser Asp Asp Tyr Gly Gln Leu Gly
     210                 215                 220 gtg cag gca ctg gag aac cag gcc act ggt cag ggg ntc tgc att gct        720
Val Gln Ala Leu Glu Asn Gln Ala Thr Gly Gln Gly Ile Cys Ile Ala
225                 230                 235                 240 ttc aag gac atc atg ccc ttc tct gcc cag gtg ggc gat gag agg atg        768
Phe Lys Asp Ile Met Pro Phe Ser Ala Gln Val Gly Asp Glu Arg Met
                 245                 250                 255 cag tgc ctc atg cgc cac ctg gcc cag gcc ggg gcc acc gtc gtg gtt        816
Gln Cys Leu Met Arg His Leu Ala Gln Ala Gly Ala Thr Val Val Val
             260                 265                 270 gtt ttt tcc agc cgg cag ttg gcc agg gtg ttt ttc gag tcc gtg gtg        864
Val Phe Ser Ser Arg Gln Leu Ala Arg Val Phe Phe Glu Ser Val Val
         275                 280                 285 ctg acc aac ctg act ggc aag gtg tgg gtc gcc tca gaa gcc tgg gcc        912
Leu Thr Asn Leu Thr Gly Lys Val Trp Val Ala Ser Glu Ala Trp Ala
     290                 295                 300 ctc tcc agg cac atc act ggg gtg ccc ggg atc cag cgc att ggg atg        960
Leu Ser Arg His Ile Thr Gly Val Pro Gly Ile Gln Arg Ile Gly Met
305                 310                 315                 320 gtg ctg ggc gtg gcc atc cag aag agg gct gtc cct ggc ctg aag gcg       1008
Val Leu Gly Val Ala Ile Gln Lys Arg Ala Val Pro Gly Leu Lys Ala
                 325                 330                 335 ttt gaa gaa gcc tat gcc cgg gca gac aag nag gcc cct agg cct tgc       1056
Phe Glu Glu Ala Tyr Ala Arg Ala Asp Lys Lys Ala Pro Arg Pro Cys
             340                 345                 350
```

| | |
|---|---|
| cac aag ggc tcc tgg tgc agc agc aat cag ctc tgc aga gaa tgc caa<br>His Lys Gly Ser Trp Cys Ser Ser Asn Gln Leu Cys Arg Glu Cys Gln<br>355                         360                    365 | 1104 |
| gct ttc atg nca nac acg atg ccc aag ctc aaa gcc ttc tcc atg agt<br>Ala Phe Met Ala His Thr Met Pro Lys Leu Lys Ala Phe Ser Met Ser<br>370                       375                       380 | 1152 |
| tct gcc tac aac gca tac cgg gct gtg tat gcg gtg gcc cat ggc ctc<br>Ser Ala Tyr Asn Ala Tyr Arg Ala Val Tyr Ala Val Ala His Gly Leu<br>385                         390                    395               400 | 1200 |
| cac cag ctc ctg ggc tgt gcc tct gga gct tgt tcc agg ggc cga gtc<br>His Gln Leu Leu Gly Cys Ala Ser Gly Ala Cys Ser Arg Gly Arg Val<br>                       405                    410                    415 | 1248 |
| tac ccc tgg cag ctt ttg gag cag atc cac aag gtg cat ttc ctt cta<br>Tyr Pro Trp Gln Leu Leu Glu Gln Ile His Lys Val His Phe Leu Leu<br>420                         425                      430 | 1296 |
| cac aag gac act gtg gcg ttt aat gac aac aga gat ccc ctc agt agc<br>His Lys Asp Thr Val Ala Phe Asn Asp Asn Arg Asp Pro Leu Ser Ser<br>                       435                    440                    445 | 1344 |
| tat aac ata att gcc tgg gac tgg aat gga ccc aag tgg acc ttc acg<br>Tyr Asn Ile Ile Ala Trp Asp Trp Asn Gly Pro Lys Trp Thr Phe Thr<br>450                         455                      460 | 1392 |
| gtc ctc ggt tcc tcc aca tgg tct cca gtt cag cta aac ata aat gag<br>Val Leu Gly Ser Ser Thr Trp Ser Pro Val Gln Leu Asn Ile Asn Glu<br>465                         470                    475               480 | 1440 |
| acc aaa anc cag tgg cac gga aag gac aac cag gtg cct aag tct gtg<br>Thr Lys Ile Gln Trp His Gly Lys Asp Asn Gln Val Pro Lys Ser Val<br>                       485                    490                    495 | 1488 |
| tgt tcc agc gac tgt ctt gaa ggg cac cag cga gtg gtt acg ggt ttc<br>Cys Ser Ser Asp Cys Leu Glu Gly His Gln Arg Val Val Thr Gly Phe<br>500                         505                    510 | 1536 |
| cat cac tgc tgc ttt gag tgt gtg ccc tgt ggg gct ggg acc ttc ctc<br>His His Cys Cys Phe Glu Cys Val Pro Cys Gly Ala Gly Thr Phe Leu<br>                       515                    520                    525 | 1584 |
| aac aag agt gac ctc tac aga tgc cag cct tgt ggg aaa gaa gag tgg<br>Asn Lys Ser Asp Leu Tyr Arg Cys Gln Pro Cys Gly Lys Glu Glu Trp<br>530                         535                    540 | 1632 |
| gca cct gag gga agc cag acc tgc ttc ccg cgc act gtg gtg ttt ttg<br>Ala Pro Glu Gly Ser Gln Thr Cys Phe Pro Arg Thr Val Val Phe Leu<br>545                         550                    555               560 | 1680 |
| gct ttg cgt gag cac acc tct tgg gtg ctg ctg gca gct aac acg ctg<br>Ala Leu Arg Glu His Thr Ser Trp Val Leu Leu Ala Ala Asn Thr Leu<br>                       565                    570                    575 | 1728 |
| ctg ctg ctg ctg ctg ctt ggg act gct ggc ctg ttt gcc tgg cac cta<br>Leu Leu Leu Leu Leu Leu Gly Thr Ala Gly Leu Phe Ala Trp His Leu<br>580                         585                    590 | 1776 |
| gac acc cct gtg gtg agg tca gca ggg ggc cnc ctg tgc ttt ctt atg<br>Asp Thr Pro Val Val Arg Ser Ala Gly Gly Arg Leu Cys Phe Leu Met<br>                       595                    600                    605 | 1824 |
| ctg ggc tcc ctg gca gca ggt agt ggc agc ctc tat ggc ttc ttt ggg<br>Leu Gly Ser Leu Ala Ala Gly Ser Gly Ser Leu Tyr Gly Phe Phe Gly<br>610                         615                    620 | 1872 |
| gaa ccc aca agg cct gcg tgc ttg cta cgc cag gcc ctc ttt gcc ctt<br>Glu Pro Thr Arg Pro Ala Cys Leu Leu Arg Gln Ala Leu Phe Ala Leu<br>625                         630                    635               640 | 1920 |
| ggt ttc acc atc ttc ctg tcc tgc ctg aca gtt cgc tca ttc caa cta<br>Gly Phe Thr Ile Phe Leu Ser Cys Leu Thr Val Arg Ser Phe Gln Leu<br>                       645                    650                    655 | 1968 |
| atc atc atc ttc aag ttt tcc acc aag gta cct aca ttc tac cac gcc<br>Ile Ile Ile Phe Lys Phe Ser Thr Lys Val Pro Thr Phe Tyr His Ala<br>660                         665                    670 | 2016 |

-continued

```
tgg gtc caa aac cac ggt gct ggc ctg ttt gtg atg atc agc tca gcg    2064
Trp Val Gln Asn His Gly Ala Gly Leu Phe Val Met Ile Ser Ser Ala
            675                 680                 685 gcc cag ctg ctt atc tgt cta act tgg ctg gtg gtg tgg acc cca ctg    2112
Ala Gln Leu Leu Ile Cys Leu Thr Trp Leu Val Val Trp Thr Pro Leu
    690                 695                 700 cct gct agg gaa tac cag cgc ttc ccc cat ctg gtg atg ctt gag tgc    2160
Pro Ala Arg Glu Tyr Gln Arg Phe Pro His Leu Val Met Leu Glu Cys
705                 710                 715                 720 aca gag acc aac tcc ctg ggc ttc ata ctg gcc ttc ctc tac aat ggc    2208
Thr Glu Thr Asn Ser Leu Gly Phe Ile Leu Ala Phe Leu Tyr Asn Gly
                725                 730                 735 ctc ctc tcc atc agt gcc ttt gcc tgc agc tac ctg ggt aag gac ttg    2256
Leu Leu Ser Ile Ser Ala Phe Ala Cys Ser Tyr Leu Gly Lys Asp Leu
            740                 745                 750 cca gag aac tac aac gan gcc aaa tgt gtc acc ttc agc ctg ctc ttc    2304
Pro Glu Asn Tyr Asn Glu Ala Lys Cys Val Thr Phe Ser Leu Leu Phe
        755                 760                 765 aac ttc gtg tcc tng atc gcc ttc ttc acc acg gcc agc gtc tac gac    2352
Asn Phe Val Ser Trp Ile Ala Phe Phe Thr Thr Ala Ser Val Tyr Asp
    770                 775                 780 ggc aag tac ctg cct gcg gcc aac atg atg gct ggg ctg agc agc ctg    2400
Gly Lys Tyr Leu Pro Ala Ala Asn Met Met Ala Gly Leu Ser Ser Leu
785                 790                 795                 800 agc agc ggc ttc ggt ggg tat ttt ctg cct aag tgc tac gtg atc ctc    2448
Ser Ser Gly Phe Gly Gly Tyr Phe Leu Pro Lys Cys Tyr Val Ile Leu
                805                 810                 815 tgc cgc cca gac ctc aac agc aca gag cac ttc cag gcc tcc att cag    2496
Cys Arg Pro Asp Leu Asn Ser Thr Glu His Phe Gln Ala Ser Ile Gln
            820                 825                 830 gac tac acg agg cgc tgc ggc tcc acc tga                            2526
Asp Tyr Thr Arg Arg Cys Gly Ser Thr
        835                 840

<210> SEQ ID NO 2
<211> LENGTH: 841
<212> TYPE: PRT
<213> ORGANISM: Homo sapiens

<400> SEQUENCE: 2

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140
```

```
Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
            165                 170                 175

Ser Val Lys Arg Gln Tyr Pro Ser Phe Leu Arg Thr Ile Pro Asn Asp
        180                 185                 190

Lys Tyr Gln Val Glu Thr Met Val Leu Leu Gln Lys Phe Gly Trp
    195                 200                 205

Thr Trp Ile Ser Leu Val Gly Ser Ser Asp Asp Tyr Gly Gln Leu Gly
        210                 215                 220

Val Gln Ala Leu Glu Asn Gln Ala Thr Gly Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
    450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560
```

```
Ala Leu Arg Glu His Thr Ser Trp Val Leu Ala Ala Asn Thr Leu
            565                 570                 575

Leu Leu Leu Leu Leu Leu Gly Thr Ala Gly Leu Phe Ala Trp His Leu
        580                 585                 590

Asp Thr Pro Val Val Arg Ser Ala Gly Gly Arg Leu Cys Phe Leu Met
            595                 600                 605

Leu Gly Ser Leu Ala Ala Gly Ser Gly Ser Leu Tyr Gly Phe Phe Gly
        610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
            645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
            725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
        770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
            805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
            835                 840
```

<210> SEQ ID NO 3
<211> LENGTH: 2520
<212> TYPE: DNA
<213> ORGANISM: Homo sapiens
<220> FEATURE:
<221> NAME/KEY: CDS
<222> LOCATION: (1)..(2520)
<220> FEATURE:
<221> NAME/KEY: variation
<222> LOCATION: (26)..(26)
<223> OTHER INFORMATION: n = C or G
<220> FEATURE:
<221> NAME/KEY: variation
<222> LOCATION: (62)..(62)
<223> OTHER INFORMATION: n = C or T
<220> FEATURE:
<221> NAME/KEY: variation
<222> LOCATION: (571)..(571)
<223> OTHER INFORMATION: n = A or G
<220> FEATURE:
<221> NAME/KEY: variation
<222> LOCATION: (634)..(634)
<223> OTHER INFORMATION: n = A or G
<220> FEATURE:

<221> NAME/KEY: variation
<222> LOCATION: (700)..(700)
<223> OTHER INFORMATION: n = A or G
<220> FEATURE:
<221> NAME/KEY: variation
<222> LOCATION: (882)..(882)
<223> OTHER INFORMATION: n = T or G
<220> FEATURE:
<221> NAME/KEY: variation
<222> LOCATION: (949)..(949)
<223> OTHER INFORMATION: n = G or C
<220> FEATURE:
<221> NAME/KEY: variation
<222> LOCATION: (1320)..(1320)
<223> OTHER INFORMATION: n = G or A
<220> FEATURE:
<221> NAME/KEY: variation
<222> LOCATION: (1344)..(1344)
<223> OTHER INFORMATION: n = G or A
<220> FEATURE:
<221> NAME/KEY: variation
<222> LOCATION: (1456)..(1456)
<223> OTHER INFORMATION: n = A or G
<220> FEATURE:
<221> NAME/KEY: variation
<222> LOCATION: (1719)..(1719)
<223> OTHER INFORMATION: n = C or T
<220> FEATURE:
<221> NAME/KEY: variation
<222> LOCATION: (1720)..(1720)
<223> OTHER INFORMATION: n = G or A
<220> FEATURE:
<221> NAME/KEY: variation
<222> LOCATION: (2065)..(2065)
<223> OTHER INFORMATION: n = A or C
<220> FEATURE:
<221> NAME/KEY: variation
<222> LOCATION: (2092)..(2092)
<223> OTHER INFORMATION: n = C or T
<220> FEATURE:
<221> NAME/KEY: variation
<222> LOCATION: (2112)..(2112)
<223> OTHER INFORMATION: n = C or T
<220> FEATURE:
<221> NAME/KEY: variation
<222> LOCATION: (2319)..(2319)
<223> OTHER INFORMATION: n = C or T
<220> FEATURE:
<221> NAME/KEY: variation
<222> LOCATION: (2370)..(2370)
<223> OTHER INFORMATION: n = C or T
<220> FEATURE:
<221> NAME/KEY: variation
<222> LOCATION: (2513)..(2513)
<223> OTHER INFORMATION: n = G or A

<400> SEQUENCE: 3

```
atg ggg ccc agg gca aag acc atc tnc tcc ctg ttc ttc ctc cta tgg      48
Met Gly Pro Arg Ala Lys Thr Ile Cys Ser Leu Phe Phe Leu Leu Trp
1               5                   10                  15 gtc ctg gct gag cng gct gag aac tcg gac ttc tac ctg cct ggg gat      96
Val Leu Ala Glu Pro Ala Glu Asn Ser Asp Phe Tyr Leu Pro Gly Asp
            20                  25                  30 tac ctc ctg ggt ggc ctc ttc tcc ctc cat gcc aac atg aag ggc att     144
Tyr Leu Leu Gly Gly Leu Phe Ser Leu His Ala Asn Met Lys Gly Ile
        35                  40                  45 gtt cac ctt aac ttc ctg cag gtg ccc atg tgc aag gag tat gaa gtg     192
Val His Leu Asn Phe Leu Gln Val Pro Met Cys Lys Glu Tyr Glu Val
    50                  55                  60 aag gtg ata ggc tac aac ctc atg cag gcc atg cgc ttc gcg gtg gag     240
Lys Val Ile Gly Tyr Asn Leu Met Gln Ala Met Arg Phe Ala Val Glu
65                  70                  75                  80 gag atc aac aat gac agc agc ctg ctg cct ggt gtg ctg ctg ggc tat     288
Glu Ile Asn Asn Asp Ser Ser Leu Leu Pro Gly Val Leu Leu Gly Tyr
```

```
                Glu Ile Asn Asn Asp Ser Ser Leu Leu Pro Gly Val Leu Leu Gly Tyr
                                    85                  90                  95 gag atc gtg gat gtg tgc tac atc tcc aac aat gtc cag ccg gtg ctc          336
Glu Ile Val Asp Val Cys Tyr Ile Ser Asn Asn Val Gln Pro Val Leu
            100                 105                 110 tac ttc ctg gca cac gag gac aac ctc ctt ccc atc caa gag gac tac          384
Tyr Phe Leu Ala His Glu Asp Asn Leu Leu Pro Ile Gln Glu Asp Tyr
            115                 120                 125 agt aac tac att tcc cgt gtg gtg gct gtc att ggc cct gac aac tcc          432
Ser Asn Tyr Ile Ser Arg Val Val Ala Val Ile Gly Pro Asp Asn Ser
        130                 135                 140 gag tct gtc atg act gtg gcc aac ttc ctc tcc cta ttt ctc ctt cca          480
Glu Ser Val Met Thr Val Ala Asn Phe Leu Ser Leu Phe Leu Leu Pro
145                 150                 155                 160 cag atc acc tac agc gcc atc agc gat gag ctg cga gac aag gtg cgc          528
Gln Ile Thr Tyr Ser Ala Ile Ser Asp Glu Leu Arg Asp Lys Val Arg
                165                 170                 175 ttc ccg gct ttg ctg cgt acc aca ccc agc gcc gac cac cac ntc gag          576
Phe Pro Ala Leu Leu Arg Thr Thr Pro Ser Ala Asp His His Val Glu
            180                 185                 190 gcc atg gtg cag ctg atg ctg cac ttc cgc tgg aac tgg atc att gtg          624
Ala Met Val Gln Leu Met Leu His Phe Arg Trp Asn Trp Ile Ile Val
        195                 200                 205 ctg gtg agc ngc gac acc tat ggc cgc gac aat ggc cag ctg ctt ggc          672
Leu Val Ser Ser Asp Thr Tyr Gly Arg Asp Asn Gly Gln Leu Leu Gly
210                 215                 220 gag cgc gtg gcc cgg cgc gac atc tgc ntc gcc ttc cag gag acg ctg          720
Glu Arg Val Ala Arg Arg Asp Ile Cys Ile Ala Phe Gln Glu Thr Leu
225                 230                 235                 240 ccc aca ctg cag ccc aac cag aac atg acg tca gag gag cgc cag cgc          768
Pro Thr Leu Gln Pro Asn Gln Asn Met Thr Ser Glu Glu Arg Gln Arg
                245                 250                 255 ctg gtg acc att gtg gac aag ctg cag cag agc aca gcg cgc gtc gtg          816
Leu Val Thr Ile Val Asp Lys Leu Gln Gln Ser Thr Ala Arg Val Val
            260                 265                 270 gtc gtg ttc tcg ccc gac ctg acc ctg tac cac ttc ttc aat gag gtg          864
Val Val Phe Ser Pro Asp Leu Thr Leu Tyr His Phe Phe Asn Glu Val
        275                 280                 285 ctg cgc cag aac ttc acn ggc gcc gtg tgg atc gcc tcc gag tcc tgg          912
Leu Arg Gln Asn Phe Thr Gly Ala Val Trp Ile Ala Ser Glu Ser Trp
290                 295                 300 gcc atc gac ccg gtc ctg cac aac ctc acg gag ctg ngc cac ttg ggc          960
Ala Ile Asp Pro Val Leu His Asn Leu Thr Glu Leu Gly His Leu Gly
305                 310                 315                 320 acc ttc ctg ggc atc acc atc cag agc gtg ccc atc ccg ggc ttc agt         1008
Thr Phe Leu Gly Ile Thr Ile Gln Ser Val Pro Ile Pro Gly Phe Ser
                325                 330                 335 gag ttc cgc gag tgg ggc cca cag gct ggg ccg cca ccc ctc agc agg         1056
Glu Phe Arg Glu Trp Gly Pro Gln Ala Gly Pro Pro Pro Leu Ser Arg
            340                 345                 350 acc agc cag agc tat acc tgc aac cag gag tgc gac aac tgc ctg aac         1104
Thr Ser Gln Ser Tyr Thr Cys Asn Gln Glu Cys Asp Asn Cys Leu Asn
        355                 360                 365 gcc acc ttg tcc ttc aac acc att ctc agg ctc tct ggg gag cgt gtc         1152
Ala Thr Leu Ser Phe Asn Thr Ile Leu Arg Leu Ser Gly Glu Arg Val
370                 375                 380 gtc tac agc gtg tac tct gcg gtc tat gct gtg gcc cat gcc ctg cac         1200
Val Tyr Ser Val Tyr Ser Ala Val Tyr Ala Val Ala His Ala Leu His
385                 390                 395                 400
```

-continued

| | | |
|---|---|---|
| agc ctc ctc ggc tgt gac aaa agc acc tgc acc aag agg gtg gtc tac<br>Ser Leu Leu Gly Cys Asp Lys Ser Thr Cys Thr Lys Arg Val Val Tyr<br>405 410 415 | | 1248 |
| ccc tgg cag ctg ctt gag gag atc tgg aag gtc aac ttc act ctc ctg<br>Pro Trp Gln Leu Leu Glu Glu Ile Trp Lys Val Asn Phe Thr Leu Leu<br>420 425 430 | | 1296 |
| gac cac caa atc ttc ttc gac ccn caa ggg gac gtg gct ctg cac ttn<br>Asp His Gln Ile Phe Phe Asp Pro Gln Gly Asp Val Ala Leu His Leu<br>435 440 445 | | 1344 |
| gag att gtc cag tgg caa tgg gac cgg agc cag aat ccc ttc cag agc<br>Glu Ile Val Gln Trp Gln Trp Asp Arg Ser Gln Asn Pro Phe Gln Ser<br>450 455 460 | | 1392 |
| gtc gcc tcc tac tac ccc ctg cag cga cag ctg aag aac atc caa gac<br>Val Ala Ser Tyr Tyr Pro Leu Gln Arg Gln Leu Lys Asn Ile Gln Asp<br>465 470 475 480 | | 1440 |
| atc tcc tgg cac acc ntc aac aac acg atc cct atg tcc atg tgt tcc<br>Ile Ser Trp His Thr Val Asn Asn Thr Ile Pro Met Ser Met Cys Ser<br>485 490 495 | | 1488 |
| aag agg tgc cag tca ggg caa aag aag aag cct gtg ggc atc cac gtc<br>Lys Arg Cys Gln Ser Gly Gln Lys Lys Lys Pro Val Gly Ile His Val<br>500 505 510 | | 1536 |
| tgc tgc ttc gag tgc atc gac tgc ctt ccc ggc acc ttc ctc aac cac<br>Cys Cys Phe Glu Cys Ile Asp Cys Leu Pro Gly Thr Phe Leu Asn His<br>515 520 525 | | 1584 |
| act gaa gat gaa tat gaa tgc cag gcc tgc ccg aat aac gag tgg tcc<br>Thr Glu Asp Glu Tyr Glu Cys Gln Ala Cys Pro Asn Asn Glu Trp Ser<br>530 535 540 | | 1632 |
| tac cag agt gag acc tcc tgc ttc aag cgg cag ctg gtc ttc ctg gaa<br>Tyr Gln Ser Glu Thr Ser Cys Phe Lys Arg Gln Leu Val Phe Leu Glu<br>545 550 555 560 | | 1680 |
| tgg cat gag gca ccc acc atc gct gtg gcc ctg ctg gcn ncc ctg ggc<br>Trp His Glu Ala Pro Thr Ile Ala Val Ala Leu Leu Ala Ala Leu Gly<br>565 570 575 | | 1728 |
| ttc ctc agc acc ctg gcc atc ctg gtg ata ttc tgg agg cac ttc cag<br>Phe Leu Ser Thr Leu Ala Ile Leu Val Ile Phe Trp Arg His Phe Gln<br>580 585 590 | | 1776 |
| aca ccc ata gtt cgc tcg gct ggg ggc ccc atg tgc ttc ctg atg ctg<br>Thr Pro Ile Val Arg Ser Ala Gly Gly Pro Met Cys Phe Leu Met Leu<br>595 600 605 | | 1824 |
| aca ctg ctg ctg gtg gca tac atg gtg gtc ccg gtg tac gtg ggg ccg<br>Thr Leu Leu Leu Val Ala Tyr Met Val Val Pro Val Tyr Val Gly Pro<br>610 615 620 | | 1872 |
| ccc aag gtc tcc acc tgc ctc tgc cgc cag gcc ctc ttt ccc ctc tgc<br>Pro Lys Val Ser Thr Cys Leu Cys Arg Gln Ala Leu Phe Pro Leu Cys<br>625 630 635 640 | | 1920 |
| ttc aca att tgc atc tcc tgt atc gcc gtg cgt tct ttc cag atc gtc<br>Phe Thr Ile Cys Ile Ser Cys Ile Ala Val Arg Ser Phe Gln Ile Val<br>645 650 655 | | 1968 |
| tgc gcc ttc aag atg gcc agc cgc ttc cca cgc gcc tac agc tac tgg<br>Cys Ala Phe Lys Met Ala Ser Arg Phe Pro Arg Ala Tyr Ser Tyr Trp<br>660 665 670 | | 2016 |
| gtc cgc tac cag ggg ccc tac gtc tct atg gca ttt atc acg gta ctc<br>Val Arg Tyr Gln Gly Pro Tyr Val Ser Met Ala Phe Ile Thr Val Leu<br>675 680 685 | | 2064 |
| naa atg gtc att gtg gta att ggc atg ntg gcc acg ggc ctc agt ccn<br>Lys Met Val Ile Val Val Ile Gly Met Leu Ala Thr Gly Leu Ser Pro<br>690 695 700 | | 2112 |
| acc acc cgt act gac ccc gat gac ccc aag atc aca att gtc tcc tgt<br>Thr Thr Arg Thr Asp Pro Asp Asp Pro Lys Ile Thr Ile Val Ser Cys<br>705 710 715 720 | | 2160 |

```
aac ccc aac tac cgc aac agc ctg ctg ttc aac acc agc ctg gac ctg      2208
Asn Pro Asn Tyr Arg Asn Ser Leu Leu Phe Asn Thr Ser Leu Asp Leu
            725                 730                 735 ctg ctc tca gtg gtg ggt ttc agc ttc gcc tac atg ggc aaa gag ctg      2256
Leu Leu Ser Val Val Gly Phe Ser Phe Ala Tyr Met Gly Lys Glu Leu
        740                 745                 750 ccc acc aac tac aac gag gcc aag ttc atc acc ctc agc atg acc ttc      2304
Pro Thr Asn Tyr Asn Glu Ala Lys Phe Ile Thr Leu Ser Met Thr Phe
    755                 760                 765 tat ttc acc tca tcn gtc tcc ctc tgc acc ttc atg tct gcc tac agc      2352
Tyr Phe Thr Ser Ser Val Ser Leu Cys Thr Phe Met Ser Ala Tyr Ser
770                 775                 780 ggg gtg ctg gtc acc atn gtg gac ctc ttg gtc act gtg ctc aac ctc      2400
Gly Val Leu Val Thr Ile Val Asp Leu Leu Val Thr Val Leu Asn Leu
785                 790                 795                 800 ctg gcc atc agc ctg ggc tac ttc ggc ccc aag tgc tac atg atc ctc      2448
Leu Ala Ile Ser Leu Gly Tyr Phe Gly Pro Lys Cys Tyr Met Ile Leu
            805                 810                 815 ttc tac ccg gag cgc aac acg ccc gcc tac ttc aac agc atg atc cag      2496
Phe Tyr Pro Glu Arg Asn Thr Pro Ala Tyr Phe Asn Ser Met Ile Gln
        820                 825                 830 ggc tac acc atg agg ang gac tag                                      2520
Gly Tyr Thr Met Arg Arg Asp
    835
```

<210> SEQ ID NO 4
<211> LENGTH: 839
<212> TYPE: PRT
<213> ORGANISM: Homo sapiens

<400> SEQUENCE: 4

```
Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205
```

-continued

```
Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
                260                 265                 270

Val Val Phe Ser Pro Asp Leu Thr Leu Tyr His Phe Asn Glu Val
            275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Leu Ser Arg
                340                 345                 350

Thr Ser Gln Ser Tyr Thr Cys Asn Gln Glu Cys Asp Asn Cys Leu Asn
    355                 360                 365

Ala Thr Leu Ser Phe Asn Thr Ile Leu Arg Leu Ser Gly Glu Arg Val
370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
                420                 425                 430

Asp His Gln Ile Phe Phe Asp Pro Gln Gly Asp Val Ala Leu His Leu
    435                 440                 445

Glu Ile Val Gln Trp Gln Trp Asp Arg Ser Gln Asn Pro Phe Gln Ser
450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Pro Val Gly Ile His Val
                500                 505                 510

Cys Cys Phe Glu Cys Ile Asp Cys Leu Pro Gly Thr Phe Leu Asn His
            515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
    595                 600                 605

Thr Leu Leu Leu Val Ala Tyr Met Val Val Pro Val Tyr Val Gly Pro
610                 615                 620
```

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
            645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
            675                 680                 685

Lys Met Val Ile Val Val Ile Gly Met Leu Ala Thr Gly Leu Ser Pro
690                 695                 700

Thr Thr Arg Thr Asp Pro Asp Pro Lys Ile Thr Ile Val Ser Cys
705                 710                 715                 720

Asn Pro Asn Tyr Arg Asn Ser Leu Leu Phe Asn Thr Ser Leu Asp Leu
            725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
            755                 760                 765

Tyr Phe Thr Ser Ser Val Ser Leu Cys Thr Phe Met Ser Ala Tyr Ser
770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
            835

<210> SEQ ID NO 5
<211> LENGTH: 2559
<212> TYPE: DNA
<213> ORGANISM: Homo sapiens
<220> FEATURE:
<221> NAME/KEY: CDS
<222> LOCATION: (1)..(2559)
<220> FEATURE:
<221> NAME/KEY: variation
<222> LOCATION: (13)..(13)
<223> OTHER INFORMATION: n = G or A
<220> FEATURE:
<221> NAME/KEY: variation
<222> LOCATION: (284)..(284)
<223> OTHER INFORMATION: n = T or C
<220> FEATURE:
<221> NAME/KEY: variation
<222> LOCATION: (740)..(740)
<223> OTHER INFORMATION: n = G or A
<220> FEATURE:
<221> NAME/KEY: variation
<222> LOCATION: (1099)..(1099)
<223> OTHER INFORMATION: n = G or T
<220> FEATURE:
<221> NAME/KEY: variation
<222> LOCATION: (1248)..(1248)
<223> OTHER INFORMATION: n = C or T
<220> FEATURE:
<221> NAME/KEY: variation
<222> LOCATION: (1323)..(1323)
<223> OTHER INFORMATION: n = G or A
<220> FEATURE:
<221> NAME/KEY: variation
<222> LOCATION: (1362)..(1362)
<223> OTHER INFORMATION: n = C or T
<220> FEATURE:

```
<221> NAME/KEY: variation
<222> LOCATION: (1719)..(1719)
<223> OTHER INFORMATION: n = C or T
<220> FEATURE:
<221> NAME/KEY: variation
<222> LOCATION: (1977)..(1977)
<223> OTHER INFORMATION: n = C or T
<220> FEATURE:
<221> NAME/KEY: variation
<222> LOCATION: (2203)..(2203)
<223> OTHER INFORMATION: n = G or A
<220> FEATURE:
<221> NAME/KEY: variation
<222> LOCATION: (2269)..(2269)
<223> OTHER INFORMATION: n = T or C
<220> FEATURE:
<221> NAME/KEY: variation
<222> LOCATION: (2407)..(2407)
<223> OTHER INFORMATION: n = C or T

<400> SEQUENCE: 5
```

| | | | | | | | | | | | | | | | | |
|---|---|---|---|---|---|---|---|---|---|---|---|---|---|---|---|---|
| atg | ctg | ggc | cct | nct | gtc | ctg | ggc | ctc | agc | ctc | tgg | gct | ctc | ctg | cac | 48 |
| Met | Leu | Gly | Pro | Ala | Val | Leu | Gly | Leu | Ser | Leu | Trp | Ala | Leu | Leu | His | |
| 1 | | | | 5 | | | | | 10 | | | | | 15 | | |
| cct | ggg | acg | ggg | gcc | cca | ttg | tgc | ctg | tca | cag | caa | ctt | agg | atg | aag | 96 |
| Pro | Gly | Thr | Gly | Ala | Pro | Leu | Cys | Leu | Ser | Gln | Gln | Leu | Arg | Met | Lys | |
| | | | 20 | | | | | 25 | | | | | 30 | | | |
| ggg | gac | tac | gtg | ctg | ggg | ggg | ctg | ttc | ccc | ctg | ggc | gag | gcc | gag | gag | 144 |
| Gly | Asp | Tyr | Val | Leu | Gly | Gly | Leu | Phe | Pro | Leu | Gly | Glu | Ala | Glu | Glu | |
| | 35 | | | | | 40 | | | | | 45 | | | | | |
| gct | ggc | ctc | cgc | agc | cgg | aca | cgg | ccc | agc | agc | cct | gtg | tgc | acc | agg | 192 |
| Ala | Gly | Leu | Arg | Ser | Arg | Thr | Arg | Pro | Ser | Ser | Pro | Val | Cys | Thr | Arg | |
| 50 | | | | | 55 | | | | | 60 | | | | | | |
| ttc | tcc | tca | aac | ggc | ctg | ctc | tgg | gca | ctg | gcc | atg | aaa | atg | gcc | gtg | 240 |
| Phe | Ser | Ser | Asn | Gly | Leu | Leu | Trp | Ala | Leu | Ala | Met | Lys | Met | Ala | Val | |
| 65 | | | | 70 | | | | | 75 | | | | | 80 | | |
| gag | gag | atc | aac | aac | aag | tcg | gat | ctg | ctg | ccc | ggg | ctg | cgc | cng | ggc | 288 |
| Glu | Glu | Ile | Asn | Asn | Lys | Ser | Asp | Leu | Leu | Pro | Gly | Leu | Arg | Leu | Gly | |
| | | | | 85 | | | | | 90 | | | | | 95 | | |
| tac | gac | ctc | ttt | gat | acg | tgc | tcg | gag | cct | gtg | gtg | gcc | atg | aag | ccc | 336 |
| Tyr | Asp | Leu | Phe | Asp | Thr | Cys | Ser | Glu | Pro | Val | Val | Ala | Met | Lys | Pro | |
| | | | 100 | | | | | 105 | | | | | 110 | | | |
| agc | ctc | atg | ttc | ctg | gcc | aag | gca | ggc | agc | cgc | gac | atc | gcc | gcc | tac | 384 |
| Ser | Leu | Met | Phe | Leu | Ala | Lys | Ala | Gly | Ser | Arg | Asp | Ile | Ala | Ala | Tyr | |
| | | 115 | | | | | 120 | | | | | 125 | | | | |
| tgc | aac | tac | acg | cag | tac | cag | ccc | cgt | gtg | ctg | gct | gtc | atc | ggg | ccc | 432 |
| Cys | Asn | Tyr | Thr | Gln | Tyr | Gln | Pro | Arg | Val | Leu | Ala | Val | Ile | Gly | Pro | |
| | 130 | | | | | 135 | | | | | 140 | | | | | |
| cac | tcg | tca | gag | ctc | gcc | atg | gtc | acc | ggc | aag | ttc | ttc | agc | ttc | ttc | 480 |
| His | Ser | Ser | Glu | Leu | Ala | Met | Val | Thr | Gly | Lys | Phe | Phe | Ser | Phe | Phe | |
| 145 | | | | | 150 | | | | | 155 | | | | | 160 | |
| ctc | atg | ccc | cag | gtc | agc | tac | ggt | gct | agc | atg | gag | ctg | ctg | agc | gcc | 528 |
| Leu | Met | Pro | Gln | Val | Ser | Tyr | Gly | Ala | Ser | Met | Glu | Leu | Leu | Ser | Ala | |
| | | | | 165 | | | | | 170 | | | | | 175 | | |
| cgg | gag | acc | ttc | ccc | tcc | ttc | ttc | cgc | acc | gtg | ccc | agc | gac | cgt | gtg | 576 |
| Arg | Glu | Thr | Phe | Pro | Ser | Phe | Phe | Arg | Thr | Val | Pro | Ser | Asp | Arg | Val | |
| | | | 180 | | | | | 185 | | | | | 190 | | | |
| cag | ctg | acg | gcc | gcc | gcg | gag | ctg | ctg | cag | gag | ttc | ggc | tgg | aac | tgg | 624 |
| Gln | Leu | Thr | Ala | Ala | Ala | Glu | Leu | Leu | Gln | Glu | Phe | Gly | Trp | Asn | Trp | |
| | | 195 | | | | | 200 | | | | | 205 | | | | |
| gtg | gcc | gcc | ctg | ggc | agc | gac | gac | gag | tac | ggc | cgg | cag | ggc | ctg | agc | 672 |
| Val | Ala | Ala | Leu | Gly | Ser | Asp | Asp | Glu | Tyr | Gly | Arg | Gln | Gly | Leu | Ser | |
| | 210 | | | | | 215 | | | | | 220 | | | | | |
| atc | ttc | tcg | gcc | ctg | gcc | gcg | gca | cgc | ggc | atc | tgc | atc | gcg | cac | gag | 720 |

```
Ile Phe Ser Ala Leu Ala Ala Arg Gly Ile Cys Ile Ala His Glu
225                 230                 235                 240 ggc ctg gtg ccg ctg ccc cnt gcc gat gac tcg cgg ctg ggg aag gtg         768
Gly Leu Val Pro Leu Pro Arg Ala Asp Asp Ser Arg Leu Gly Lys Val
                    245                 250                 255 cag gac gtc ctg cac cag gtg aac cag agc agc gtg cag gtg gtg ctg         816
Gln Asp Val Leu His Gln Val Asn Gln Ser Ser Val Gln Val Val Leu
                260                 265                 270 ctg ttc gcc tcc gtg cac gcc gcc cac gcc ctc ttc aac tac agc atc         864
Leu Phe Ala Ser Val His Ala Ala His Ala Leu Phe Asn Tyr Ser Ile
                275                 280                 285 agc agc agg ctc tcg ccc aag gtg tgg gtg gcc agc gag gcc tgg ctg         912
Ser Ser Arg Leu Ser Pro Lys Val Trp Val Ala Ser Glu Ala Trp Leu
        290                 295                 300 acc tct gac ctg gtc atg ggg ctg ccc ggc atg gcc cag atg ggc acg         960
Thr Ser Asp Leu Val Met Gly Leu Pro Gly Met Ala Gln Met Gly Thr
305                 310                 315                 320 gtg ctt ggc ttc ctc cag agg ggt gcc cag ctg cac gag ttc ccc cag        1008
Val Leu Gly Phe Leu Gln Arg Gly Ala Gln Leu His Glu Phe Pro Gln
                325                 330                 335 tac gtg aag acg cac ctg gcc ctg gcc acc gac ccg gcc ttc tgc tct        1056
Tyr Val Lys Thr His Leu Ala Leu Ala Thr Asp Pro Ala Phe Cys Ser
                340                 345                 350 gcc ctg ggc gag agg gag cag ggt ctg gag gag gac gtg gtg ngc cag        1104
Ala Leu Gly Glu Arg Glu Gln Gly Leu Glu Glu Asp Val Val Gly Gln
                355                 360                 365 cgc tgc ccg cag tgt gac tgc atc acg ctg cag aac gtg agc gca ggg        1152
Arg Cys Pro Gln Cys Asp Cys Ile Thr Leu Gln Asn Val Ser Ala Gly
370                 375                 380 cta aat cac cac cag acg ttc tct gtc tac gca gct gtg tat agc gtg        1200
Leu Asn His His Gln Thr Phe Ser Val Tyr Ala Ala Val Tyr Ser Val
385                 390                 395                 400 gcc cag gcc ctg cac aac act ctt cag tgc aac gcc tca ggc tgc ccn        1248
Ala Gln Ala Leu His Asn Thr Leu Gln Cys Asn Ala Ser Gly Cys Pro
                405                 410                 415 gcg cag gac ccc gtg aag ccc tgg cag ctc ctg gag aac atg tac aac        1296
Ala Gln Asp Pro Val Lys Pro Trp Gln Leu Leu Glu Asn Met Tyr Asn
                420                 425                 430 ctg acc ttc cac gtg ggc ggg ctg ccn ctg cgg ttc gac agc agc gga        1344
Leu Thr Phe His Val Gly Gly Leu Pro Leu Arg Phe Asp Ser Ser Gly
        435                 440                 445 aac gtg gac atg gag tan gac ctg aag ctg tgg gtg tgg cag ggc tca        1392
Asn Val Asp Met Glu Tyr Asp Leu Lys Leu Trp Val Trp Gln Gly Ser
450                 455                 460 gtg ccc agg ctc cac gac gtg ggc agg ttc aac ggc agc ctc agg aca        1440
Val Pro Arg Leu His Asp Val Gly Arg Phe Asn Gly Ser Leu Arg Thr
465                 470                 475                 480 gag cgc ctg aag atc cgc tgg cac acg tct gac aac cag aag ccc gtg        1488
Glu Arg Leu Lys Ile Arg Trp His Thr Ser Asp Asn Gln Lys Pro Val
                485                 490                 495 tcc cgg tgc tcg cgg cag tgc cag gag ggc cag gtg cgc cgg gtc aag        1536
Ser Arg Cys Ser Arg Gln Cys Gln Glu Gly Gln Val Arg Arg Val Lys
                500                 505                 510 ggg ttc cac tcc tgc tgc tac gac tgt gtg gac tgc gag gcg ggc agc        1584
Gly Phe His Ser Cys Cys Tyr Asp Cys Val Asp Cys Glu Ala Gly Ser
                515                 520                 525 tac cgg caa aac cca gac gac atc gcc tgc acc ttt tgt ggc cag gat        1632
Tyr Arg Gln Asn Pro Asp Asp Ile Ala Cys Thr Phe Cys Gly Gln Asp
530                 535                 540
```

```
gag tgg tcc ccg gag cga agc aca cgc tgc ttc cgc cgc agg tct cgg    1680
Glu Trp Ser Pro Glu Arg Ser Thr Arg Cys Phe Arg Arg Arg Ser Arg
545                 550                 555                 560 ttc ctg gca tgg ggc gag ccg gct gtg ctg ctg ctn ctg ctg ctg        1728
Phe Leu Ala Trp Gly Glu Pro Ala Val Leu Leu Leu Leu Leu Leu
                565                 570                 575 agc ctg gcg ctg ggc ctt gtg ctg gct gct ttg ggg ctg ttc gtt cac    1776
Ser Leu Ala Leu Gly Leu Val Leu Ala Ala Leu Gly Leu Phe Val His
                580                 585                 590 cat cgg gac agc cca ctg gtt cag gcc tcg ggg ggc ccc ctg gcc tgc    1824
His Arg Asp Ser Pro Leu Val Gln Ala Ser Gly Gly Pro Leu Ala Cys
                595                 600                 605 ttt ggc ctg gtg tgc ctg ggc ctg gtc tgc ctc agc gtc ctc ctg ttc    1872
Phe Gly Leu Val Cys Leu Gly Leu Val Cys Leu Ser Val Leu Leu Phe
                610                 615                 620 cct ggc cag ccc agc cct gcc cga tgc ctg gcc cag cag ccc ttg tcc    1920
Pro Gly Gln Pro Ser Pro Ala Arg Cys Leu Ala Gln Gln Pro Leu Ser
625                 630                 635                 640 cac ctc ccg ctc acg ggc tgc ctg agc aca ctc ttc ctg cag gcg gcc    1968
His Leu Pro Leu Thr Gly Cys Leu Ser Thr Leu Phe Leu Gln Ala Ala
                645                 650                 655 gag atc ttn gtg gag tca gaa ctg cct ctg agc tgg gca gac cgg ctg    2016
Glu Ile Phe Val Glu Ser Glu Leu Pro Leu Ser Trp Ala Asp Arg Leu
                660                 665                 670 agt ggc tgc ctg cgg ggg ccc tgg gcc tgg ctg gtg gtg ctg ctg gcc    2064
Ser Gly Cys Leu Arg Gly Pro Trp Ala Trp Leu Val Val Leu Leu Ala
                675                 680                 685 atg ctg gtg gag gtc gca ctg tgc acc tgg tac ctg gtg gcc ttc ccg    2112
Met Leu Val Glu Val Ala Leu Cys Thr Trp Tyr Leu Val Ala Phe Pro
690                 695                 700 ccg gag gtg gtg acg gac tgg cac atg ctg ccc acg gag gcg ctg gtg    2160
Pro Glu Val Val Thr Asp Trp His Met Leu Pro Thr Glu Ala Leu Val
705                 710                 715                 720 cac tgc cgc aca cgc tcc tgg gtc agc ttc ggc cta gcg cac ncc acc    2208
His Cys Arg Thr Arg Ser Trp Val Ser Phe Gly Leu Ala His Ala Thr
                725                 730                 735 aat gcc acg ctg gcc ttt ctc tgc ttc ctg ggc act ttc ctg gtg cgg    2256
Asn Ala Thr Leu Ala Phe Leu Cys Phe Leu Gly Thr Phe Leu Val Arg
                740                 745                 750 agc cag ccg ggc ngc tac aac cgt gcc cgt ggc ctc acc ttt gcc atg    2304
Ser Gln Pro Gly Arg Tyr Asn Arg Ala Arg Gly Leu Thr Phe Ala Met
                755                 760                 765 ctg gcc tac ttc atc acc tgg gtc tcc ttt gtg ccc ctc ctg gcc aat    2352
Leu Ala Tyr Phe Ile Thr Trp Val Ser Phe Val Pro Leu Leu Ala Asn
770                 775                 780 gtg cag gtg gtc ctc agg ccc gcc gtg cag atg ggc gcc ctc ctg ctc    2400
Val Gln Val Val Leu Arg Pro Ala Val Gln Met Gly Ala Leu Leu Leu
785                 790                 795                 800 tgt gtc ntg ggc atc ctg gct gcc ttc cac ctg ccc agg tgt tac ctg    2448
Cys Val Leu Gly Ile Leu Ala Ala Phe His Leu Pro Arg Cys Tyr Leu
                805                 810                 815 ctc atg cgg cag cca ggg ctc aac acc ccc gag ttc ttc ctg gga ggg    2496
Leu Met Arg Gln Pro Gly Leu Asn Thr Pro Glu Phe Phe Leu Gly Gly
                820                 825                 830 ggc cct ggg gat gcc caa ggc cag aat gac ggg aac aca gga aat cag    2544
Gly Pro Gly Asp Ala Gln Gly Gln Asn Asp Gly Asn Thr Gly Asn Gln
                835                 840                 845 ggg aaa cat gag tga                                                2559
Gly Lys His Glu
    850
```

<210> SEQ ID NO 6
<211> LENGTH: 852
<212> TYPE: PRT
<213> ORGANISM: Homo sapiens

<400> SEQUENCE: 6

```
Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
```

```
                370                 375                 380
Leu Asn His His Gln Thr Phe Ser Val Tyr Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
                420                 425                 430

Leu Thr Phe His Val Gly Gly Leu Pro Leu Arg Phe Asp Ser Ser Gly
                435                 440                 445

Asn Val Asp Met Glu Tyr Asp Leu Lys Leu Trp Val Trp Gln Gly Ser
450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
                500                 505                 510

Gly Phe His Ser Cys Cys Tyr Asp Cys Val Asp Cys Glu Ala Gly Ser
                515                 520                 525

Tyr Arg Gln Asn Pro Asp Asp Ile Ala Cys Thr Phe Cys Gly Gln Asp
                530                 535                 540

Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
                580                 585                 590

His Arg Asp Ser Pro Leu Val Gln Ala Ser Gly Gly Pro Leu Ala Cys
                595                 600                 605

Phe Gly Leu Val Cys Leu Gly Leu Val Cys Leu Ser Val Leu Leu Phe
                610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
                660                 665                 670

Ser Gly Cys Leu Arg Gly Pro Trp Ala Trp Leu Val Val Leu Leu Ala
                675                 680                 685

Met Leu Val Glu Val Ala Leu Cys Thr Trp Tyr Leu Val Ala Phe Pro
690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
                740                 745                 750

Ser Gln Pro Gly Arg Tyr Asn Arg Ala Arg Gly Leu Thr Phe Ala Met
                755                 760                 765

Leu Ala Tyr Phe Ile Thr Trp Val Ser Phe Val Pro Leu Leu Ala Asn
                770                 775                 780

Val Gln Val Val Leu Arg Pro Ala Val Gln Met Gly Ala Leu Leu Leu
785                 790                 795                 800
```

```
Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850

<210> SEQ ID NO 7
<211> LENGTH: 1302
<212> TYPE: DNA
<213> ORGANISM: Homo sapiens
<220> FEATURE:
<221> NAME/KEY: CDS
<222> LOCATION: (1)..(975)

<400> SEQUENCE: 7 atg ctg ctc tgc acg gct cgc ctg gtc ggc ctg cag ctt ctc att tcc      48
Met Leu Leu Cys Thr Ala Arg Leu Val Gly Leu Gln Leu Leu Ile Ser
1               5                   10                  15 tgc tgc tgg gcc ttt gcc tgc cat agc acg gag tct tct cct gac ttc      96
Cys Cys Trp Ala Phe Ala Cys His Ser Thr Glu Ser Ser Pro Asp Phe
                20                  25                  30 acc ctc ccc gga gat tac ctc ctg gca ggc ctg ttc cct ctc cat tct     144
Thr Leu Pro Gly Asp Tyr Leu Leu Ala Gly Leu Phe Pro Leu His Ser
            35                  40                  45 ggc tgt ctg cag gtg agg cac aga ccc gag gtg acc ctg tgt gac agg     192
Gly Cys Leu Gln Val Arg His Arg Pro Glu Val Thr Leu Cys Asp Arg
        50                  55                  60 tct tgt agc ttc aat gag cat ggc tac cac ctc ttc cag gct atg cgg     240
Ser Cys Ser Phe Asn Glu His Gly Tyr His Leu Phe Gln Ala Met Arg
65                  70                  75                  80 ctt ggg gtt gag gag ata aac aac tcc acg gcc ctg ctg ccc aac atc     288
Leu Gly Val Glu Glu Ile Asn Asn Ser Thr Ala Leu Leu Pro Asn Ile
                85                  90                  95 acc ctg ggg tac cag ctg tat gat gtg tgt tct gac tct gcc aat gtg     336
Thr Leu Gly Tyr Gln Leu Tyr Asp Val Cys Ser Asp Ser Ala Asn Val
            100                 105                 110 tat gcc acg ctg aga gtg ctc tcc ctg cca ggg caa cac cac ata gag     384
Tyr Ala Thr Leu Arg Val Leu Ser Leu Pro Gly Gln His His Ile Glu
        115                 120                 125 ctc caa gga gac ctt ctc cac tat tcc cct acg gtg ctg gca gtg att     432
Leu Gln Gly Asp Leu Leu His Tyr Ser Pro Thr Val Leu Ala Val Ile
    130                 135                 140 ggg cct gac agc acc aac cgt gct gcc acc aca gcc gcc ctg ctg agc     480
Gly Pro Asp Ser Thr Asn Arg Ala Ala Thr Thr Ala Ala Leu Leu Ser
145                 150                 155                 160 cct ttc ctg gtg ccc atg ctt ttg gag cag atc cac aag gtg cat ttc     528
Pro Phe Leu Val Pro Met Leu Leu Glu Gln Ile His Lys Val His Phe
                165                 170                 175 ctt cta cac aag gac act gtg gcg ttt aat gac aac aga gat ccc ctc     576
Leu Leu His Lys Asp Thr Val Ala Phe Asn Asp Asn Arg Asp Pro Leu
            180                 185                 190 agt agc tat aac ata att gcc tgg gac tgg aat gga ccc aag tgg acc     624
Ser Ser Tyr Asn Ile Ile Ala Trp Asp Trp Asn Gly Pro Lys Trp Thr
        195                 200                 205 ttc acg gtc ctc ggt tcc tcc aca tgg tct cca gtt cag cta aac ata     672
Phe Thr Val Leu Gly Ser Ser Thr Trp Ser Pro Val Gln Leu Asn Ile
    210                 215                 220
```

-continued

```
aat gag acc aaa atc cag tgg cac gga aag gac aac cag gtg cct aag        720
Asn Glu Thr Lys Ile Gln Trp His Gly Lys Asp Asn Gln Val Pro Lys
225                 230                 235                 240 tct gtg tgt tcc agc gac tgt ctt gaa ggg cac cag cga gtg gtt acg        768
Ser Val Cys Ser Ser Asp Cys Leu Glu Gly His Gln Arg Val Val Thr
                245                 250                 255 ggt ttc cat cac tgc tgc ttt gag tgt gtg ccc tgt ggg gct ggg acc        816
Gly Phe His His Cys Cys Phe Glu Cys Val Pro Cys Gly Ala Gly Thr
            260                 265                 270 ttc ctc aac aag agt gct acc tgg gta agg act tgc cag aga act aca        864
Phe Leu Asn Lys Ser Ala Thr Trp Val Arg Thr Cys Gln Arg Thr Thr
        275                 280                 285 acg agg cca aat gtg tca cct tca gcc tgc tct tca act tcg tgt cct        912
Thr Arg Pro Asn Val Ser Pro Ser Ala Cys Ser Ser Thr Ser Cys Pro
    290                 295                 300 gga tcg cct tct tca cca cgg cca gcg tct acg acg gca agt acc tgc        960
Gly Ser Pro Ser Ser Pro Arg Pro Ala Ser Thr Thr Ala Ser Thr Cys
305                 310                 315                 320 ctg cgg cca aca tga tggctgggct gagcagcctg agcagcggct tcggtgggta       1015
Leu Arg Pro Thr ttttctgcct aagtgctacg tgatcctctg ccgcccagac ctcaacagca cagagcactt     1075
ccaggcctcc attcaggact acacgaggcg ctgcggctcc acctgaccag tgggtcagca     1135
ggcacggctg gcagccttct ctgccctgag ggtcgaaggt cgagcaggcc gggggtgtcc     1195
gggaggtctt tgggcatcgc ggtctggggt tgggacgtgt aagcgcctgg gagagcctag     1255
accaggctcc gggctgccaa taaagaagtg aaatgcgtaa aaaaaaa                   1302
```

<210> SEQ ID NO 8
<211> LENGTH: 324
<212> TYPE: PRT
<213> ORGANISM: Homo sapiens

<400> SEQUENCE: 8

```
Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Leu Leu Glu Gln Ile His Lys Val His Phe
                165                 170                 175
```

```
Leu Leu His Lys Asp Thr Val Ala Phe Asn Asp Asn Arg Asp Pro Leu
            180                 185                 190

Ser Ser Tyr Asn Ile Ile Ala Trp Asp Trp Asn Gly Pro Lys Trp Thr
        195                 200                 205

Phe Thr Val Leu Gly Ser Ser Thr Trp Ser Pro Val Gln Leu Asn Ile
    210                 215                 220

Asn Glu Thr Lys Ile Gln Trp His Gly Lys Asp Asn Gln Val Pro Lys
225                 230                 235                 240

Ser Val Cys Ser Ser Asp Cys Leu Glu Gly His Gln Arg Val Val Thr
                245                 250                 255

Gly Phe His His Cys Cys Phe Glu Cys Val Pro Cys Gly Ala Gly Thr
            260                 265                 270

Phe Leu Asn Lys Ser Ala Thr Trp Val Arg Thr Cys Gln Arg Thr Thr
        275                 280                 285

Thr Arg Pro Asn Val Ser Pro Ser Ala Cys Ser Ser Thr Ser Cys Pro
    290                 295                 300

Gly Ser Pro Ser Pro Arg Pro Ala Ser Thr Thr Ala Ser Thr Cys
305                 310                 315                 320

Leu Arg Pro Thr

<210> SEQ ID NO 9
<211> LENGTH: 1945
<212> TYPE: DNA
<213> ORGANISM: Homo sapiens
<220> FEATURE:
<221> NAME/KEY: CDS
<222> LOCATION: (1)..(1764)

<400> SEQUENCE: 9 atg ctg ctc tgc acg gct cgc ctg gtc ggc ctg cag ctt ctc att tcc      48
Met Leu Leu Cys Thr Ala Arg Leu Val Gly Leu Gln Leu Leu Ile Ser
1               5                   10                  15 tgc tgc tgg gcc ttt gcc tgc cat agc acg gag tct tct cct gac ttc      96
Cys Cys Trp Ala Phe Ala Cys His Ser Thr Glu Ser Ser Pro Asp Phe
            20                  25                  30 acc ctc ccc gga gat tac ctc ctg gca ggc ctg ttc cct ctc cat tct     144
Thr Leu Pro Gly Asp Tyr Leu Leu Ala Gly Leu Phe Pro Leu His Ser
        35                  40                  45 ggc tgt ctg cag gtg agg cac aga ccc gag gtg acc ctg tgt gac agg     192
Gly Cys Leu Gln Val Arg His Arg Pro Glu Val Thr Leu Cys Asp Arg
    50                  55                  60 tct tgt agc ttc aat gag cat ggc tac cac ctc ttc cag gct atg cgg     240
Ser Cys Ser Phe Asn Glu His Gly Tyr His Leu Phe Gln Ala Met Arg
65                  70                  75                  80 ctt ggg gtt gag gag ata aac aac tcc acg gcc ctg ctg ccc aac atc     288
Leu Gly Val Glu Glu Ile Asn Asn Ser Thr Ala Leu Leu Pro Asn Ile
                85                  90                  95 acc ctg ggg tac cag ctg tat gat gtg tgt tct gac tct gcc aat gtg     336
Thr Leu Gly Tyr Gln Leu Tyr Asp Val Cys Ser Asp Ser Ala Asn Val
            100                 105                 110 tat gcc acg ctg aga gtg ctc tcc ctg cca ggg caa cac cac ata gag     384
Tyr Ala Thr Leu Arg Val Leu Ser Leu Pro Gly Gln His His Ile Glu
        115                 120                 125 ctc caa gga gac ctt ctc cac tat tcc cct acg gtg ctg gca gtg att     432
Leu Gln Gly Asp Leu Leu His Tyr Ser Pro Thr Val Leu Ala Val Ile
    130                 135                 140 ggg cct gac agc acc aac cgt gct gcc acc aca gcc gcc ctg ctg agc     480
Gly Pro Asp Ser Thr Asn Arg Ala Ala Thr Thr Ala Ala Leu Leu Ser
145                 150                 155                 160
```

| | | |
|---|---|---|
| cct ttc ctg gtg ccc atg ctt ttg gag cag atc cac aag gtg cat ttc<br>Pro Phe Leu Val Pro Met Leu Leu Glu Gln Ile His Lys Val His Phe<br>165                    170                    175 | 528 |
| ctt cta cac aag gac act gtg gcg ttt aat gac aac aga gat ccc ctc<br>Leu Leu His Lys Asp Thr Val Ala Phe Asn Asp Asn Arg Asp Pro Leu<br>        180                    185                    190 | 576 |
| agt agc tat aac ata att gcc tgg gac tgg aat gga ccc aag tgg acc<br>Ser Ser Tyr Asn Ile Ile Ala Trp Asp Trp Asn Gly Pro Lys Trp Thr<br>            195                    200                  205 | 624 |
| ttc acg gtc ctc ggt tcc tcc aca tgg tct cca gtt cag cta aac ata<br>Phe Thr Val Leu Gly Ser Ser Thr Trp Ser Pro Val Gln Leu Asn Ile<br>210                    215                    220 | 672 |
| aat gag acc aaa atc cag tgg cac gga aag gac aac cag gtg cct aag<br>Asn Glu Thr Lys Ile Gln Trp His Gly Lys Asp Asn Gln Val Pro Lys<br>225                    230                    235                  240 | 720 |
| tct gtg tgt tcc agc gac tgt ctt gaa ggg cac cag cga gtg gtt acg<br>Ser Val Cys Ser Ser Asp Cys Leu Glu Gly His Gln Arg Val Val Thr<br>                    245                    250                    255 | 768 |
| ggt ttc cat cac tgc tgc ttt gag tgt gtg ccc tgt ggg gct ggg acc<br>Gly Phe His His Cys Cys Phe Glu Cys Val Pro Cys Gly Ala Gly Thr<br>260                    265                    270 | 816 |
| ttc ctc aac aag agt gac ctc tac aga tgc cag cct tgt ggg aaa gaa<br>Phe Leu Asn Lys Ser Asp Leu Tyr Arg Cys Gln Pro Cys Gly Lys Glu<br>            275                    280                    285 | 864 |
| gag tgg gca cct gag gga agc cag acc tgc ttc ccg cgc act gtg gtg<br>Glu Trp Ala Pro Glu Gly Ser Gln Thr Cys Phe Pro Arg Thr Val Val<br>290                    295                    300 | 912 |
| ttt ttg gct ttg cgt gag cac acc tct tgg gtg ctg ctg gca gct aac<br>Phe Leu Ala Leu Arg Glu His Thr Ser Trp Val Leu Leu Ala Ala Asn<br>305                    310                    315                  320 | 960 |
| acg ctg ctg ctg ctg ctg ctt ggg act gct ggc ctg ttt gcc tgg<br>Thr Leu Leu Leu Leu Leu Leu Gly Thr Ala Gly Leu Phe Ala Trp<br>            325                    330                    335 | 1008 |
| cac cta gac acc cct gtg gtg agg tca gca ggg ggc cgc ctg tgc ttt<br>His Leu Asp Thr Pro Val Val Arg Ser Ala Gly Gly Arg Leu Cys Phe<br>                340                    345                    350 | 1056 |
| ctt atg ctg ggc tcc ctg gca gca ggt agt ggc agc ctc tat ggc ttc<br>Leu Met Leu Gly Ser Leu Ala Ala Gly Ser Gly Ser Leu Tyr Gly Phe<br>        355                    360                    365 | 1104 |
| ttt ggg gaa ccc aca agg cct gcg tgc ttg cta cgc cag gcc ctc ttt<br>Phe Gly Glu Pro Thr Arg Pro Ala Cys Leu Leu Arg Gln Ala Leu Phe<br>        370                    375                    380 | 1152 |
| gcc ctt ggt ttc acc atc ttc ctg tcc tgc ctg aca gtt cgc tca ttc<br>Ala Leu Gly Phe Thr Ile Phe Leu Ser Cys Leu Thr Val Arg Ser Phe<br>385                    390                    395                  400 | 1200 |
| caa cta atc atc atc ttc aag ttt tcc acc aag gta cct aca ttc tac<br>Gln Leu Ile Ile Ile Phe Lys Phe Ser Thr Lys Val Pro Thr Phe Tyr<br>                405                    410                    415 | 1248 |
| cac gcc tgg gtc caa aac cac ggt gct ggc ctg ttt gtg atg atc agc<br>His Ala Trp Val Gln Asn His Gly Ala Gly Leu Phe Val Met Ile Ser<br>            420                    425                    430 | 1296 |
| tca gcg gcc cag ctg ctt atc tgt cta act tgg ctg gtg gtg tgg acc<br>Ser Ala Ala Gln Leu Leu Ile Cys Leu Thr Trp Leu Val Val Trp Thr<br>        435                    440                    445 | 1344 |
| cca ctg cct gct agg gaa tac cag cgc ttc ccc cat ctg gtg atg ctt<br>Pro Leu Pro Ala Arg Glu Tyr Gln Arg Phe Pro His Leu Val Met Leu<br>        450                    455                    460 | 1392 |
| gag tgc aca gag acc aac tcc ctg ggc ttc ata ctg gcc ttc ctc tac<br>Glu Cys Thr Glu Thr Asn Ser Leu Gly Phe Ile Leu Ala Phe Leu Tyr | 1440 |

```
                465                 470                 475                 480
aat ggc ctc ctc tcc atc agt gcc ttt gcc tgc agc tac ctg ggt aag       1488
Asn Gly Leu Leu Ser Ile Ser Ala Phe Ala Cys Ser Tyr Leu Gly Lys
                        485                 490                 495 gac ttg cca gag aac tac aac gag gcc aaa tgt gtc acc ttc agc ctg       1536
Asp Leu Pro Glu Asn Tyr Asn Glu Ala Lys Cys Val Thr Phe Ser Leu
            500                 505                 510 ctc ttc aac ttc gtg tcc tgg atc gcc ttc ttc acc acg gcc agc gtc       1584
Leu Phe Asn Phe Val Ser Trp Ile Ala Phe Phe Thr Thr Ala Ser Val
                515                 520                 525 tac gac ggc aag tac ctg cct gcg gcc aac atg atg gct ggg ctg agc       1632
Tyr Asp Gly Lys Tyr Leu Pro Ala Ala Asn Met Met Ala Gly Leu Ser
    530                 535                 540 agc ctg agc agc ggc ttc ggt ggg tat ttt ctg cct aag tgc tac gtg       1680
Ser Leu Ser Ser Gly Phe Gly Gly Tyr Phe Leu Pro Lys Cys Tyr Val
545                 550                 555                 560 atc ctc tgc cgc cca gac ctc aac agc aca gag cac ttc cag gcc tcc       1728
Ile Leu Cys Arg Pro Asp Leu Asn Ser Thr Glu His Phe Gln Ala Ser
                565                 570                 575 att cag gac tac acg agg cgc tgc ggc tcc acc tga ccagtgggtc            1774
Ile Gln Asp Tyr Thr Arg Arg Cys Gly Ser Thr
                580                 585 agcaggcacg gctggcagcc ttctctgccc tgagggtcga aggtcgagca ggccgggggt     1834
gtccgggagg tctttgggca tcgcggtctg gggttgggac gtgtaagcgc ctggagagc     1894 ctagaccagg ctccgggctg ccaataaaga agtgaaatgc gtaaaaaaaa a              1945

<210> SEQ ID NO 10
<211> LENGTH: 587
<212> TYPE: PRT
<213> ORGANISM: Homo sapiens

<400> SEQUENCE: 10

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Leu Leu Glu Gln Ile His Lys Val His Phe
                165                 170                 175

Leu Leu His Lys Asp Thr Val Ala Phe Asn Asp Asn Arg Asp Pro Leu
            180                 185                 190
```

```
Ser Ser Tyr Asn Ile Ile Ala Trp Asp Trp Asn Gly Pro Lys Trp Thr
        195                 200                 205

Phe Thr Val Leu Gly Ser Ser Thr Trp Ser Pro Val Gln Leu Asn Ile
    210                 215                 220

Asn Glu Thr Lys Ile Gln Trp His Gly Lys Asp Asn Gln Val Pro Lys
225                 230                 235                 240

Ser Val Cys Ser Ser Asp Cys Leu Glu Gly His Gln Arg Val Thr
                245                 250                 255

Gly Phe His His Cys Cys Phe Glu Cys Val Pro Cys Gly Ala Gly Thr
                260                 265                 270

Phe Leu Asn Lys Ser Asp Leu Tyr Arg Cys Gln Pro Cys Gly Lys Glu
        275                 280                 285

Glu Trp Ala Pro Glu Gly Ser Gln Thr Cys Phe Pro Arg Thr Val Val
    290                 295                 300

Phe Leu Ala Leu Arg Glu His Thr Ser Trp Val Leu Ala Ala Asn
305                 310                 315                 320

Thr Leu Leu Leu Leu Leu Leu Gly Thr Ala Gly Leu Phe Ala Trp
                325                 330                 335

His Leu Asp Thr Pro Val Val Arg Ser Ala Gly Gly Arg Leu Cys Phe
        340                 345                 350

Leu Met Leu Gly Ser Leu Ala Ala Gly Ser Gly Ser Leu Tyr Gly Phe
    355                 360                 365

Phe Gly Glu Pro Thr Arg Pro Ala Cys Leu Leu Arg Gln Ala Leu Phe
    370                 375                 380

Ala Leu Gly Phe Thr Ile Phe Leu Ser Cys Leu Thr Val Arg Ser Phe
385                 390                 395                 400

Gln Leu Ile Ile Ile Phe Lys Phe Ser Thr Lys Val Pro Thr Phe Tyr
                405                 410                 415

His Ala Trp Val Gln Asn His Gly Ala Gly Leu Phe Val Met Ile Ser
                420                 425                 430

Ser Ala Ala Gln Leu Leu Ile Cys Leu Thr Trp Leu Val Val Trp Thr
        435                 440                 445

Pro Leu Pro Ala Arg Glu Tyr Gln Arg Phe Pro His Leu Val Met Leu
    450                 455                 460

Glu Cys Thr Glu Thr Asn Ser Leu Gly Phe Ile Leu Ala Phe Leu Tyr
465                 470                 475                 480

Asn Gly Leu Leu Ser Ile Ser Ala Phe Ala Cys Ser Tyr Leu Gly Lys
                485                 490                 495

Asp Leu Pro Glu Asn Tyr Asn Glu Ala Lys Cys Val Thr Phe Ser Leu
        500                 505                 510

Leu Phe Asn Phe Val Ser Trp Ile Ala Phe Phe Thr Thr Ala Ser Val
    515                 520                 525

Tyr Asp Gly Lys Tyr Leu Pro Ala Ala Asn Met Met Ala Gly Leu Ser
    530                 535                 540

Ser Leu Ser Ser Gly Phe Gly Gly Tyr Phe Leu Pro Lys Cys Tyr Val
545                 550                 555                 560

Ile Leu Cys Arg Pro Asp Leu Asn Ser Thr Glu His Phe Gln Ala Ser
                565                 570                 575

Ile Gln Asp Tyr Thr Arg Arg Cys Gly Ser Thr
        580                 585

<210> SEQ ID NO 11
<211> LENGTH: 2373
```

```
<212> TYPE: DNA
<213> ORGANISM: Homo sapiens
<220> FEATURE:
<221> NAME/KEY: CDS
<222> LOCATION: (1)..(1443)

<400> SEQUENCE: 11 atg ctg ctc tgc acg gct cgc ctg gtc ggc ctg cag ctt ctc att tcc      48
Met Leu Leu Cys Thr Ala Arg Leu Val Gly Leu Gln Leu Leu Ile Ser
 1               5                  10                  15 tgc tgc tgg gcc ttt gcc tgc cat agc acg gag tct tct cct gac ttc      96
Cys Cys Trp Ala Phe Ala Cys His Ser Thr Glu Ser Ser Pro Asp Phe
             20                  25                  30 acc ctc ccc gga gat tac ctc ctg gca ggc ctg ttc cct ctc cat tct     144
Thr Leu Pro Gly Asp Tyr Leu Leu Ala Gly Leu Phe Pro Leu His Ser
         35                  40                  45 ggc tgt ctg cag gtg agg cac aga ccc gag gtg acc ctg tgt gac agg     192
Gly Cys Leu Gln Val Arg His Arg Pro Glu Val Thr Leu Cys Asp Arg
     50                  55                  60 tct tgt agc ttc aat gag cat ggc tac cac ctc ttc cag gct atg cgg     240
Ser Cys Ser Phe Asn Glu His Gly Tyr His Leu Phe Gln Ala Met Arg
65                  70                  75                  80 ctt ggg gtt gag gag ata aac aac tcc acg gcc ctg ctg ccc aac atc     288
Leu Gly Val Glu Glu Ile Asn Asn Ser Thr Ala Leu Leu Pro Asn Ile
                 85                  90                  95 acc ctg ggg tac cag ctg tat gat gtg tgt tct gac tct gcc aat gtg     336
Thr Leu Gly Tyr Gln Leu Tyr Asp Val Cys Ser Asp Ser Ala Asn Val
            100                 105                 110 tat gcc acg ctg aga gtg ctc tcc ctg cca ggg caa cac cac ata gag     384
Tyr Ala Thr Leu Arg Val Leu Ser Leu Pro Gly Gln His His Ile Glu
        115                 120                 125 ctc caa gga gac ctt ctc cac tat tcc cct acg gtg ctg gca gtg att     432
Leu Gln Gly Asp Leu Leu His Tyr Ser Pro Thr Val Leu Ala Val Ile
    130                 135                 140 ggg cct gac agc acc aac cgt gct gcc acc aca gcc gcc ctg ctg agc     480
Gly Pro Asp Ser Thr Asn Arg Ala Ala Thr Thr Ala Ala Leu Leu Ser
145                 150                 155                 160 cct ttc ctg gtg ccc atg att agc tat gcg gcc agc agc gag acg ctc     528
Pro Phe Leu Val Pro Met Ile Ser Tyr Ala Ala Ser Ser Glu Thr Leu
                165                 170                 175 agc gtg aag cgg cag tat ccc tct ttc ctg cgc acc atc ccc aat gac     576
Ser Val Lys Arg Gln Tyr Pro Ser Phe Leu Arg Thr Ile Pro Asn Asp
            180                 185                 190 aag tac cag gtg gag acc atg gtg ctg ctg ctg cag aag ttc ggg tgg     624
Lys Tyr Gln Val Glu Thr Met Val Leu Leu Leu Gln Lys Phe Gly Trp
        195                 200                 205 acc tgg atc tct ctg gtt ggc agc agt gac gac tat ggg cag cta ggg     672
Thr Trp Ile Ser Leu Val Gly Ser Ser Asp Asp Tyr Gly Gln Leu Gly
    210                 215                 220 gtg cag gca ctg gag aac cag gcc act ggt cag ggg atc tgc att gct     720
Val Gln Ala Leu Glu Asn Gln Ala Thr Gly Gln Gly Ile Cys Ile Ala
225                 230                 235                 240 ttc aag gac atc atg ccc ttc tct gcc cag gtg ggc gat gag agg atg     768
Phe Lys Asp Ile Met Pro Phe Ser Ala Gln Val Gly Asp Glu Arg Met
                245                 250                 255 cag tgc ctc atg cgc cac ctg gcc cag gcc ggg gcc acc gtc gtg gtt     816
Gln Cys Leu Met Arg His Leu Ala Gln Ala Gly Ala Thr Val Val Val
            260                 265                 270 gtt ttt tcc agc cgg cag ttg gcc agg gtg ttt ttc gag tcc gtg gtg     864
Val Phe Ser Ser Arg Gln Leu Ala Arg Val Phe Phe Glu Ser Val Val
        275                 280                 285
```

```
ctg acc aac ctg act ggc aag gtg tgg gtc gcc tca gaa gcc tgg gcc        912
Leu Thr Asn Leu Thr Gly Lys Val Trp Val Ala Ser Glu Ala Trp Ala
    290                 295                 300 ctc tcc agg cac atc act ggg gtg ccc ggg atc cag cgc att ggg atg        960
Leu Ser Arg His Ile Thr Gly Val Pro Gly Ile Gln Arg Ile Gly Met
305                 310                 315                 320 gtg ctg ggc gtg gcc atc cag aag agg gct gtc cct ggc ctg aag gcg       1008
Val Leu Gly Val Ala Ile Gln Lys Arg Ala Val Pro Gly Leu Lys Ala
                325                 330                 335 ttt gaa gaa gcc tat gcc cgg gca gac aag aag gcc cct agg cct tgc       1056
Phe Glu Glu Ala Tyr Ala Arg Ala Asp Lys Lys Ala Pro Arg Pro Cys
            340                 345                 350 cac aag ggc tcc tgg tgc agc agc aat cag ctc tgc aga gaa tgc caa       1104
His Lys Gly Ser Trp Cys Ser Ser Asn Gln Leu Cys Arg Glu Cys Gln
        355                 360                 365 gct ttc atg gca cac acg atg ccc aag ctc aaa gcc ttc tcc atg agt       1152
Ala Phe Met Ala His Thr Met Pro Lys Leu Lys Ala Phe Ser Met Ser
    370                 375                 380 tct gcc tac aac gca tac cgg gct gtg tat gcg gtg gcc cat ggc ctc       1200
Ser Ala Tyr Asn Ala Tyr Arg Ala Val Tyr Ala Val Ala His Gly Leu
385                 390                 395                 400 cac cag ctc ctg ggc tgt gcc tct gga gct tgt tcc agg ggc cga gtc       1248
His Gln Leu Leu Gly Cys Ala Ser Gly Ala Cys Ser Arg Gly Arg Val
                405                 410                 415 tac ccc tgg cag acc tct aca gat gcc agc ctt gtg gga aag aag agt       1296
Tyr Pro Trp Gln Thr Ser Thr Asp Ala Ser Leu Val Gly Lys Lys Ser
            420                 425                 430 ggg cac ctg agg gaa gcc aga cct gct tcc cgc gca ctg tgg tgt ttt       1344
Gly His Leu Arg Glu Ala Arg Pro Ala Ser Arg Ala Leu Trp Cys Phe
        435                 440                 445 tgg ctt tgc gtg agc aca cct ctt ggg tgc tgg cag cta aca cgc          1392
Trp Leu Cys Val Ser Thr Pro Leu Gly Cys Cys Trp Gln Leu Thr Arg
    450                 455                 460 tgc tgc tgc tgc tgc tgc ttg gga ctg ctg gcc tgt ttg cct ggc acc       1440
Cys Cys Cys Cys Cys Cys Leu Gly Leu Leu Ala Cys Leu Pro Gly Thr
465                 470                 475                 480 tag acaccctgt ggtgaggtca gcaggggcc gcctgtgctt tcttatgctg              1493
ggctccctgg cagcaggtag tggcagcctc tatggcttct ttggggaacc cacaaggcct    1553
gcgtgcttgc tacgccaggc cctctttgcc cttggtttca ccatcttcct gtcctgcctg    1613
acagttcgct cattccaact aatcatcatc ttcaagtttt ccaccaaggt acctacattc    1673
taccacgcct gggtccaaaa ccacggtgct ggcctgtttg tgatgatcag ctcagcggcc    1733
cagctgctta tctgtctaac ttggctggtg gtgtggaccc cactgcctgc tagggaatac    1793
cagcgcttcc cccatctggt gatgcttgag tgcacagaga ccaactccct gggcttcata    1853
ctggccttcc tctacaatgg cctcctctcc atcagtgcct tgcctgcag ctacctgggt     1913 aaggacttgc cagagaacta caacgaggcc aaatgtgtca ccttcagcct gctcttcaac    1973
ttcgtgtcct ggatcgcctt cttcaccacg gccagcgtct acgacggcaa gtacctgcct    2033
gcggccaaca tgatggctgg gctgagcagc ctgagcagcg gcttcggtgg gtatttctg     2093 cctaagtgct acgtgatcct ctgccgccca gacctcaaca gcacagagca cttccaggcc    2153
tccattcagg actacacgag gcgctgcggc tccacctgac cagtgggtca gcaggcacgg    2213
ctggcagcct tctctgccct gagggtcgaa ggtcgagcag gccggggtg tccgggaggt    2273 ctttgggcat cgcggtctgg ggttgggacg tgtaagcgcc tgggagagcc tagaccaggc   2333
```

-continued tccgggctgc aataaagaa gtgaaatgcg taaaaaaaaa                    2373

<210> SEQ ID NO 12
<211> LENGTH: 480
<212> TYPE: PRT
<213> ORGANISM: Homo sapiens

<400> SEQUENCE: 12

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

```
Ala Phe Met Ala His Thr Met Pro Lys Leu Lys Ala Phe Ser Met Ser
    370             375                 380
Ser Ala Tyr Asn Ala Tyr Arg Ala Val Tyr Ala Val Ala His Gly Leu
385             390                 395                 400
His Gln Leu Leu Gly Cys Ala Ser Gly Ala Cys Ser Arg Gly Arg Val
                405                 410                 415
Tyr Pro Trp Gln Thr Ser Thr Asp Ala Ser Leu Val Gly Lys Lys Ser
            420                 425                 430
Gly His Leu Arg Glu Ala Arg Pro Ala Ser Arg Ala Leu Trp Cys Phe
        435                 440                 445
Trp Leu Cys Val Ser Thr Pro Leu Gly Cys Cys Trp Gln Leu Thr Arg
    450                 455                 460
Cys Cys Cys Cys Cys Cys Leu Gly Leu Leu Ala Cys Leu Pro Gly Thr
465             470                 475                 480
```

<210> SEQ ID NO 13
<211> LENGTH: 2707
<212> TYPE: DNA
<213> ORGANISM: Homo sapiens
<220> FEATURE:
<221> NAME/KEY: CDS
<222> LOCATION: (1)..(2526)

<400> SEQUENCE: 13

```
atg ctg ctc tgc acg gct cgc ctg gtc ggc ctg cag ctt ctc att tcc       48
Met Leu Leu Cys Thr Ala Arg Leu Val Gly Leu Gln Leu Leu Ile Ser
1               5                   10                  15 tgc tgc tgg gcc ttt gcc tgc cat agc acg gag tct tct cct gac ttc       96
Cys Cys Trp Ala Phe Ala Cys His Ser Thr Glu Ser Ser Pro Asp Phe
            20                  25                  30 acc ctc ccc gga gat tac ctc ctg gca ggc ctg ttc cct ctc cat tct      144
Thr Leu Pro Gly Asp Tyr Leu Leu Ala Gly Leu Phe Pro Leu His Ser
        35                  40                  45 ggc tgt ctg cag gtg agg cac aga ccc gag gtg acc ctg tgt gac agg      192
Gly Cys Leu Gln Val Arg His Arg Pro Glu Val Thr Leu Cys Asp Arg
    50                  55                  60 tct tgt agc ttc aat gag cat ggc tac cac ctc ttc cag gct atg cgg      240
Ser Cys Ser Phe Asn Glu His Gly Tyr His Leu Phe Gln Ala Met Arg
65                  70                  75                  80 ctt ggg gtt gag gag ata aac aac tcc acg gcc ctg ctg ccc aac atc      288
Leu Gly Val Glu Glu Ile Asn Asn Ser Thr Ala Leu Leu Pro Asn Ile
                85                  90                  95 acc ctg ggg tac cag ctg tat gat gtg tgt tct gac tct gcc aat gtg      336
Thr Leu Gly Tyr Gln Leu Tyr Asp Val Cys Ser Asp Ser Ala Asn Val
            100                 105                 110 tat gcc acg ctg aga gtg ctc tcc ctg cca ggg caa cac cac ata gag      384
Tyr Ala Thr Leu Arg Val Leu Ser Leu Pro Gly Gln His His Ile Glu
        115                 120                 125 ctc caa gga gac ctt ctc cac tat tcc cct acg gtg ctg gca gtg att      432
Leu Gln Gly Asp Leu Leu His Tyr Ser Pro Thr Val Leu Ala Val Ile
    130                 135                 140 ggg cct gac agc acc aac cgt gct gcc acc aca gcc gcc ctg ctg agc      480
Gly Pro Asp Ser Thr Asn Arg Ala Ala Thr Thr Ala Ala Leu Leu Ser
145                 150                 155                 160 cct ttc ctg gtg ccc atg att agc tat gcg gcc agc agc gag acg ctc      528
Pro Phe Leu Val Pro Met Ile Ser Tyr Ala Ala Ser Ser Glu Thr Leu
                165                 170                 175 agc gtg aag cgg cag tat ccc tct ttc ctg cgc acc atc ccc aat gac      576
Ser Val Lys Arg Gln Tyr Pro Ser Phe Leu Arg Thr Ile Pro Asn Asp
            180                 185                 190
```

```
aag tac cag gtg gag acc atg gtg ctg ctg ctg cag aag ttc ggg tgg      624
Lys Tyr Gln Val Glu Thr Met Val Leu Leu Leu Gln Lys Phe Gly Trp
        195                 200                 205 acc tgg atc tct ctg gtt ggc agc agt gac gac tat ggg cag cta ggg      672
Thr Trp Ile Ser Leu Val Gly Ser Ser Asp Asp Tyr Gly Gln Leu Gly
    210                 215                 220 gtg cag gca ctg gag aac cag gcc act ggt cag ggg atc tgc att gct      720
Val Gln Ala Leu Glu Asn Gln Ala Thr Gly Gln Gly Ile Cys Ile Ala
225                 230                 235                 240 ttc aag gac atc atg ccc ttc tct gcc cag gtg ggc gat gag agg atg      768
Phe Lys Asp Ile Met Pro Phe Ser Ala Gln Val Gly Asp Glu Arg Met
                245                 250                 255 cag tgc ctc atg cgc cac ctg gcc cag gcc ggg gcc acc gtc gtg gtt      816
Gln Cys Leu Met Arg His Leu Ala Gln Ala Gly Ala Thr Val Val Val
        260                 265                 270 gtt ttt tcc agc cgg cag ttg gcc agg gtg ttt ttc gag tcc gtg gtg      864
Val Phe Ser Ser Arg Gln Leu Ala Arg Val Phe Phe Glu Ser Val Val
    275                 280                 285 ctg acc aac ctg act ggc aag gtg tgg gtc gcc tca gaa gcc tgg gcc      912
Leu Thr Asn Leu Thr Gly Lys Val Trp Val Ala Ser Glu Ala Trp Ala
290                 295                 300 ctc tcc agg cac atc act ggg gtg ccc ggg atc cag cgc att ggg atg      960
Leu Ser Arg His Ile Thr Gly Val Pro Gly Ile Gln Arg Ile Gly Met
305                 310                 315                 320 gtg ctg ggc gtg gcc atc cag aag agg gct gtc cct ggc ctg aag gcg     1008
Val Leu Gly Val Ala Ile Gln Lys Arg Ala Val Pro Gly Leu Lys Ala
                325                 330                 335 ttt gaa gaa gcc tat gcc cgg gca gac aag aag gcc cct agg cct tgc     1056
Phe Glu Glu Ala Tyr Ala Arg Ala Asp Lys Lys Ala Pro Arg Pro Cys
        340                 345                 350 cac aag ggc tcc tgg tgc agc agc aat cag ctc tgc aga gaa tgc caa     1104
His Lys Gly Ser Trp Cys Ser Ser Asn Gln Leu Cys Arg Glu Cys Gln
    355                 360                 365 gct ttc atg gca cac acg atg ccc aag ctc aaa gcc ttc tcc atg agt     1152
Ala Phe Met Ala His Thr Met Pro Lys Leu Lys Ala Phe Ser Met Ser
370                 375                 380 tct gcc tac aac gca tac cgg gct gtg tat gcg gtg gcc cat ggc ctc     1200
Ser Ala Tyr Asn Ala Tyr Arg Ala Val Tyr Ala Val Ala His Gly Leu
385                 390                 395                 400 cac cag ctc ctg ggc tgt gcc tct gga gct tgt tcc agg ggc cga gtc     1248
His Gln Leu Leu Gly Cys Ala Ser Gly Ala Cys Ser Arg Gly Arg Val
                405                 410                 415 tac ccc tgg cag ctt ttg gag cag atc cac aag gtg cat ttc ctt cta     1296
Tyr Pro Trp Gln Leu Leu Glu Gln Ile His Lys Val His Phe Leu Leu
        420                 425                 430 cac aag gac act gtg gcg ttt aat gac aac aga gat ccc ctc agt agc     1344
His Lys Asp Thr Val Ala Phe Asn Asp Asn Arg Asp Pro Leu Ser Ser
    435                 440                 445 tat aac ata att gcc tgg gac tgg aat gga ccc aag tgg acc ttc acg     1392
Tyr Asn Ile Ile Ala Trp Asp Trp Asn Gly Pro Lys Trp Thr Phe Thr
450                 455                 460 gtc ctc ggt tcc tcc aca tgg tct cca gtt cag cta aac ata aat gag     1440
Val Leu Gly Ser Ser Thr Trp Ser Pro Val Gln Leu Asn Ile Asn Glu
465                 470                 475                 480 acc aaa atc cag tgg cac gga aag gac aac cag gtg cct aag tct gtg     1488
Thr Lys Ile Gln Trp His Gly Lys Asp Asn Gln Val Pro Lys Ser Val
                485                 490                 495 tgt tcc agc gac tgt ctt gaa ggg cac cag cga gtg gtt acg ggt ttc     1536
Cys Ser Ser Asp Cys Leu Glu Gly His Gln Arg Val Val Thr Gly Phe
```

-continued

```
              500                 505                 510
cat cac tgc tgc ttt gag tgt gtg ccc tgt ggg gct ggg acc ttc ctc    1584
His His Cys Cys Phe Glu Cys Val Pro Cys Gly Ala Gly Thr Phe Leu
        515                 520                 525 aac aag agt gac ctc tac aga tgc cag cct tgt ggg aaa gaa gag tgg    1632
Asn Lys Ser Asp Leu Tyr Arg Cys Gln Pro Cys Gly Lys Glu Glu Trp
530                 535                 540 gca cct gag gga agc cag acc tgc ttc ccg cgc act gtg gtg ttt ttg    1680
Ala Pro Glu Gly Ser Gln Thr Cys Phe Pro Arg Thr Val Val Phe Leu
545                 550                 555                 560 gct ttg cgt gag cac acc tct tgg gtg ctg ctg gca gct aac acg ctg    1728
Ala Leu Arg Glu His Thr Ser Trp Val Leu Leu Ala Ala Asn Thr Leu
                565                 570                 575 ctg ctg ctg ctg ctg ctt ggg act gct ggc ctg ttt gcc tgg cac cta    1776
Leu Leu Leu Leu Leu Leu Gly Thr Ala Gly Leu Phe Ala Trp His Leu
            580                 585                 590 gac acc cct gtg gtg agg tca gca ggg ggc cgc ctg tgc ttt ctt atg    1824
Asp Thr Pro Val Val Arg Ser Ala Gly Gly Arg Leu Cys Phe Leu Met
            595                 600                 605 ctg ggc tcc ctg gca gca ggt agt ggc agc ctc tat ggc ttc ttt ggg    1872
Leu Gly Ser Leu Ala Ala Gly Ser Gly Ser Leu Tyr Gly Phe Phe Gly
610                 615                 620 gaa ccc aca agg cct gcg tgc ttg cta cgc cag gcc ctc ttt gcc ctt    1920
Glu Pro Thr Arg Pro Ala Cys Leu Leu Arg Gln Ala Leu Phe Ala Leu
625                 630                 635                 640 ggt ttc acc atc ttc ctg tcc tgc ctg aca gtt cgc tca ttc caa cta    1968
Gly Phe Thr Ile Phe Leu Ser Cys Leu Thr Val Arg Ser Phe Gln Leu
                645                 650                 655 atc atc atc ttc aag ttt tcc acc aag gta cct aca ttc tac cac gcc    2016
Ile Ile Ile Phe Lys Phe Ser Thr Lys Val Pro Thr Phe Tyr His Ala
            660                 665                 670 tgg gtc caa aac cac ggt gct ggc ctg ttt gtg atg atc agc tca gcg    2064
Trp Val Gln Asn His Gly Ala Gly Leu Phe Val Met Ile Ser Ser Ala
            675                 680                 685 gcc cag ctg ctt atc tgt cta act tgg ctg gtg gtg tgg acc cca ctg    2112
Ala Gln Leu Leu Ile Cys Leu Thr Trp Leu Val Val Trp Thr Pro Leu
690                 695                 700 cct gct agg gaa tac cag cgc ttc ccc cat ctg gtg atg ctt gag tgc    2160
Pro Ala Arg Glu Tyr Gln Arg Phe Pro His Leu Val Met Leu Glu Cys
705                 710                 715                 720 aca gag acc aac tcc ctg ggc ttc ata ctg gcc ttc ctc tac aat ggc    2208
Thr Glu Thr Asn Ser Leu Gly Phe Ile Leu Ala Phe Leu Tyr Asn Gly
                725                 730                 735 ctc ctc tcc atc agt gcc ttt gcc tgc agc tac ctg ggt aag gac ttg    2256
Leu Leu Ser Ile Ser Ala Phe Ala Cys Ser Tyr Leu Gly Lys Asp Leu
            740                 745                 750 cca gag aac tac aac gag gcc aaa tgt gtc acc ttc agc ctg ctc ttc    2304
Pro Glu Asn Tyr Asn Glu Ala Lys Cys Val Thr Phe Ser Leu Leu Phe
            755                 760                 765 aac ttc gtg tcc tgg atc gcc ttc ttc acc acg gcc agc gtc tac gac    2352
Asn Phe Val Ser Trp Ile Ala Phe Phe Thr Thr Ala Ser Val Tyr Asp
770                 775                 780 ggc aag tac ctg cct gcg gcc aac atg atg gct ggg ctg agc agc ctg    2400
Gly Lys Tyr Leu Pro Ala Ala Asn Met Met Ala Gly Leu Ser Ser Leu
785                 790                 795                 800 agc agc ggc ttc ggt ggg tat ttt ctg cct aag tgc tac gtg atc ctc    2448
Ser Ser Gly Phe Gly Gly Tyr Phe Leu Pro Lys Cys Tyr Val Ile Leu
                805                 810                 815 tgc cgc cca gac ctc aac agc aca gag cac ttc cag gcc tcc att cag    2496
```

-continued

```
Cys Arg Pro Asp Leu Asn Ser Thr Glu His Phe Gln Ala Ser Ile Gln
                820                 825                 830 gac tac acg agg cgc tgc ggc tcc acc tga ccagtgggtc agcaggcacg        2546
Asp Tyr Thr Arg Arg Cys Gly Ser Thr
    835                 840 gctggcagcc ttctctgccc tgagggtcga aggtcgagca ggccgggggt gtccgggagg    2606
tctttgggca tcgcggtctg gggttgggac gtgtaagcgc ctgggagagc ctagaccagg    2666
ctccgggctg ccaataaaga agtgaaatgc gtaaaaaaaa a                        2707

<210> SEQ ID NO 14
<211> LENGTH: 841
<212> TYPE: PRT
<213> ORGANISM: Homo sapiens

<400> SEQUENCE: 14

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
```

```
                305                 310                 315                 320
Val Leu Gly Val Ala Ile Gln Lys Arg Ala Val Pro Gly Leu Lys Ala
                    325                 330                 335
Phe Glu Glu Ala Tyr Ala Arg Ala Asp Lys Lys Ala Pro Arg Pro Cys
                    340                 345                 350
His Lys Gly Ser Trp Cys Ser Asn Gln Leu Cys Arg Glu Cys Gln
                    355                 360                 365
Ala Phe Met Ala His Thr Met Pro Lys Leu Lys Ala Phe Ser Met Ser
    370                 375                 380
Ser Ala Tyr Asn Ala Tyr Arg Ala Val Tyr Ala Val Ala His Gly Leu
385                 390                 395                 400
His Gln Leu Leu Gly Cys Ala Ser Gly Ala Cys Ser Arg Gly Arg Val
                    405                 410                 415
Tyr Pro Trp Gln Leu Leu Glu Gln Ile His Lys Val His Phe Leu Leu
                    420                 425                 430
His Lys Asp Thr Val Ala Phe Asn Asp Asn Arg Asp Pro Leu Ser Ser
            435                 440                 445
Tyr Asn Ile Ile Ala Trp Asp Trp Asn Gly Pro Lys Trp Thr Phe Thr
    450                 455                 460
Val Leu Gly Ser Ser Thr Trp Ser Pro Val Gln Leu Asn Ile Asn Glu
465                 470                 475                 480
Thr Lys Ile Gln Trp His Gly Lys Asp Asn Gln Val Pro Lys Ser Val
                485                 490                 495
Cys Ser Ser Asp Cys Leu Glu Gly His Gln Arg Val Val Thr Gly Phe
                500                 505                 510
His His Cys Cys Phe Glu Cys Val Pro Cys Gly Ala Gly Thr Phe Leu
            515                 520                 525
Asn Lys Ser Asp Leu Tyr Arg Cys Gln Pro Cys Gly Lys Glu Glu Trp
    530                 535                 540
Ala Pro Glu Gly Ser Gln Thr Cys Phe Pro Arg Thr Val Val Phe Leu
545                 550                 555                 560
Ala Leu Arg Glu His Thr Ser Trp Val Leu Leu Ala Ala Asn Thr Leu
                565                 570                 575
Leu Leu Leu Leu Leu Leu Gly Thr Ala Gly Leu Phe Ala Trp His Leu
                580                 585                 590
Asp Thr Pro Val Val Arg Ser Ala Gly Gly Arg Leu Cys Phe Leu Met
            595                 600                 605
Leu Gly Ser Leu Ala Ala Gly Ser Gly Ser Leu Tyr Gly Phe Phe Gly
    610                 615                 620
Glu Pro Thr Arg Pro Ala Cys Leu Leu Arg Gln Ala Leu Phe Ala Leu
625                 630                 635                 640
Gly Phe Thr Ile Phe Leu Ser Cys Leu Thr Val Arg Ser Phe Gln Leu
                645                 650                 655
Ile Ile Ile Phe Lys Phe Ser Thr Lys Val Pro Thr Phe Tyr His Ala
                660                 665                 670
Trp Val Gln Asn His Gly Ala Gly Leu Phe Val Met Ile Ser Ser Ala
            675                 680                 685
Ala Gln Leu Leu Ile Cys Leu Thr Trp Leu Val Val Trp Thr Pro Leu
    690                 695                 700
Pro Ala Arg Glu Tyr Gln Arg Phe Pro His Leu Val Met Leu Glu Cys
705                 710                 715                 720
Thr Glu Thr Asn Ser Leu Gly Phe Ile Leu Ala Phe Leu Tyr Asn Gly
                725                 730                 735
```

```
Leu Leu Ser Ile Ser Ala Phe Ala Cys Ser Tyr Leu Gly Lys Asp Leu
            740             745                 750

Pro Glu Asn Tyr Asn Glu Ala Lys Cys Val Thr Phe Ser Leu Leu Phe
        755             760                 765

Asn Phe Val Ser Trp Ile Ala Phe Phe Thr Thr Ala Ser Val Tyr Asp
    770             775             780

Gly Lys Tyr Leu Pro Ala Ala Asn Met Met Ala Gly Leu Ser Ser Leu
785             790             795                         800

Ser Ser Gly Phe Gly Gly Tyr Phe Leu Pro Lys Cys Tyr Val Ile Leu
            805             810                 815

Cys Arg Pro Asp Leu Asn Ser Thr Glu His Phe Gln Ala Ser Ile Gln
            820             825                 830

Asp Tyr Thr Arg Arg Cys Gly Ser Thr
        835             840
```